(12) United States Patent
Ansell et al.

(10) Patent No.: US 10,512,663 B2
(45) Date of Patent: Dec. 24, 2019

(54) GOLD KIWIFRUIT COMPOSITIONS AND METHODS OF PREPARATION AND USE THEREFOR

(71) Applicant: Anagenix IP Limited, Lower Hutt (NZ)

(72) Inventors: Juliet Ansell, Petone (NZ); Paul Blatchford, Lower Hutt (NZ)

(73) Assignee: Anagenix IP Limited, Petone, Lower Hutt (NZ)

(*) Notice: Subject to any disclaimer, the term of this patent is extended or adjusted under 35 U.S.C. 154(b) by 364 days.

(21) Appl. No.: 15/529,734

(22) PCT Filed: Nov. 27, 2015

(86) PCT No.: PCT/NZ2015/050200
§ 371 (c)(1),
(2) Date: May 25, 2017

(87) PCT Pub. No.: WO2016/085356
PCT Pub. Date: Jun. 2, 2016

(65) Prior Publication Data
US 2017/0326190 A1    Nov. 16, 2017

(30) Foreign Application Priority Data

Nov. 28, 2014 (NZ) ........................... 702454
Mar. 27, 2015 (NZ) ........................... 706405

(51) Int. Cl.
| | |
|---|---|
| A61K 36/185 | (2006.01) |
| A61K 9/14 | (2006.01) |
| A23L 19/00 | (2016.01) |
| A61K 9/48 | (2006.01) |

(52) U.S. Cl.
CPC ............ *A61K 36/185* (2013.01); *A23L 19/01* (2016.08); *A61K 9/14* (2013.01); *A61K 9/48* (2013.01); *Y02A 50/481* (2018.01)

(58) Field of Classification Search
None
See application file for complete search history.

(56) References Cited

U.S. PATENT DOCUMENTS

2007/0259059 A1   11/2007   Eidenberger et al.

FOREIGN PATENT DOCUMENTS

| JP | H03246296 A | 11/1991 |
| JP | H10313822 A | 12/1998 |

OTHER PUBLICATIONS

Paturi G. et al. Influence of Green and Gold Kiwifruit on Indices of Large Bowel Function in Healthy Rats. J of Food Science 79(8) 611-620, Aug. 2014. (Year: 2014).*
Edmunds S. et al. Kiwiifruit Extracts Inhibit Cytokine Production by Lipopolysaccharide Activated Macrophages, and Intestinal Epithelial Cells Isolated from Il10 Gene Deficient Mice. Cellular Immunology 270:70-79, 2011. (Year: 2011).*
Khan M. et al. Antioxidants Keep the Potentially Probiotic but Highly Oxygen Sensitive Human Gut Bacterium F. praunitizii Alive at Ambient Air. Plos 9(5)1-7, May 2014. (Year: 2014).*
Blatchford P. et al. In vitro Charactization of the Fermentation Profile and Prebiotic Capacity of Gold Fleshed Kiwifruit. Beneficial Microbes 6(6)829-839, Jun. 30, 2015. (Year: 2015).*
Blatchford P. et al. Consumption of Kiwifruit Capsules Increases F. praunitizii Abundance in Functionally Constipated Individuals. J of Nutritional Science 6:1-10, 2017. (Year: 2017).*
Ansell et al. (Oct. 4, 2015) "Kiwifruit-derived supplements increase stool frequency in healthy adults: a randomized, double-blind, placebo-controlled study," Nutrition Research. 35:401-408.
Edmunds et al. (2011) "Kiwifruit extracts inhibit cytokine production by lipopolysaccharide-activated macrophages, and intestinal epithelial cells isolated from IL10 gene deficient mice," Cellular Immunology. 270:70-79.
Montoya et al. (Jan. 15, 2014) "Dietary Actinidin from Kiwifruit (*Actinidia deliciosa* cv. Hayward) Increases Gastric Digestion and the Gastric Emptying Rate of Several Dietary Proteins in Growing Rats," The Journal of Nutrition. 144:440-446.
Parkar et al. (2012) "In vitro utilization of gold and green kiwifruit oligosaccharides by human gut microbial populations," Plant Foods for Human Nutrition. 67:200-7.
Paturi et al. (Jul. 21, 2014) "Influence of Green and Gold Kiwifruit on Indices of Large Bowel Function in Healthy Rats," Journal of Food Science. 79(8):H1611-H1620.
Rutherfurd et al. (2011) "Effect of actinidin from kiwifruit (*Actinidia deliciosa* cv. Hayward) on the digestion of food proteins determined in the growing rat," Food Chemistry. 129:1681-1689.
Siah et al. (2011) "Using an in-vitro model to predict the prebiotic effects of kiwifruit ingestion on intestinal bacteria Lactobacillus, Bacterioides and Clostridium," Journal of Gastroenterology and Hepatology. 26(Supp. 5):16, Abstract 128.
Sun-Waterhouse et al. (Sep. 4, 2014) "Spray-Drying of Green or Gold Kiwifruit Juice-Milk Mixtures; Novel Formulations and Processes to Retain Natural Fruit Colour and Antioxidants," Food and Bioprocess Technology. 8 (1):191-207.
International Search Report with Written Opinion corresponding to International Patent Application No. PCT/NZ2015/050200, dated May 30, 2017.

(Continued)

*Primary Examiner* — Ralph J Gitomer
(74) *Attorney, Agent, or Firm* — Lathrop Gage LLP; Brian C. Trinque; Benjamin A. Vaughan

(57) ABSTRACT

The present disclosure encompasses compositions prepared from kiwifruit. In particular, the invention encompasses compositions prepared from gold varieties of *Actinidia chinensis*. Also encompassed are methods of preparing these compositions. Further encompassed are methods of using these compositions, in particular, for treating or preventing disorders of the gastrointestinal system, including amongst others: inflammation, constipation, bowel irregularity, microbiota imbalances, irritable bowel syndrome, and inflammatory bowel disease.

18 Claims, 9 Drawing Sheets

(56) References Cited

OTHER PUBLICATIONS

Dong-Geon et al., (2011) "Effects of the Actindia chinensis on loperamide-induced constipation in rat," The Plant Resources Society of Korea, Korean Intellectual Property, Korea, 24(1):2 pages.
Jiege, Huo et al., (2013) "Chinese medicine formula "Weikang Keli" induces autophagic cell death on human gastric cancer cell line SGC-7901," Phytomedicine, 20:159-165.
Database WPI, Week 199732, Thomson Scientific, London, GB; AN 1997-342420, CN 1 107 308 A, Aug. 30, 1995.
Grande et al., (1990) "Allergia al kiwi. Studio clinico-diagnostico su 30 casi," Folia Allergol. Immunol. Clin., 37:313-320 [With English Machine Translation].
Extended European Search Report for European Application No. 15863825.4, dated Jul. 3, 2018.

\* cited by examiner

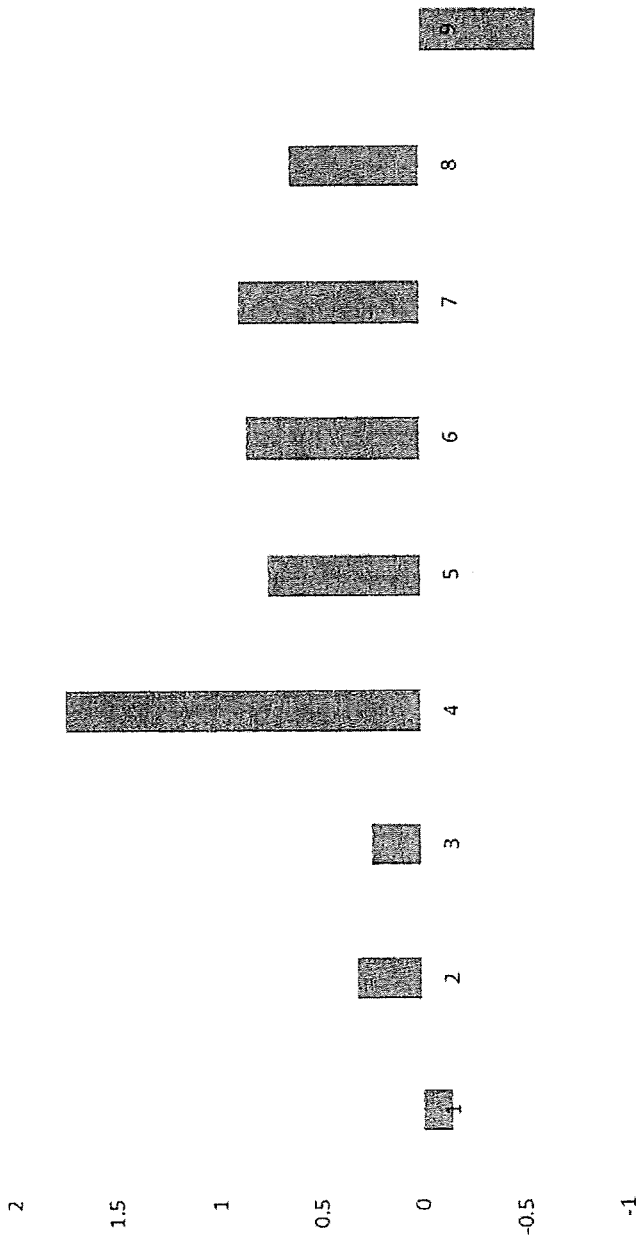

GOLD KIWIFRUIT COMPOSITIONS AND METHODS OF PREPARATION AND USE THEREFOR

RELATED APPLICATIONS

This application is a National Entry Application of PCT application No. PCT/NZ2015/050200, filed on Nov. 27, 2015, which claims the benefit of New Zealand patent application number 702454 filed 28 Nov. 2014, and New Zealand patent application number 706405 filed 27 Mar. 2015, the contents of which are incorporated by reference herein, in their entirety.

FIELD OF THE INVENTION

The present disclosure relates to compositions prepared from gold kiwifruit, *Actinidia chinensis*. Also related are methods of preparing such compositions, and methods of using such compositions, including methods of treating or preventing disorders of the gastrointestinal system.

BACKGROUND OF THE INVENTION

The gastrointestinal tract harbours approximately $10^{14}$ microbial cells, consisting of over 1000 species or phylotypes, the majority of which reside in the colon (Rajilic-Stojanovic and de Vosm 2014; Qin et al. 2010; Egert et al. 2006). The large intestine is a metabolically active site of fermentation, characterised by diverse and intricate microbial relationships that are integral to human health (Backhed et al. 2005). Experimental data have shown the extent to which the colonic microbiota and its human host exist in a delicate state of equilibrium. The microbiota has been shown to be associated with a wide range of health benefits including improved immune function and maturation, modified behaviour, regulation of satiety, inhibition of pathogens, augmentation of mineral absorption and maintenance of energy balance (Geurts et al. 2014; Parnell and Reimer 2012; Bravo et al. 2011; Buffie and Pamer 2013).

This host-microbiota interdependency has been illustrated in a study using mice and zebrafish, where the native microbiotas of each were transplanted into germ-free representatives of the other species. It was found that the composition would revert back to resemble that of the native host microbiota (Rawls et al. 2006). Imbalances in microbial community composition caused by diet, genetics, age, stress, or xenobiotics can induce a state of dysbiosis that may promote a more disease susceptible microbiota. Consumption of certain types of dietary components has a major influence on the communities of colonic microorganisms, with changes typically being observed within 24 hours of consumption (Wu et al. 2011; Parkar et al. 2012).

In the human gastrointestinal tract, *Faecalibacterium prausnitzii* is one of the most populous species, being typically observed at over 5% of the total proportion of the colonic microbiota of healthy adults (Miquel et al. 2013). Members of the Firmicutes phylum, *F. prausnitzii* are commensal inhabitants of the human large bowel, with demonstrated anti-inflammatory properties in vivo (Sokol et al. 2009; Furet et al. 2010). Low levels of *F. prausnitzii* have repeatedly been associated with a range of intestinal disorders including irritable bowel syndrome (IBS), atopy, diabetes and inflammatory bowel diseases (IBD) such as Crohn's disease (CD) and ulcerative colitis (UC) (Sokol et al. 2009; Furet et al. 2010; Rajilic-Stojanovic et al. 2011; Candela et al. 2012; Willing et al. 2010). These consistent observations show that a depleted concentration of *F. prausnitzii* is an undesirable endpoint and therefore any treatment that can selectively stimulate its proliferation is likely to be worthwhile.

The mechanisms by which *F. prausnitzii* facilitate their health promoting effects have been attributed to butyrate production and anti-inflammatory effects. A mouse study by Sokol and colleagues found that *F. prausnitzii* or *F. prausnitzii* supernatant reduced the severity of chemical-induced colitis, promoted the synthesis of anti-inflammatory cytokines, and mitigated proinflammatory cytokine production, suggesting that the anti-inflammatory effects are mediated by secreted metabolites (Sokol et al. 2008). In addition, *F. prausnitzii* generate large amounts of butyrate as well as some lactate and formate as the result of carbohydrate fermentation (Duncan et al. 2002; Duncan et al. 2004).

Constipation is a common condition which can significantly affect an individual's quality of life, with impairment being compared to that of serious chronic conditions such as diabetes and osteoarthritis. It is estimated that up to 20% of the world's population suffer from this condition, with women and individuals aged over 65 years being most frequently affected (Attaluri et al. 2011; Udani & Bloom 2013). Complications that can arise from constipation include anal fissures, rectal prolapse, and faecal impaction. Straining to pass stool may lead to hemorrhoids. In later stages of constipation, the abdomen may become distended, hard, and diffusely tender. Severe cases may exhibit symptoms of bowel obstruction, for example, vomiting and a painful abdomen, as well as encopresis, where soft stool from the small intestine bypasses the mass of impacted faecal matter in the colon.

It is well known that the disturbance of the microbiota balance in the digestive tract may change intestinal motility, resulting in constipation (Husebye et al, 2001; Rhee et al. 2001). In addition, patients with chronic intestinal constipation present imbalance in the microbiota, characterized by a relative decrease of beneficial bacteria and an increase of potentially pathogenic bacteria and fungi (Khalif et al. 2005). Such patients show a significant increase in the counts of *E. coli, S. aureus* and enterobacteria (Khalif et al. 2005).

Moreover, a longer disease progression of chronic constipation leads to higher scores for undesirable microorganisms, and the lower scores for desirable ones (Khalif et al. 2005). In a study with children diagnosed with chronic constipation, intestinal dysbiosis was found in the faeces, with a significant increase in the counts of *Clostridium, Bacteroides*, and *E. coli* (Zoppi et al. 1998). One particular study has found a significant decrease in the count of *Bifidobacterium* and *Lactobacillus* strains in faeces of constipated individuals; such decrease is up to ten times lower for the *Bifidobacterium* genus (Chassard et al. 2012).

The intervention options for constipation remain difficult and challenging, and many individuals are dissatisfied with current therapies and medications. These include lifestyle and dietary modifications such as increased consumption of fruit and vegetables, fibre supplementation (methylcellulose; Konjac glucomannan, psyllium), increased fluid intake and exercise, as well as pharmacological intervention with stool softeners, stimulant laxatives and osmotic laxatives (Attaluri et al. 2011; Leung et al. 2011; Liu 2011).

The routine use of laxatives is contraindicated, as patients may come to be dependent upon their use. Enemas can be used to provide a form of mechanical stimulation. On the other hand, enemas are typically useful only for stool in the rectum, not in the intestinal tract. An increasing range of herbal and other natural products (including aloe and rhubarb (Udani & Bloom 2013)) advertised for aiding laxation have been made available on the market. Yet, there is only anecdotal evidence regarding their efficacy and success in affording relief from constipation.

By contrast, fibre is well known to be important in digestion—soluble fibre attracts water helping to slow digestion, and insoluble fibre adds bulk to stool to assist laxation. Enzymes also aid digestion by breaking down the large dietary compounds into smaller manageable pieces. For example, amylase breaks down starch into simple sugars and proteases break down proteins into amino acids. However, fibre and enzyme supplementation alone are largely ineffective for slow-transit constipation (prolonged delay in the transit of stool through the colon) and defecatory disorders. In addition, such supplementation may have unwanted side-effects such as excessive gas production and uncomfortable bloating.

Green kiwifruit (e.g., *Actinidia deliciosa* var. Hayward) have been highlighted as an effective product in the area of digestion with several studies now demonstrating their efficacy (Stonehouse et al. 2012). The current consensus is that the laxation effect of green kiwifruit appears to be primarily due to its dietary fibre and actinidin (enzyme) content (Chang et al. 2010; Rush et al. 2002, Stonehouse et al. 2012, Drummond & Gearry 2013).

In contrast, gold kiwifruit (e.g., *Actinidia chinensis* var. Hort16A) are not traditionally associated with laxation (Ferguson 2003; Rush 2002). It has been noted that gold kiwifruit has little/no actinidin content and less dietary fibre than green kiwifruit. The Hort16A variety of kiwifruit has been investigated for its effect on immunity (Hunter et al 2012; Skinner 2012), with the contention that the reduced or lesser laxative effects of gold kiwifruit make it an ideal choice for naturally boosting immunity, particularly in children where increased laxation may not be desirable (Adaim 2010).

Given the occurrence of gastrointestinal disorders in the population, there is a need for new compositions, particularly compositions derived from natural sources, for restoring and maintaining digestive health.

SUMMARY OF THE INVENTION

In one aspect, the invention comprises a method of preparing a kiwifruit composition, comprising:

a) obtaining gold kiwifruit which is a Gold3 variety or a genetic derivative thereof;

b) removing the skins of the kiwifruit and pureeing to a sieve size of less than 1 mm; and c) drying the puree and producing a powder.

In various aspects:

The method further comprises removing the seeds of the kiwifruit prior to pureeing.

The method further comprises pureeing the kiwifruit to obtain puree with a Brix value of 16 to 21°.

The method further comprises pureeing the kiwifruit to obtain puree with a viscosity of 11.0 to 13.0, or 10.0 to 14.0, measured at 12.5° Brix, 20° C.

The method further comprises lyophilising the puree and milling to produce the powder.

The method further comprises enriching the composition for polyphenols.

The method further comprises adding polyphenols to the composition.

The method further comprises drying the puree for 24 to 56 hours.

The method further comprises lyophilising the puree for 40 to 56 hours.

In one other aspect, the invention comprises a composition prepared from dried gold kiwifruit, wherein the dried gold kiwifruit is a Gold3 kiwifruit or a genetic derivative thereof. The powder may be produced by a method of any one of the preceding aspects.

In various aspects:

The composition is formulated for enteral administration.

The composition is formulated for oral administration.

The composition is formulated as a tablet or a capsule.

The capsule is a gel capsule.

The tablet or capsule is formulated to comprise 400 to 800 mg of the powder.

Alternatively, the capsule is formulated to comprise 100 to 1000 mg of the powder.

The composition is formulated as a liquid.

The liquid is formulated to comprise 400 to 800 mg of the powder per dosage unit.

The composition is formulated as a jelly or a sachet.

The composition is formulated in combination with a further digestive aid.

The composition is formulated in combination with one or more prebiotic, probiotic, or synbiotic compositions.

The composition is formulated in combination with fibre and/or a digestive enzyme.

The composition is supplemented with polyphenols.

In one other aspect, the invention comprises a method of treating or preventing constipation, or maintaining or improving bowel regularity, comprising: administering to a subject a composition of any one of the preceding aspects, thereby treating or preventing constipation, or maintaining or improving bowel regularity, in the subject.

In various aspects:

The composition is administered enterally.

The composition is administered orally or rectally.

The composition is administered as a tablet, capsule, or liquid.

The composition is administered as a jelly or a sachet.

The capsule is a gel capsule.

The composition is administered at a dosage of 2000 to 4000 mg of powder per day, or a liquid equivalent thereof.

Alternatively, the dosage is 250 to 2500 mg of powder per day, or a liquid equivalent thereof.

The composition is co-administered with further digestive aid.

The composition is co-administered with one or more probiotic, prebiotic, or synbiotic compositions.

The composition is co-administered with fibre and/or a digestive enzyme.

The composition is supplemented with polyphenols.

In one other aspect, the invention comprises a method of treating or preventing microbiota imbalance in the digestive tract, comprising: administering to a subject a composition of any one of the preceding aspects, thereby treating or preventing the microbiota imbalance in the subject.

In various aspects:

The composition is administered enterally.

The composition is administered orally or rectally.

The composition is administered as a tablet, capsule, or liquid.

The composition is administered as a jelly or a sachet.

The capsule is a gel capsule.

The composition is administered at a dosage of 2000 to 4000 mg of powder per day, or a liquid equivalent thereof.

Alternatively, the dosage is 250 to 2500 mg of powder per day, or a liquid equivalent thereof.

The composition is co-administered with further digestive aid.

The composition is co-administered with one or more probiotic, prebiotic, or synbiotic compositions.

The composition is co-administered with fibre and/or a digestive enzyme.

The composition is supplemented with polyphenols.

In yet one other aspect, the invention comprises a method of maintaining or increasing beneficial bacteria in the digestive tract, comprising: administering to a subject a composition of any one of the preceding aspects, thereby maintaining or increasing beneficial bacteria in the digestive tract in the subject.

In various aspects:

The composition is administered enterally.

The composition is administered orally or rectally.

The composition is administered as a tablet, capsule, or liquid.

The composition is administered as a jelly or a sachet.

The capsule is a gel capsule.

The composition is administered at a dosage of 2000 to 4000 mg of powder per day, or a liquid equivalent thereof.

Alternatively, the dosage is 250 to 2500 mg of powder per day, or a liquid equivalent thereof.

The composition is co-administered with further digestive aid.

The composition is co-administered with one or more probiotic, prebiotic, or synbiotic compositions.

The composition is co-administered with fibre and/or a digestive enzyme.

The composition is supplemented with polyphenols.

The beneficial bacteria are selected from: the group of *Bacteroides-Prevotella-Porphyromonas*, *Bifidobacterium* spp., *Lactobacillus* spp., and the *Lachnospiraceae* group.

The beneficial bacteria are selected from: *Faecalibacterium prausnitzii*, *Clostridium coccoides*, *Bacteroides fragilis*, *Bacteroides thetaiotaomicron*, *Bacteroides ovatus*, *Bacteroides cellulosilyticus*, *Roseburia intestinalis*, *Roseburia inulinovorans*, *Ruminococcus bromii*, and *Ruminococcus flavefaciens*.

In still one other aspect, the invention comprises a method of maintaining or increasing *Faecalibacterium prausnitzii* in the digestive tract, comprising:

administering to a subject a composition of any one of the preceding aspects, thereby maintaining or increasing the *Faecalibacterium prausnitzii* in the digestive tract in the subject.

In various aspects:

The composition is administered by enteral, oral, or rectal administration.

The composition is administered as one or more of a tablet, capsule, liquid, jelly, or sachet.

The capsule is a gel capsule.

The composition is administered at a dosage of 2000 to 4000 mg of powder per day, or a liquid equivalent thereof.

The composition is administered at a dosage of 250 to 2500 mg of powder per day, or a liquid equivalent thereof.

The composition is co-administered with further digestive aid.

The composition is co-administered with one or more probiotic, prebiotic, or synbiotic compositions.

The composition is co-administered with fibre and/or a digestive enzyme.

The composition is supplemented with polyphenols.

The subject has one or more symptoms of inflammation.

The subject has one or more symptoms of: Crohn's disease, ulcerative colitis, irritable bowel syndrome, inflammatory bowel disease, gastrointestinal cancer, allergy, atopy, or diabetes.

In even one other aspect, the invention comprises a method of treating or preventing irritable bowel syndrome or inflammatory bowel disease, comprising:

administering to a subject a composition of any one of the preceding aspects, thereby treating or preventing irritable bowel syndrome or inflammatory bowel disease in the subject.

In various aspects:

The composition is administered by enteral, oral, or rectal administration.

The composition is administered as one or more of a tablet, capsule, liquid, jelly, or sachet.

The capsule is a gel capsule.

The composition is administered at a dosage of 2000 to 4000 mg of powder per day, or a liquid equivalent thereof.

The composition is administered at a dosage of 250 to 2500 mg of powder per day, or a liquid equivalent thereof.

The composition is co-administered with further digestive aid.

The composition is co-administered with one or more probiotic, prebiotic, or synbiotic compositions.

The composition is co-administered with fibre and/or a digestive enzyme.

The composition is supplemented with polyphenols.

In still one further aspect, the invention comprises the use of the composition of any one of the preceding aspects for preparing a medicament for:

(i) treating or preventing constipation, or maintaining or improving bowel regularity, in a subject;

(ii) treating or preventing a microbiota imbalance in a subject;

(iii) maintaining or increasing beneficial bacteria in the digestive tract of a subject;

(iv) maintaining or increasing *Faecalibacterium prausnitzii* in the digestive tract of a subject; or (v) treating or preventing irritable bowel syndrome or inflammatory bowel disease in a subject.

The foregoing brief summary broadly describes the features and technical advantages of certain embodiments of the present invention. Further technical advantages will be described in the detailed description of the invention and examples that follows.

Novel features that are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to limit the invention's scope.

BRIEF DESCRIPTION OF THE DRAWINGS

FIG. 5A: Improvement in Digestive Health Index in functionally constipated participants after GOLD (Gold3) treatment.

DETAILED DESCRIPTION OF THE INVENTION

Figure 1:
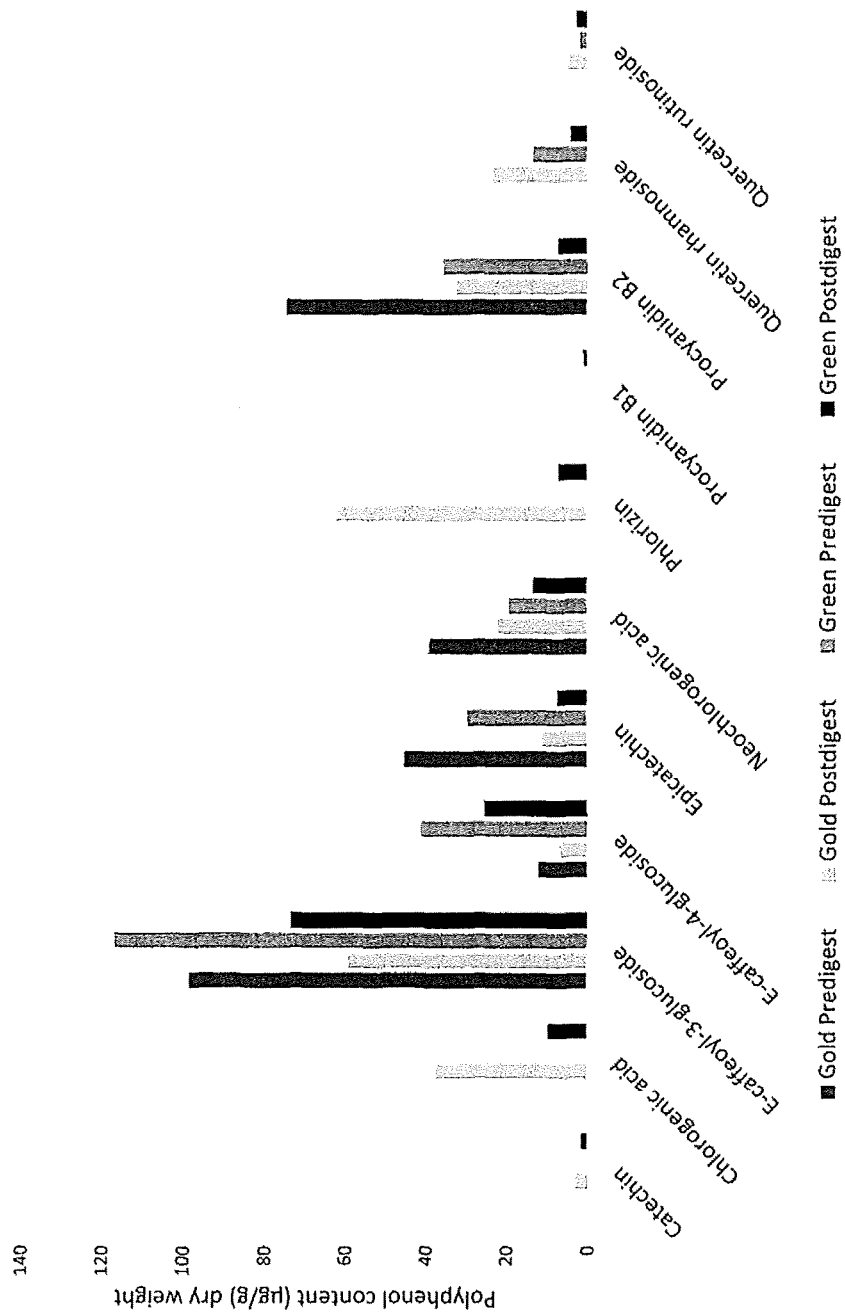
FIG. 1: Polyphenol content of green (Hayward) and gold (Gold3) kiwifruit powder pre- and post-digestion.

The following description sets forth numerous exemplary configurations, parameters, and the like. It should be recognised, however, that such description is not intended as a limitation on the scope of the present invention, but is instead provided as a description of exemplary embodiments.

All references, including patents and patent applications, cited in this specification are hereby incorporated by reference. No admission is made that any reference constitutes prior art. Nor does discussion of any reference constitute an admission that such reference forms part of the common general knowledge in the art, in New Zealand or in any other country.

Definitions

In each instance herein, in descriptions, embodiments, and examples of the present invention, the terms "comprising", "including", etc., are to be read expansively, without limitation. Thus, unless the context clearly requires otherwise, throughout the description and the claims, the words "comprise", "comprising", and the like are to be construed in an inclusive sense as to opposed to an exclusive sense, that is to say in the sense of "including but not limited to".

"Bowel regularity" means having regular bowel movements, e.g., on a daily or weekly basis. While regularity will differ from person to person, an expected number of bowel movements can range from at least four times per week to at least once per day. An "improvement" in regularity means an increase in at least one bowel movement per week.

The term "bowel irregularity" means that the regularity of bowel movements has been compromised. This can mean, for example, an increased time period between bowel movements, or a decrease in the expected number of bowel movements per day or per week. For example, a reduction in at least one bowel movement per week can indicate a bowel irregularity.

As used herein "constipation" means having one or more symptom of being constipated, e.g., one or more of: straining during a bowel movement; hard or lumpy stools; sensation of anorectal obstruction or blockage; sensation of incomplete evacuation; manual manoeuvres to facilitate defecation; or three or fewer bowel movements in a week.

A "dietary aid" is a composition that assists with digestion or other aspects of the digestive system, e.g., soluble and insoluble fibre, digestive enzymes, probiotics, prebiotics, and synbiotics. Included as digestive aids are compositions comprising one or more of psyllium, methylcellulose, glucomannan, magnesium, flaxseed, wheatgrass, ginger, aloe (e.g., aloe vera juice), and rhubarb.

A "digestive enzyme" is an enzyme that assists with the function of the gastrointestinal system. Included are actinidin, amylase, protease, lipase, lactase, maltase, sucrase, and cellulase.

"Digestive tract" and "gut" refer to the digestive system (i.e., gastrointestinal system) of a human and other animal. This includes the oesophagus, stomach, small intestine, including the duodenum, jejunum, and ileum, large intestine, including the cecum, ascending, transverse, descending, and sigmoid colon, and rectum. "Bowel" is a synonym for the intestinal tract.

A "disorder" of the digestive tract includes a disease or other condition affecting the digestive system (i.e., gastrointestinal system), which may be an acute or chronic condition, such as inflammation, constipation, bowel irregularity, microbiota imbalance (e.g., reduced levels of beneficial organisms, altered ratios of beneficial organisms, and/or increased levels of deleterious organisms). Particular disorders include inflammatory bowel disease and irritable bowel syndrome. Other disorders are described in detail herein.

"Gold3" refers to a particular variety of gold kiwifruit also known as 'Zesy002', and marketed as ZESPRI® SUNGOLD kiwifruit. A New Zealand plant variety right application was made on 25 Jun. 2009 for Gold3 under the application number KIW042. The botanical name for Gold3 gold kiwifruit is *Actinidia chinensis* Planch.

A "genetic derivative" of a gold kiwifruit variety (e.g., Gold3 variety) refers to offspring, sports, or other cultivars that are obtained from the gold kiwifruit parent stock. This includes offspring obtained from a genetic cross with the gold kiwifruit parent, e.g., F1 progeny or F2 progeny. The term "genetic derivative" may refer to the derived plant, itself, or to its fruit.

"Inflammation" refers to a condition characterised by one or more of: vasodilation, heat, redness, pain, swelling, edema, lesions, fissures, ulcerations, leukocyte extravasation, and loss of function. Included are both acute and chronic forms of inflammation, the latter of which includes inflammatory disorders, e.g., autoimmune diseases. Particularly included is inflammatory bowel disease. Other inflammatory disorders are described elsewhere in this document.

As noted herein, the terms "lyophilising" and "freeze drying" are used synonymously. It will be understood that the terms "freeze drying"/"lyophilising" do not exclude the use of higher temperatures (i.e., higher than freezing temperatures). For example, higher temperatures may be used for removing residual moisture during the secondary drying phase for lyophilisation/freeze drying procedures.

"Microbiota" as used herein refers to populations of microorganisms that live in the digestive tracts of humans and other animals. Synonymous terms are "microflora" and "microbiome".

A "microbiota imbalance" (also called "dysbiosis") is a condition whereby the number of beneficial organisms in the digestive system is reduced, one or more ratios of beneficial organisms are altered, and/or the number of deleterious organisms in the digestive system is increased. Beneficial organisms may include, for example, lactic acid producing bacteria and butyrate producing bacteria. Particular beneficial organisms include but are not limited to *Bifidobacterium* strains, *Bacteroidaceae* strains such as *Bacteroides fragilis*, and also faecal bacteria, such as beneficial bacteria from the *Clostridium leptum* phylogenetic group, including *Faecalibacterium prausnitzii*, Included as well are *Clostridium coccoides, Bacteroides thetaiotaomicron, Bacteroides ovatus, Bacteroides cellulosilyticus, Roseburia intestinalis, Roseburia inulinovorans, Ruminococcus bromii*, and *Ruminococcus flavefaciens*. Also included are beneficial organisms from the groups of *Bacteroides-Prevotella-Porphyromonas, Lachnospiraceae*, and *Lactobacilli*. Deleterious organisms may include, as non-limiting examples, *Staphylococcus* and *Salmonella* strains, as well as members of the groups *Enterobacteriaceae, Pasteurellacaea, Veillonellaceae*, and *Fusobacteriaceae*.

A "prebiotic" is a composition that increases the number and/or activity of beneficial organisms in the digestive system. Typically, a prebiotic comprises fermentable components and produces positive changes (e.g., improved levels, activities, or ratios) in the populations of beneficial bacteria in the gastrointestinal microbiota. This includes, for example, lactic acid producing bacteria and/or butyrate producing bacteria. Specific examples of beneficial organisms include *Bifidobacterium* strains and *Faecalibacterium* strains, including *Faecalibacterium prausnitzii*, and also *Bacteroidaceae* strains such as *Bacteroides fragilis*. Included as well are *Clostridium coccoides, Bacteroides thetaiotaomicron, Bacteroides ovatus, Bacteroides cellulosilyticus, Roseburia intestinalis, Roseburia inulinovorans, Ruminococcus bromii*, and *Ruminococcus flavefaciens*. Also included are the groups of *Bacteroides-Prevotella-Porphyromonas, Lachnospiraceae*, and *Lactobacilli*, as well as other organisms described herein.

A "probiotic" is a composition comprising one or more beneficial organisms that colonise the digestive system, including the colon, for example, lactic acid producing bacteria and/or butyrate producing bacteria. Particular beneficial organisms include *Bifidobacterium* strains and *Faecalibacterium* strains, including *Faecalibacterium prausnitzii*, and also *Bacteroidaceae* strains such as *Bacteroides fragilis*, as well as other organisms described herein.

A "synbiotic" is a composition that combines one or more prebiotic agents and one or more probiotic organisms.

As used herein, a "subject" may be a human or non-human animal, particularly a mammal, including cattle, sheep, goats, pigs, horses, and other livestock, including, as well, dogs, cats, and other domesticated pets.

"Treating" as used herein is meant as reducing, ameliorating, or resolving a disorder, for example a gastrointestinal disorder, such as a disease or other condition of the gastrointestinal system. A treatment will result in the reduction, amelioration, or elimination of one or more symptoms of the disorder.

"Preventing" as used herein is meant as stopping or delaying the onset of a disorder, for example a gastrointestinal disorder, such as a disease or other condition of the gastrointestinal system. A preventative measure will result in the stoppage or delay of one or more symptoms of the disorder, or a lessening of symptoms if such do arise.

Gold Kiwifruit and Associated Bioactivity

Gold3 is a new variety of gold kiwifruit developed by Zespri®, which has been found to have a tolerance to *Pseudomonas syringae* pv *actinidiae* (Psa; a bacterial kiwifruit vine disease) and is replacing the Hort16A variety as the new commercial gold variety of choice in New Zealand. The Gold3 variety of kiwifruit is similar in nutritional composition to its predecessor, having less actinidin and dietary fibre content than green kiwifruit (Table 1).

TABLE 1

Nutritional content of whole kiwifruit
Average nutritional properties of samples harvested 2009/10[1]

| Component | Units | Gold kiwifruit (*Actinidia chinensis*) | | Green kiwifruit (*Actinidia deliciosa*) |
|---|---|---|---|---|
| | | Gold3 | Hort16A | Hayward |
| Vitamin C | mg/100 g | 133 | 92 | 89 |
| Vitamin E | IU/100 g | 1.4 | 2.1 | 1.4 |
| Fibre dietary soluble | g/100 g | 2.1 | 2.2 | 3.6 |
| Fibre dietary insoluble | g/100 g | <1 | 1.1 | 2.1 |
| Beta carotene | mg/100 g | 0.016 | 0.025 | 0.023 |
| Alpha carotene | mg/100 g | <0.005 | <0.005 | <0.005 |
| Sugars total | g/100 g | 12.7 | 12.4 | 9.5 |
| Folic acid | mg/100 g | 21.4 | 24.6 | 29.9 |
| Oxalate | Raphides/g | 585 | 1267 | 965 |
| Actinidin | FU/100 g | 88 | 3.4 | 334 |
| Nitrogen | mg/100 g | 164 | 148 | 135 |
| Phosphorous | mg/100 g | 25.3 | 23.8 | 26.8 |
| Potassium | mg/100 g | 327.5 | 305 | 335 |
| Calcium | mg/100 g | 23 | 31.8 | 35.3 |
| Magnesium | mg/100 g | 12.7 | 15.4 | 15.3 |
| Sulphur | mg/100 g | 15.2 | 15.3 | 14.8 |
| Iron | mg/100 g | 0.265 | 0.267 | 0.323 |
| Boron | mg/100 g | 0.333 | 0.385 | 0.33 |
| Copper | mg/100 g | 0.106 | 0.131 | 0.095 |
| Manganese | mg/100 g | 0.055 | 0.087 | 0.139 |
| Zinc | mg/100 g | 0.073 | 0.106 | 0.104 |
| Sodium | mg/100 g | <1 | 1.78 | 1.61 |

[1]Zespri ® 2010 New varieties information guide.

Given that gold kiwifruit varieties contain lower levels of fibre and actinidin, the components considered to be primarily responsible for the laxation effects of green kiwifruit, it would be expected that a gold kiwifruit-derived product would have a lesser laxation effect than one derived from green Hayward kiwifruit.

Surprisingly, the inventors have found that Gold3 kiwifruit-derived powder (GOLD) improved laxation to the same degree as the green Hayward kiwifruit-derived powder (ACTAZIN™) in healthy individuals (see Examples 5 and 6, herein below). These results suggest that other kiwifruit bioactive components present in the Gold3 powder may be having a greater impact on the observed laxation effect than current convention dictates. The compositions are therefore useful for maintaining or improving bowel regularity and/or treating or preventing constipation.

Although not wishing to be bound by theory, it is postulated that the polyphenols may be key active ingredients in gold kiwifruit varieties, in particular in the Gold3 variety of kiwifruit. It is postulated that the observed effectiveness for laxation may be attributable to the combination of the fibre, enzymes, prebiotic carbohydrates, and polyphenols in the fruit.

Polyphenols are naturally occurring compounds in plants, characterised by the presence of one or more phenol unit. It is believed that at least some of the health benefits of polyphenols arise through encouraging the growth of beneficial bacteria and by the bacteria converting the polyphenols into other bioactive compounds which are absorbed into the bloodstream and exert effects both in the gut and elsewhere in the body (Seeram 2014; Cardona et al. 2013).

It is estimated that 90 to 95% of total polyphenol intake accumulates in the colon where the phenolics are subjected to metabolism by gut microbes into low molecular weight metabolites. These metabolites are absorbable and may be attributable for the observed health effects of polyphenols (Cardona et al. 2013).

Based on the results shown herein, the inventors believe that the polyphenols of gold kiwifruit varieties, e.g., Gold3 or its derivatives, may have the ability to act as prebiotics. Researchers in the field have described prebiotics as "selectively fermented ingredients that result in specific changes in the composition and/or activity of the gastrointestinal microflora, thus conferring benefit(s) upon host health" (Gibson et al. 2010).

Notably, gold kiwifruit have higher levels of polyphenols than green kiwifruit (see, e.g., Drummond 2013; see also Table 5, herein). Moreover, the inventors' in vitro studies have shown that digested (simulated upper gastrointestinal digestion) Gold3 gold kiwifruit powder has an altered polyphenol profile compared to pre-digestion (see Example 2); however, the overall phenolic content is retained. Although green kiwifruit powder also has an altered polyphenol profile post-digestion, the overall content is reduced by digestion (see Example 2).

From this, the inventors conclude that the polyphenols present in the Gold3 gold kiwifruit powder are surviving digestion in the stomach, better than those in the green kiwifruit powder. This means that the polyphenols from gold kiwifruit such as the Gold3 variety of kiwifruit are available for biotransformation into different phenolics.

Without wishing to be bound by theory, it is believed that the Gold3 gold kiwifruit has a unique profile rich in chlorogenic acid, E-caffeoyl-3-glucoside, phlorizin, procyanidin B2, and quercetin. It is believed that these phenolics remain 'undigested' and therefore transit into the colon where they are metabolised by the gut microbiota into metabolites (phenolic derivatives). These derivatives can then be absorbed and go on to interact in other metabolic pathways and support health benefits, including facilitated laxation.

It is known that the phenylpropanoid pathway produces the majority of phenolic compounds found in plants. Phenylpropanoids control plants' repair, growth and defense systems (immune systems), and their interaction with beneficial microbes and beneficial predators (trophic systems). Thus, it is feasible that phenolic compounds in the Gold3 variety may be responsible for both the pest-resistance of the plant and the digestive benefits of the Gold3-derived powder, as disclosed herein.

The inventors have also found that Gold3 gold kiwifruit powder contains digestion-resistant components, which are known to have prebiotic properties (see Example 4). These components assist in modulating the gut microbiota, and stimulating the production of metabolites such as short chain fatty acids (SCFAs; see Example 4), which are attributed with various health benefits.

Additionally, the inventors have discovered that Gold3 gold kiwifruit powder influences the growth pattern of gut microflora, stimulating an increase in beneficial bacteria relative to harmful bacteria (see Example 3). Notably, the inventors have also observed a significant increase in the relative abundance of *Faecalibacterium prausnitzii* in faecal samples of constipated patients treated with Gold3 gold kiwifruit powder (Examples 7 and 8). This increase in beneficial bacteria, including *F. prausnitzii*, has been confirmed by quantitative PCR analysis (Examples 9 and 10).

This is a significant finding as depleted concentrations of *F. prausnitzii* are associated with gastrointestinal disorders, and in particular, inflammatory conditions of the gastrointestinal tract. It is noted that reduced levels of *F. prausnitzii* have been associated, specifically, with irritable bowel syndrome (IBS) and inflammatory bowel disease (IBD), as well as other health conditions. See, e.g., Sokol et al. 2008; Sartor 2011. See also, further below.

Therefore, it is evident that Gold3 gold kiwifruit and its genetic derivatives may be used in compositions for: treating or preventing constipation, maintaining or improving bowel regularity, treating or preventing microbiota imbalance, maintaining or increasing beneficial bacteria in the digestive tract, maintaining or increasing *F. prausnitzii* in the digestive tract, and/or treating or preventing irritable bowel syndrome or inflammatory bowel disease. Further uses for the composition are described in detail herein.

Methods of Producing Kiwifruit Compositions

The present invention relates generally to a composition prepared from gold kiwifruit. In one particular aspect, the composition is prepared from *Actinidia chinensis*. Preferably, the Gold3 (also known as G3) variety of gold kiwifruit is used. In other aspects, one or more genetic derivatives from the gold kiwifruit variety may be used. For example, it may be desirable to use F1 or F2 progeny from a genetic cross that includes the parent stock of the gold kiwifruit variety. Alternatively, any sports or other cultivars obtained from the parent may be used.

The composition may be prepared in powdered form, for example, a lyophilised powder, or in any other suitable dosage form. In certain aspects, it may be desirable to formulate the powder into tablets (including rapid dissolve tablets) or capsules (including extended release capsules). The tablets may be scored tablets, chewable tablets, effervescent tablets, orally disintegrating tablets, or tablets for forming a suspension. The capsules may be gel capsules, including gel capsules made by single piece gel encapsulation and two piece gel encapsulation. Non-gelatine capsules are also included, as well as caplets. The powder may be provided in free flowing form or as a solid cake. The composition may be provided as a powder for forming a suspension, powder for forming a solution, bulk oral granules, or bulk oral powder. Alternatively, composition may formulated as a tonic, elixir, linctus, concentrate, syrup, solution, suspension, emulsion, draught, puree, paste, or as drops. In other aspects, the composition may be formulated as a gel or jelly. The composition may be provided in sachet form, for example, a powder sachet, or a gel or jelly sachet. Included also are formulations comprising thin strips, or comprising solids in a capsule to mix with food or drink. Other formulas are also possible, as described herein below.

The compositions of the invention may be prepared from a gold kiwifruit puree obtained from one or more commercial sources. Preferably, the gold kiwifruit puree has had both seeds and skin removed. It is also preferred that the puree has been prepared with a sieve size of about 1 mm or less. It is further preferred that the puree has a viscosity (measured at 12.5° Brix, 20° C.) of about 12.0; or may range from 10.0 to 14.0; or 11.0 to 13.0; or 11.75 to 12.25; or 11.8 to 12.2; or 11.9 to 12.1; or may be about 11.0, about 11.25, about 11.7, about 11.8, about 11.9, about 12.1, about 12.2, about 12.3, or about 12.5.

The pH of the puree may range from 3.2 to 3.8; or 3.0 to 4.0; or 3.1 to 3.9; or may be about 3.1, about 3.2, about 3.3, about 3.4, about 3.5, about 3.6, about 3.7, about 3.8, about 3.9, or about 4.0. In some circumstances, it may be desirable to adjust the pH of the puree or that of the final composition to approximate physiological levels. In particular, it may be useful to obtain a pH range from 6.0 to 8.0; or 6.5 to 7.5; or 6.8 to 7.2; or a pH of about 6.5, about 6.7, about 6.8, about 6.9, about 7.0, about 7.1, about 7.2, about 7.3, about 7.4, or about 7.5.

In certain aspects, the compositions of the invention may be prepared by "soft pulping" technology referred to in New Zealand Patent No. 235972 (which is hereby incorporated by reference), which can be adapted to produce a pulpy gold kiwifruit juice.

In initial preparatory stages, the gold kiwifruit may undergo a pre-treatment process which may include the well known steps of ripening, inspecting, grading, and/or sorting of the kiwifruit. With regard to ripening, it is preferable to use ripe or mature gold kiwifruit when producing the compositions of the invention; however, rotted or decaying material is preferably avoided.

Ripeness can be assessed using widely known and used methods in the art. Ripeness can be measured prior to picking or processing the gold kiwifruit. In particular, ripeness may be measured using the Brix system. Gold kiwifruit with a sugar level ranging from 16 to 21° Brix; or 14° to 23° Brix; or 15° to 22° Brix; or about 14°, about 15°, about 16°, about 17°, about 18°, about 19°, about 20°, about 21°, about 22°, or about 23° Brix, may be indicative of ripeness.

Gold kiwifruit exceeding this Brix level may be overly mature or fermenting and may not produce an ideal composition. Kiwifruit with a Brix level below the ideal may be artificially ripened before use. Time left in storage may be sufficient to achieve ripening. For example, gold kiwifruit picked at about 5° Brix can rise to above 10° Brix in 4-6 weeks in cool storage at 0° C. This fruit will ripen to reach 12° Brix or higher upon removal from cool storage. Other changes in chemistry also occur during ripening so that the kiwifruit is within the ideal range of maturation to provide an optimised product.

As part of the processing, the gold kiwifruit may be sterilised. The fruit may be passed through an assembly having one or more roller brushes for removing any adhering foreign matter. Conventional washing techniques may then be employed. For example, it is possible to use a series of spray nozzles to wash the kiwifruit. Wash additives aiding cleansing or reducing the bacteria count on the kiwifruit may be employed according to local regulations and requirements. For example, the fruit may be washed by a chlorine wash and/or an ozone impregnated water wash followed by a fresh water rinse.

The sterilized gold kiwifruit may then be conveyed into a hopper. This can be tapered to form a funnel to direct the kiwifruit one by one to a cutting assembly. The cutting assembly can include a cutting device such as a water laser or similar, which has the advantage of preventing damage to the seed so the seed of the fruit does not contaminate the pulp. Other suitable cutting devices include rotating circular blades, reciprocating blades, fluid jet cutting devices, swing blades, etc.

The cutting device may cut the gold kiwifruit substantially in half, for example, across its length. Alternately, the cutting device may be replaced with a soft crushing device able to break the skin of the kiwifruit. Preferably this is done without causing significant cellular damage to the kiwifruit. For instance, the gold kiwifruit may be directed between rollers to result in the breakage of the skin of the kiwifruit. In particular, the kiwifruit may be burst by passing the fruit through spaced rollers biased towards each other. This method can be used to squeeze the fruit so the skin is split. The burst kiwifruit remains substantially intact but readily separable into large fragments. Other bursting methods may be employed.

After cutting, the gold kiwifruit segments may be passed through a pressing assembly designed to separate the skin from the pulp. The pressing assembly may be adapted to perform a pulping or comminution process. Such process can be relatively mild and gentle ("soft pulping") compared to conventional fruit pulping techniques. With soft pulping, no significant disintegration or lysis of fruit cells or components. Preferably, only a minor proportion (generally less than 5-10%) of seeds is fragmented by this process. Excluded from soft pulping processes are chemical and/or enzyme lysis methods, thermal techniques, techniques directed to the breaking down of cells, and mechanical techniques which involve excessive pulverization of fruit material.

In one embodiment, the pressing assembly performs the soft pulping of the gold kiwifruit by pressing the kiwifruit segments between a twin converging belt press. The press belts may be multiple loops rotated about a series of pulleys. The distance separating the press belts may decrease in the direction of travel of the kiwifruit. In this way, increased force may be exerted upon the kiwifruit as it travels along the length of the pressing assembly. This can produce pulping of the kiwifruit without significant damage to the seeds. This in turn prevents seeds from contaminating the pulp.

The pulp generated from the pressing assembly may be directed to a screening process, in order to separate the seeds from the pulp. In particular, the pulp may be separated from the seed using a soft mechanical screening technique. For example, a pulp finisher may be used. This includes a rotating flexible impeller which is rotated within a cone shaped screen having apertures of a predetermined size. In particular aspects, the size of the apertures is selected to permit the pulp and juice of the kiwifruit to pass through the screen while retaining a substantial portion, if not all, of the seeds within the interior cavity defined by the screen.

In certain aspects, it may be preferable to use a paste rather than a puree from the gold kiwifruit. A kiwifruit paste may be made as a concentrate. For example, the fruit may be heated for several hours, strained, and reduced to a thick, concentrated form. The fruit may be heated after removing the skins, or after the pulping or pureeing process. The fruit can be heated gradually, and then kept heated at a moderate temperature, with mixing. Upon thickening, the paste can be spread on a flat sheet, or transferred to a packaging, for example, a bag, tube, jar, bottle, or other container. The paste may be transferred aseptically, such that it is suitable for human consumption. Preferably, the kiwifruit paste is produced from mature gold kiwifruit. Preferably, the paste is prepared from pulped fruit. The paste may be a smooth preparation, and may comprise a concentrate of about 40° Brix; or from 30° to 50° Brix; or from 35° to 45° Brix; or about 35°, about 36°, about 370, about 380, about 390, about 41°, about 42°, about 430, about 44°, or about 45° Brix.

The pulp (e.g., in paste or puree form) may then be processed by a freezing step. This may be followed by or used in conjunction with a drying step. In an alternative embodiment, the pulp is dried and processed to a powder without an intervening freezing step. For example, methods involving drum drying may be used. In the drum-drying process, a puree or paste may be dried at relatively low temperatures over rotating, high-capacity drums that produce sheets of drum-dried product. In certain aspects, an additive may be used to accelerate or otherwise assist the drying process. For example, pea starch or other drying aids may be utilised. The dried product may then be milled to a finished flake or powder form. Advantageously, drum drying techniques may be used to produce a dried composition that retains its key components, e.g., phenolic compounds, and can be easily reconstituted using liquid. For example, drum dried products may be made to be cold water soluble. As further alternatives, belt drying or convection drying may be used. Such drying methods are widely known and used in the field.

If freezing is used, it is preferable to freeze the pulp as soon as possible after it is produced to maintain freshness. However, freezing may be carried out within 24 or 48 hours, as needed. Freezing methodologies are well known and need not be described in significant detail herein, Blast freezing is particularly preferred for use with the invention. The pulp may be frozen in standard sized pales, which are used to collect the fresh pulp after processing. The pulp can be stored frozen (e.g., at −18° C.) until it is required to make the composition.

The frozen pulp may be freeze dried, i.e., lyophilised. Freeze drying techniques are widely known and commonly used. The freeze drying cycle may be about 48 hours; or ranging from 40 to 56 hours; or 12 to 36 hours; or 36 to 60 hours; or about 40 hours, about 42 hours, about 44 hours, about 46 hours, about 48 hours, about 50 hours, about 52 hours, or about 54 hours. A longer freeze drying cycle, e.g., at least 48 hours ("gentle freeze drying"), may be used to retain maximal activity. In particular aspects, the process may be carried out to such that water formation is avoided, and the moisture content is minimised during processing.

It may be desirable to use a particular lyophilisation process for obtaining the dried product. For example, a lyophilisation drying program may be used as part of an automated drying system. The lyophilisation process may include multiple drying steps, e.g., with step-wise increases and reductions in temperature. Preferably, a primary drying setting is used for sublimation, followed by one or more secondary drying settings that are used to remove residual moisture. In particular aspects, the top temperature of the lyophilisation process does not exceed 70° C. In other aspects, the temperature of the lyophilisation process ranges between −10° C. to 70° C. In one other aspect, up to 48 hours of lyophilisation is utilised.

The resulting dried product may then be milled into a powder which can then be utilised as appropriate. Milling methods are well known and widely used in the art. Standard mesh sizes may be used to produce the powder, for example, US 20, US 23, US 30, US 35, US 40, US 45, or US 50 mesh sizes may be used. The sieve size for the powder may range from 1.0 to 0.3 mm; or 0.84 to 0.4 mm; or 0.71 to 0.5 mm; or may be about 1.0 mm, about 0.84 mm, about 0.71 mm, about 0.59 mm, about 0.5 mm, about 0.47 mm, about 0.465 mm, about 0.437 mm, about 0.4 mm, about 0.355 mm, or about 0.3 mm.

To ensure minimal degradation of kiwifruit ingredients, the preparation process may be performed at a temperature of less than 40° C. In various embodiments, the process is performed at a temperature ranging from −4° C. to 40° C.; or from −1° C. to 10° C.; or from 1° C. to 6° C.; or at approximately 0° C., approximately 1° C., approximately 2° C., approximately 3° C., approximately 4° C., approximately 5° C., or approximately 6° C. These temperatures may be kept during the entire preparation process, including the storage of the whole fruit, prior to it being broken open, and during the pulping/pureeing process. For optimal results, these temperatures are kept at least from the point that the fruit has been broken open. Use of such temperatures avoids oxidation of the fruit and the use of reducing agents. In certain circumstances, it may be possible to obtain organic certification.

The processing method is preferably performed so as to prevent or at least minimise any damage or effects on the active material in the gold kiwifruit. To ensure optimal production methods, the resulting compositions can be monitored for activity, for example, for polyphenol content. The composition may be expected to contain at least the following polyphenol compounds: chlorogenic acid, E-caffeoyl-3-glucoside, neochlorogenic acid, phlorizin, procyanidin B2, and quercetin rhamnoside. Also present may be: catechin, epicatechin, E-caffeoyl-4-glucoside, and quercetin rutinoside. The levels for these polyphenols are noted herein below. Assays for polyphenols are well known in the art and are also described below. In particular, it is possible to measure gallic acid equivalents (GAE) to determine total polyphenol content. For example, the Folin-Ciocalteu method (employing the Folin-Ciocalteu reagent, also called Folin's phenol reagent or Folin-Denis reagent) may be used for colorimetric in vitro assays of phenolic compounds (Singleton et al. 1999).

Alternatively or additionally, the compositions can be tested for the stimulation of growth of beneficial organisms, e.g., *Lactobacillus* and/or *Bifidobacterium*, or for increased levels of short chain fatty acids, e.g., acetate, butyrate, and/or propionate. These growth levels and organic acid levels are noted herein below. The corresponding assays are widely known and also described in detail herein. Preferably, the noted activities in stimulating bacterial growth and organic acid levels, and the noted polyphenol content are still present upon digestion of the composition, e.g., as assayed by in vitro digestion. In particular aspects, in vitro digestion assays may be utilised as described by the inventors, herein. Other in vitro assays are known and used in the art (see, e.g., Kaur et al. 2010).

In some circumstances, it may be possible to use genetic derivative of the gold kiwifruit stock (e.g., Gold3 stock) to obtain the compositions of the invention. It is expected that a composition obtained from such derivative would share one or more of the characteristics of the compositions obtained from gold kiwifruit stock. Exemplary features include: polyphenol levels and polyphenol profiles, actinidin levels, fibre levels, vitamin levels, stimulation of growth of beneficial organisms, and enhancement of levels of organic acids, as noted above and disclosed in detail herein.

Regarding the fruit itself, it is expected that the kiwifruit obtained from a genetic derivative would share a similar compositional makeup as the gold kiwifruit parent. For example, the vitamin C content of the fruit may be from 100 to 150 mg; or from 90 to 200 mg; or from 80 to 220 mg; or about 80 mg, about 90 mg, about 100 mg, about 115 mg, about 130 mg, about 140 mg, about 150 mg, about 160 mg, about 170 mg, or about 180 mg, per 100 g of fruit. The actinidin content of the fruit may be from 60 to 110 FU; or from 70 to 100 FU; or from 80 to 90 FU; or about 60 FU, about 70 FU, about 80 FU, about 90 FU, about 100 FU, about 110 FU, or about 120 FU, per 100 g of fruit. The total polyphenol content of the fruit may be from 250 to 450 mg GAE; or from 200 to 800 mg GAE; or from 300 to 600 mg GAE; or from 270 to 430 mg GAE; or from 280 to 420 mg GAE; or from 290 to 410 mg GAE; or from 300 to 400 mg GAE; or from 310 to 390 mg GAE; or from 320 to 380 mg GAE, per 100 g of fruit.

Compositions Comprising Gold Kiwifruit

The inventors have found that Gold3 gold kiwifruit powder includes beneficial ingredients that are useful for maintaining the health of the digestive system, as well as treating and preventing digestive problems and/or gastrointestinal disorders. The Gold3 gold kiwifruit powder was shown by the inventors to be particularly efficacious for improving bowel regularity. The Gold3 powder was also effective in stimulating the growth of beneficial bacteria relative to harmful bacteria, and generating increases in *F. prausnitzii*, specifically.

As such, the gold kiwifruit compositions of the invention can be used to support or improve overall gut health and/or to treat or prevent various diseases or other conditions of the digestive tract, including inflammation, constipation, microbiota imbalance, irritable bowel syndrome, and inflammatory bowel disease. In addition, the compositions may be used to maintain or improve bowel regularity, and maintain or increase beneficial bacteria in the digestive tract, including *F. prausnitzii*.

The gold kiwifruit powder may be encapsulated, tableted, or added to or incorporated in other products. Particularly encompassed are delayed release formulas, extended release formulas, as well as formulas for rapid disintegration. Gel capsules are specifically encompassed, as well as sachets and chewable tablets. Additionally included are combination formulas, which include the powder of the invention mixed with other beneficial agents, e.g., one or more probiotics, prebiotics, synbiotics, or other digestive aids. In alternate embodiments, the powder may be reconstituted as a liquid, for example, a concentrate, syrup, suspension, or tonic for oral administration, or as an enema or cluster composition for rectal administration. Rectal suppositories are also encompassed.

In preferred aspects, the resulting dried gold kiwifruit powder is encapsulated, and each capsule contains approximately 500 mg or approximately 600 mg of the dried powder; or ranging from 50 to 650 mg; 150 to 850 mg; or 200 to 800 mg; 300 to 700 mg; or 550 to 750 mg; or approximately 50 mg, approximately 100 mg, approximately 150 mg, approximately 200 mg, approximately 250 mg, approximately 300 mg, approximately 350 mg, approximately 400 mg, approximately 450 mg, approximately 500 mg, approximately 550 mg, approximately 575 mg, approximately 590 mg, approximately 610 mg, approximately 625 mg, approximately 650 mg, approximately 675 mg, approximately 700 mg, approximately 750 mg, approximately 800 mg, or approximately 850 mg, of the dried powder.

In certain circumstances, it may be desirable to isolate or enrich the polyphenols from the gold kiwifruit. In particular, it may be advantageous to use the gold kiwifruit to obtain polyphenol enriched compositions, phenolic concentrates, or compositions comprising isolated phenolics. For example, the compositions of the invention may be enriched for polyphenols such that their concentration is increased relative to the other components of the gold kiwifruit, e.g., fibre, sugars, and/or proteins. In particular aspects, the compositions of the invention may include polyphenols that have been isolated away from (e.g., purified from) the other components of the gold kiwifruit.

Methods of enriching and extracting polyphenols are widely known in the art (see, e.g., Sun-Waterhouse et al. 2009; Eidenberger et al. 2014). Preferably, the resulting composition has at least 2 times, at least 3 times, at least 4 times, at least 5 times, or at least 10 times the amount of polyphenols compared to the composition prepared without polyphenol enrichment or isolation steps. The polyphenol enriched compositions, phenolic concentrates, and compositions comprising isolated phenolics may be dried as a powder, and used in accordance with the present invention. In particular aspects, such powder is encapsulated, and each capsule contains approximately 100 mg, approximately 150 mg, approximately 200 mg, approximately 250 mg, approximately 300 mg, or approximately 350 mg, or approximately 400 mg, of powder; or ranging from 100 mg to 200 mg; or from 100 to 300 mg; or from 200 to 400 mg of powder.

The dosage form may contain excipients, for example, one or more anti-adherents, binders, coatings, disintegrants, flavours, colours, sweeteners, lubricants, glidants, flow agents, anti-caking agents, sorbents, or preservatives. Useful excipients include but are not limited to: stearin, magnesium stearate, and stearic acid; saccharides and their derivatives, e.g., disaccharides: sucrose, lactose; polysaccharides and their derivatives, e.g., starches, cellulose or modified cellulose such as microcrystalline cellulose and cellulose ethers such as hydroxypropyl cellulose; sugar alcohols such as isomalt, xylitol, sorbitol and maltitol; proteins such as gelatin; synthetic polymers such as polyvinylpyrrolidone, polyethylene glycol; fatty acids, waxes, shellac, plastics, and plant fibers, e.g., corn protein zein; hydroxypropyl methylcellulose; crosslinked polymers, e.g., crosslinked polyvinylpyrrolidone (crospovidone), and crosslinked sodium carboxymethyl cellulose (croscarmellose sodium); sodium starch glycolate; silicon dioxide, fumed silica, talc, and magnesium carbonate.

It is expected that the gold kiwifruit compositions of the invention will include various components, for example, carbohydrates, dietary fibre, polyphenols, and actinidin. In various aspects, there may be from 10 to 20 mg carbohydrates; from 0.5 to 5.5 mg dietary fibre; from 0.1 to 0.5 mg GAE polyphenols; and from 100 to 500 AU actinidin, per 25 mg powder. In one particular aspect, there may be approximately 18 mg carbohydrates, approximately 3.0 mg dietary fibre, approximately 0.28 mg GAE polyphenols, and approximately 230 AU actinidin, per 25 mg powder.

The gold kiwifruit compositions of the invention may include particular polyphenols as active components. The polyphenols in the composition may still be present upon digestion of the composition, e.g., in vitro digestion, as described in detail herein. For example, following digestion, the chlorogenic acid content of the composition may be at least 40 µg/g, at least 45 µg/g, at least 50 µg/g, or at least 55 µg/g; or from 40 to 60 µg/g; or from 45 to 55 µg/g, based on dry weight. The E-caffeoyl-3-glucoside content of the composition may be at least 45 µg/g, at least 50 µg/g, at least 55 µg/g, at least 60 µg/g, at least 65, at least 70 µg/g, or at least 75 µg/g; or from 40 to 80 µg/g; or from 50 to 70 µg/g, based on dry weight. The epicatechin content of the composition may be at least 6 µg/g, at least 7 µg/g, at least 8 µg/g, at least 9 µg/g, at least 10 µg/g, at least 11 µg/g, at least 12 µg/g, at least 13 µg/g, or at least 14 µg/g; or from 8 to 12 µg/g; or from 9 to 11 µg/g, based on dry weight. The neochlorogenic acid content of the composition may be at least 15 µg/g, at least 18 µg/g, at least 20 µg/g, at least 22 µg/g, at least 25, at least 30 gig/g, or at least 35 µg/g; or from 10 to 30 µg/g; or from 15 to 25 µg/g, based on dry weight.

In further aspects, following digestion, the phlorizin content of the gold kiwifruit compositions may be at least at least 45 µg/g, at least 50 µg/g, at least 55 µg/g, at least 60 µg/g, at least 65, at least 70 µg/g, or at least 75 µg/g; or from 40 to 80 µg/g; or from 50 to 70 µg/g, based on dry weight. The procyanidin B2 content may be at least 15 µg/g, at least 20 µg/g, at least 25 µg/g, at least 30, at least 35 µg/g, at least 40 µg/g, or at least 45 µg/g; or from 20 to 40 µg/g; or from 25 to 35 µg/g, based on dry weight. The quercetin rhamnoside content of the composition may be at least at least 15 µg/g, at least 18 µg/g, at least 20 µg/g, at least 22 µg/g, at least 25, at least 30 µg/g, or at least 35 µg/g; or from 10 to µg/g; or from 15 to 25 µg/g, based on dry weight.

In still further aspects, following digestion, the catechin content of the gold kiwifruit compositions may be at least 0.5 µg/g, at least 1 µg/g, at least 2 µg/g, or at least 3 µg/g; or from 1 to 4 µg/g; or from 2 to 3 µg/g, based on dry weight. The E-caffeoyl-4-glucoside content of the composition may be at least 3 µg/g, at least 4 µg/g, at least 5 µg/g, at least 6 µg/g, at least 7 µg/g, at least 8 µg/g, or at least 9 µg/g; or from 4 to 8 µg/g; or from 5 to 7 µg/g, based on dry weight. The quercetin rutinoside content of the composition may be at least 1 µg/g, at least 2 µg/g, at least 3 µg/g, at least 4 µg/g, or at least 5 µg/g; or from 1 to 5 µg/g; or from 2 to 4 µg/g, based on dry weight.

In the absence of digestion, the gold kiwifruit compositions of the invention may include a total polyphenol content of from 1000 to 1200 mg GAE; or from 900 to 1300 mg GAE; or from 800 to 1400 mg GAE, per 100 g. The content of E-caffeoyl-3-glucoside may be from 60 to 120 µg/g; or from 80 to 100 µg/g; or from 90 to 110 µg/g; or about 80 µg/g, about 90 µg/g, about 100 µg/g, about 110 µg/g, about 115 µg/g, or about 120 µg/g., based on dry weight. The content of epicatechin may be from 20 to 60 µg/g; or from 30 to 50 µg/g; or about 20 µg/g, about 30 µg/g, about 40 µg/g, about 45 µg/g, about 50 µg/g, or about 60 µg/g, based on dry weight. The content of neochlorogenic acid may be from 20 to 60 µg/g; or from 30 to 50 µg/g; or about 20 µg/g, about 30 µg/g, about 39 µg/g, about 40 µg/g, about 41 µg/g, about 50 µg/g, or about 60 µg/g, based on dry weight. The content of procyanidin B2 may be from 40 to 120 µg/g; or from 50 to 100 µg/g; or from 65 to 90 µg/g; or from 60 to 80 µg/g; or about 40 µg/g, or about 50 µg/g, or about 60 µg/g, or about 70 µg/g, or about 75 µg/g, or about 80 µg/g, or about 90 µg/g, or about 100 µg/g, based on dry weight.

The gold kiwifruit compositions of the invention may also include fibre as an active component. In particular aspects, the total fibre content may be from 12.4 to 12.7%, based on dry weight; or from 12.0 to 13.0%; or from 10 to 15%; or about 10%, about 11%, about 12%, about 13%, about 14%, or about 15%, based on dry weight. In additional aspects, the soluble fibre content may be from 3.4 to 3.5% based on dry weight; or from 3.0 to 4.0%; or from 3.2 to 3.8%; or about 3.0%, about 3.1%, about 3.2%, about 3.3%, about 3.4%, about 3.5%, about 3.6%, about 3.7%, about 3.8%, about 3.9%, or about 4.0%, based on dry weight. In further aspects, the insoluble fibre content may be from 8.9 to 9.3%, based on dry weight; or from 8.0 to 10.0%; or from 8.5 to 9.5%; or about 8.0%, about 8.5%, about 9.0%, about 9.5%, or about 10.0%, based on dry weight.

The gold kiwifruit compositions of the invention may also include various sugars, including neutral sugars and uronic acids. Pectic polysaccharides are specifically included in the compositions of the invention, Regarding neutral sugars, the compositions in the invention may include one or more of: rhamnose, arabinose, galactose, and glucose.

The gold kiwifruit compositions of the invention may further include actinidin enzyme. In particular aspects, the actinidin levels may be from 8,000 to 11,000 AU; or from 6,000 to 16,000 AU; from or from 7,000 to 11,000 AU; or from 8,000 to 10,000 AU; or about 8,000 AU, about 9,000 AU, about 10,000 AU, about 11,000 AU, or about 15,000 AU, per gram. Methods for measuring actinidin level are widely known and used in the art. See, e.g., Drummond 2013 and Kaur et al. 2010. For example, it is possible to measure N-α-CBZ-lys-p-nitrophenol (Z-lys-pNp; Sigma Aldrich Pty Ltd) digestion, for example, at 25° C. (i.e., 77° F.), to determine actinidin levels/activity (Boland & Hardman 1972). Measurements can be expressed as AU/g or AU/mg for the composition. Alternatively, it is possible to measure actinidin levels using fluorescent assays to assess cysteine protease activity (Nieuwenhuizen et al. 2012; Madumage 2013). In particular, fluorescent substrates Z-FRAMC (benzyloxycarbonyl-Phe-Arg-7-amino-4-methylcoumarin), H-D-Ala-Leu-Lys-AMC, or Bz-Arg-AMC (Feinchemikalien AG) may be used. These measurements can be expressed as FU/g or FU/mg for the composition.

The gold kiwifruit compositions of the invention are expected to be active in stimulating the growth of beneficial enteric organisms (e.g., beneficial bacteria) such as members of *Lactobacillus* or *Bifidobacterium* groups, as well as certain members of the *Clostridiales* group, including *Faecalibacterium prausnitzii*, as demonstrated herein. Other beneficial organisms may also show increased growth, for example, *Erysipelotrichales* and *Bacteroidales* strains. Included as well are beneficial organisms that include *Clostridium coccoides, Bacteroides thetaiotaomicron, Bacteroides ovatus, Bacteroides cellulosilyticus, Roseburia intestinalis, Roseburia inulinovorans, Ruminococcus bromii*, and *Ruminococcus flavefaciens*. Also included are beneficial organisms within the groups of *Bacteroides-Prevotella-Porphyromonas*, and *Lachnospiraceae*, as well as other organisms described herein.

In various aspects of the invention, the gold kiwifruit composition (e.g., 25 mg of powder, which can be diluted in 0.3 to 0.5 mg/ml powder) may increase the growth of one or more *Lactobacillus* and/or *Bifidobacterium* strains (e.g., starting with 1 billion cfu) by at least 20%, at least 30%, at least 40%, at least 50%, at least 60%, at least 70%, at least 80%, at least 90%, at least 100%, or at least 110%. In one particular aspect, 25 mg of powder added to 1 billion cfu of probiotic organism(s) may be used to obtain a growth rate of greater than 50%, relative to the control, which has been normalized to 0%. Such increases may still be observed upon digestion of the composition, e.g., in vitro digestion, as described in detail herein. Preferably, there are no concomitant increases in deleterious enteric organisms (e.g., harmful bacteria) such as *Salmonella* and/or *Staphylococcus* strains. In some cases it may be possible to achieve decreases in one or more deleterious organisms.

The gold kiwifruit compositions of the invention may also be active in stimulating the growth of faecal bacteria, including *Clostridiales* bacteria such as those from the *Clostridium leptum* phylogenetic group, and in particular *Faecalibacterium* strains, including *Faecalibacterium prausnitzii*. Increases in the relative abundance of *Faecalibacterium prausnitzii* may be at least 20%, at least 30%, at least 40%, at least 50%, at least 60%, at least 70%, at least 80%, at least 90%, at least 100%, at least 150%, or at least 200%; or 20% to 200%; or 50% to 150%; or 70% to 100%, in subjects, e.g., constipated subjects, upon treatment with the gold kiwifruit powder.

The gold kiwifruit compositions of the invention show activity in increasing levels of short chain fatty acids. In particular aspects of the invention, the composition (e.g., 10 mg of powder) may increase the levels of one or more of acetate, butyrate, and propionate by at least 10%, at least 15%, at least 18%, at least 20%, at least 22%, at least 25%, at least 28%, or at least 30%. Such increases may still be observed upon digestion of the composition, e.g., in vitro digestion, as described in detail herein.

Methods of Using Kiwifruit Compositions

As noted above, the gold kiwifruit compositions of the invention can be used to support or improve overall gut health and/or to treat or prevent various conditions of the digestive tract, including inflammation, constipation, microbiota imbalance, irritable bowel syndrome, and inflammatory bowel disease. In addition, the compositions may be used to maintain or improve bowel regularity, and to maintain or increase beneficial bacteria in the digestive tract, including *F. prausnitzii*.

Constipation may be caused by a disorder of bowel function or a structural problem, and may have one or more symptoms of: reduced bowel movements, incomplete and assisted bowel movements, straining, hard or lumpy stool forms, bloating, flatulence, abdominal pain, and reliance on laxatives, Common causes of constipation include: inadequate water intake; inadequate fibre in the diet; a disruption of regular diet or routine; inadequate activity or exercise; consumption of large amounts of dairy products; stress; avoidance of bowel movements (e.g., due to pain); overuse of laxatives or stool softeners; hypothyroidism; neurological conditions such as Parkinson's disease or multiple sclerosis; antacid medicines containing calcium or aluminium; medicines (especially pain medicines, such as narcotics, antidepressants, or iron supplements); depression; eating disorders; irritable bowel syndrome; pregnancy; colon cancer; and lack of nerve and muscle function in the bowel.

The etiology of microbiota imbalances (e.g., decreases in beneficial organisms, altered ratios of beneficial organisms, and/or increases in deleterious organisms) is complex and yet to be fully elucidated. Imbalances may be caused by certain medicines such as antibiotics, disorders of the digestive tract, or dietary insufficiencies. A gut microbiota imbalance may show up as one or more symptoms of: diarrhoea, particularly antibiotic-associated diarrhoea, runny stools, constipation, and/or bloating.

Microbiota imbalances are correlated with various disorders of the gastrointestinal system, as well as other disorders. In particular, an imbalance in the microbiota may be associated with inflammatory bowel disease, irritable bowel syndrome, coeliac disease, Crohn's disease, ulcerative colitis, necrotizing enterocolitis, intestinal inflammation, enteric infections, carcinogenesis including gastric carcinomas, colorectal carcinomas, cholelithiasis, endotoxemia, hepatic disease such as cirrhosis, and hepatic encephalopathy.

Microbial imbalances in the digestive tract are associated with a number of different health conditions, including:

| Disorder | Observations | System/organ affected | References |
| --- | --- | --- | --- |
| Crohn's disease | Diversity decrease - reduced *F. prausnitzii* | GIT | (Fujimoto et al. 2013; Willing et al. 2010) |
| Ulcerative colitis | Diversity decrease - reduced *A. muciniphila* and *F. prausnitzii* | GIT | (Lepage et al. 2011; Sokol et al. 2009) |
| Irritable bowel syndrome | Increased *Clostridium* cluster IX, decreased *Bacteroides* spp. | GIT | (Jeffery et al. 2012; Maccaferri et al. 2012) |
| GIT cancer | Diversity decrease, variation in *Bacteroides* spp., increased Fusobacteria spp., reduced *F. prausnitzii* | GIT | (Chen et al. 2012; Wang et al. 2012) |
| Allergy/Atopy | Diversity decrease, increased Enterobacteriaceae, reduced *A. muciniphila* and *F. prausnitzii* | Systemic | (Abrahamsson et al. 2012; Candela et al. 2012) |
| Celiac disease | Altered composition, esp in small intestine. Fewer *lactobacilli* and *bifidobacteria* | GIT | (de Sousa Moraes et al. 2014; Kalliomaki et al. 2012) |
| Diabetes | Reduced *Bifidobacterium* spp. and *F. prausnitzii* | Systemic | (Furet et al. 2010; Wu et al. 2010) |
| Obesity | Increase in ratio of Firmicutes to Bacteroidetes | Systemic | (Ley et al. 2006; Turnbaugh et al. 2008) |
| Autism | Increased *Sutterella* spp., decreased *A. muciniphila* and *Bifidobacterium* spp. | Brain | (Wang et al. 2011; Williams et al. 2012) |
| Atherosclerosis [1] | Involvement of *Veillonella* spp., *Streptococcus* spp. and *Prevotella* enterotype | Arteries | (Koeth et al. 2013; Koren et al. 2011) |
| Depression and anxiety [1] | Changes in gut microbiota as a whole and decreased *Bifidobacterium* spp. | Brain | (Desbonnet et al. 2008; Neufeld et al. 2011) |
| Infant colic [1] | Increased Proteobacteria and reduced *bifidobacteria* and *lactobacilli* | GIT | (de Weerth et al. 2013; Savino et al. 2007) |
| Multiple sclerosis [1] | Changes in gut microbiota as a whole and presence of *Clostridium perfringens* Type B | Brain | (Lee et al. 2011; Rumah et al. 2013) |
| Parkinson's disease [1] | Decreased Prevotellaceae and increased *Clostridium* spp. | Brain | (Murata et al. 2013; Scheperjans et al. 2014) |
| Rheumatoid arthritis [1] | Changes in gut microbiota as a whole and decreased *Bacteroides* spp. | Systemic | (Abdollahi-Roodsaz et al. 2008; Vaahtovuo et al. 2008) |

[1] Preliminary evidence for link between colonic microbiota and these disorders.
GIT, gastrointestinal tract.
Table modified from de Vos & de Vos 2012.

Inflammation of the digestive tract may be associated with various conditions including atrophic glossitis, angular cheilitis, orofacial granulomatosis, esophagitis, gastritis, including atrophic gastritis, pyloric stenosis, colitis, ileitis, Crohn's disease, coeliac disease, inflammatory bowel disease, irritable bowel syndrome, lesions, fissures, and various ulcers, including ulcers of the mouth, esophagus, stomach, and intestines, and specifically including ulcerative colitis. Inflammation may also be associated with deleterious organisms, such as bacterial, protozoan, and/or viral organisms, including the groups/organisms of *Enterobacteriaceae, Pasteurellaceae, Veillonellaceae, Fusobacteriaceae, Proteobacteria, Campylobacter, Shigella, Yersinia, Listeria, Salmonella, Escherichia coli, Staphylococcus aureus, Clostridium*

*difficile, Helicobacter pylori, Mycobacterium avium, Enterococcus faecalis, Fusobacterium varium, Giardia, Entamoeba histolytica*, rotavirus, norovirus, adenovirus, astrovirus, and measles virus. In certain circumstances, inflammation may result from injury, medication, or surgery.

The gold kiwifruit compositions of the invention find use for treating or preventing gastrointestinal inflammation, constipation, bowel irregularity, microbiota imbalance, irritable bowel syndrome, inflammatory bowel disease, or other conditions described herein. As exemplary dosages, the compositions may be administered from 250 to 2500 mg; 500 to 5000 mg; 1000 to 4000 mg; or from 1500 to 4500 mg; or from 2000 to 3000 mg; or at about 250 mg, about 500 mg, about 600 mg, about 800 mg, about 1000 mg, about 1200 mg, about 1500 mg, about 1700 mg, about 1800 mg, about 2000 mg, about 2200 mg, about 2300 mg, about 2400 mg, about 2500 mg, about 2600 mg, about 2700 mg, about 2800, about 2900, about 3000 mg, about 3200, about 3500, about 3600 mg, about 4000 mg, about 4200 mg, about 4800 mg, about 5000 mg, about 5400 mg, about 6000 mg, or about 6600 mg, of gold kiwifruit powder per day, or equivalent dosage if a liquid form is used. Administration may be carried out once daily, twice daily, or three times daily. Administration may be made with food, or before a meal. The appropriate dosage and dosage form will be readily determined by a person of skill in the art.

Various routes of administration may be used for the gold kiwifruit compositions of the invention, including enteral administration, oral administration, and rectal administration. Oral administration may be by tablet, capsule, sachet, drops, elixir, linctus, solution, emulsion, suspension, draught, puree, paste, syrup, gel, jelly, tonic, or other known means. Enteral administration may be by duodenal tubing or gastric tubing, including nasogastric tubing. Rectal administration may be by enema, suppository, or other suitable means. Different means of administration are known in the art and may be utilised by a skilled person. The compositions of the invention are not limited to a particular form for administration.

In particular aspects, the compositions of the invention may be co-administered with one or more probiotic organisms. For example, the gold kiwifruit composition may be formulated as a combined dosage form with one or more probiotics. Alternatively, the gold kiwifruit composition may be administered as a separate dosage form along with one or more probiotics. Exemplary probiotic organisms include but are not limited to: *Bacillus coagulans*, e.g., GBI-30 and 6086 strains; *Bifidobacterium longum*, e.g., subsp. *infantis* 35624; *Lactobacillus acidophilus*, e.g., NCFM and CL1285 strains; *Lactobacillus paracasei*, e.g., St11 and NCC2461 strains; *Lactobacillus johnsonii*, e.g., La1 and NCC533 strains; *Lactobacillus* LC1; *Lactobacillus plantarum*, e.g., 299v and HEAL 9 strains; *Lactobacillus reuteri*, e.g., ATCC 55730, SD2112, Protectis (DSM 17938, daughter strain of ATCC 55730), Prodentis (DSM 17938/ATCC 55730 and ATCC PTA 5289 in combination), and RC-14® strains; *Saccharonmyces boulardii; Lactobacillus rhamnosus* e.g., a GR-1® strain; *Lactobacillus casei*, e.g., a LBC80R strain; *Lactobacillus bulgaricus; Streptococcus thermophilus*; and *Lactobacillus bifidus*. Other organisms that may be useful as probiotics include *Faecalibacterium* strains, including *Faecalibacterium prausnitzii*, and also *Bacteroidaceae* strains such as *Bacteriodes fragilis*.

In other aspects, the gold kiwifruit compositions of the invention may be co-administered with one or more prebiotic agents, e.g., as a combined dosage form or as separate dosage forms. As have been previously identified, prebiotic agents are comprised of non-digestible fibre or fermentable compounds that pass through the upper part of the digestive tract and stimulate the growth and/or activity of beneficial organisms that colonise the large intestine by acting as substrate for them.

These agents may be short-chain, long-chain, or full-spectrum prebiotics. Short-chain prebiotics include 2 to 8 links per saccharide molecule. Long-chain prebiotics include 9 to more than 60 links per saccharide molecule. Full-spectrum prebiotics include a full range of molecular link-lengths from 2 to more than 60 links per saccharide molecule. Exemplary prebiotic agents include but are not limited to: oligofructose, inulin, oligofructose-enriched inulin, fructo-oligosaccharides, xylooligosaccharides, polydextrose, galacto-oligosaccharides, trans-galacto-oligosaccharides, mannan oligosaccharides, lactulose, tagatose, and starch.

Based on the results shown herein, it is believed that the polyphenols present in the disclosed compositions may be acting as prebiotic agents. Thus, it may be useful to add one or more phenolic compounds to the compositions of the invention, to supplement the prebiotic activity therein. Exemplary compounds include but are not limited to: phenolic derivatives such as phenolic acid, and flavonoids such as lignins, proanthocyanidins, anthocyanins, anthocyanidins, isoflavones, catechins, tannins, quercetin, naringenin, and hesperidin. Particularly encompassed are phenolic compounds extracted from one or more of: tea, cocoa, wine, soybeans, feijoa, citrus fruits, apples, grapes, berries, and kiwifruit, particularly gold kiwifruit, including Hort16 and Gold3. Specific phenolics from Gold3 gold kiwifruit include but are not limited to: catechin, chlorogenic acid, E-caffeoyl-3-glucoside, E-caffcoyl-4-glucoside, epicatechin, neochlorogenic acid, phlorizin, procyanidin B1 and B2, quercetin rhamnoside, and quercetin rutinoside.

In further aspects, the compositions of the invention may be co-administered with one or more synbiotic (combined prebiotic and probiotic) agents. For example, the gold kiwifruit powder may be formulated as a combined dosage form with one or more synbiotics. Alternatively, the gold kiwifruit may be administered as a separate dosage form along with one or more synbiotics. As examples, *Bifidobacteria* or *Lactobacilli* may be combined with fructo-oligosaccharides or insulins or galactooligosaccharides. Particular synbiotic combinations include but are not limited to: *Bifidobacteria* and fructo-oligosaccharides; *Lactobacillus rhamnosus*, e.g., a GG strain, and insulins.

As additional aspects, the compositions of the invention may be co-administered with fibre and/or digestive enzymes. For example, the gold kiwifruit powder may be formulated as a combined dosage form with one or more compositions comprising fibre and/or digestive enzymes. Alternatively, the gold kiwifruit powder may be formulated as administered as a separate dosage form with one or more compositions comprising fibre and/or digestive enzymes. Exemplary fibre compositions include soluble and/or insoluble fibre compositions, for example, compositions including one or more of wheat dextrin, calcium polycarbophil, psyllium, inulin, methylcellulose, glucomannan, flax, flaxseed, wheatgrass, acacia senegal, and rhubarb. Exemplary digestive enzymes include, but are not limited to: actinidin, protease, lipase, amylase, cellulose, pancreatin, pepsin, bromelain, papain, trypsin, and chymotrypsin. Combinations of digestive enzymes may also be used, for example, combinations of protease, lipase, and amylase, including those with or without added actinidin.

In further aspects, the gold kiwifruit compositions of the invention may be co-administered with one or more anti-inflammatory agents and/or anti-microbial agents. Of particular interest is use of the composition of the invention as a prebiotic supplement during and/or following antibiotic treatment. For example, the gold kiwifruit powder may be formulated as a combined dosage form with one or more anti-inflammatory/anti-microbial agents. Alternatively, the gold kiwifruit may be administered as a separate dosage form along with one or more anti-inflammatory/anti-microbial agents. Exemplary anti-inflammatory/anti-microbial agents include but are not limited to aminosalicylates, for example, mesalazine (e.g., Pentasa®) and sulphasalazine (e.g., Salazopyrin®), corticosteroids, for example, budesonide (e.g., Entocort®) and hydrocortisone acetate (e.g., Colifoam®), and include also azathioprine (e.g., Azasan®, Imuran®), mercaptopurine (e.g., Purinethol®, Purixan™), cyclosporine (e.g., Gengraf®, Neoral®, Sandimmune®), infliximab (e.g., Remicade®), adalimumab (e.g., Humira®), golimumab (e.g., Simponi®), methotrexate (e.g., Rheumatrex™, Methoblastin™), natalizumab (e.g., Tysabri™), vedolizumab (e.g., Entyvio™), ustekinumab (e.g., Stelara®), and antibiotics including metronidazole (e.g., Flagyl®) and ciprofloxacin (e.g., Cipro®, Ciplox™).

EXAMPLES

The examples described herein are provided for the purpose of illustrating specific embodiments of the invention and are not intended to limit the invention in any way.

Example 1

Preparation of Kiwifruit Powder

Frozen gold kiwifruit puree (Frozen Gold Kiwifruit Puree Single Strength (Seed Out)) was obtained from Kiwifruit Processing Company Ltd, Tauranga, New Zealand. The puree was made from 100% New Zealand gold kiwifruit (*Actinidia chinensis* G3) grown to Zespri® export standards, and hand graded. The puree was produced by manufacturing processes to remove the skin and seeds to leave a smooth and rich puree.

The product specification of the frozen gold kiwifruit puree follows:

The colour is kiwifruit gold, with some variation in colour being normal. The taste is typical of ripe gold kiwifruit. The texture is smooth and seedless. The puree has nil quantities of rotten or fermented fruit, or foreign bodies, and contains no detectable *E coli*. The Brix value is 16 to 21°. The viscosity (at 12.5° Brix, 20° C.) is approximately 12.0, but can vary when fruit is held across a season. The pH is 3.2 to 3.8. The sieve size is <1 mm. The product is kept frozen at −18° C. until use.

In addition, frozen green kiwifruit puree (Frozen Green Kiwifruit Puree Single Strength (Seed Out)) was obtained from Kiwifruit Processing Company Ltd, Tauranga, New Zealand. The puree was made from 100% New Zealand green (*Actinidia deliciosa*, Hayward variety) kiwifruit grown to Zespri® export standards, and hand graded. The puree was produced by manufacturing processes to remove the skin and seeds to leave a smooth and rich puree.

The product specification of the frozen green kiwifruit puree follows:

The colour is kiwifruit green, with some variation in colour being normal. The taste is typical of ripe green kiwifruit. The texture is smooth and seedless. The puree has nil quantities of rotten or fermented fruit, or foreign bodies, and contains no detectable *E. coli*. The Brix value is 13 to 18°. The viscosity (at 12.5° Brix, 20° C.) is approximately 12.0, but can vary when fruit is held across a season. The pH is 3.2 to 3.8. The sieve size is <1 mm. The product is kept frozen at −18° C. until use.

The process for obtaining kiwifruit powder was as follows:

1) Frozen Gold3 puree was purchased from Kiwifruit Processing Company Ltd, Tauranga, New Zealand.

2) The frozen puree was lyophilised (freeze-dried). The lyophilisation process was typically performed for up to about 48 hours, at temperatures not exceeding 70° C. The resulting dried material was then milled through a US 20 mesh to produce a free-flowing powder.

3) The same method was used to obtain green kiwifruit powder.

Example 2

Polyphenol Measurement for Kiwifruit Powders

The polyphenol profiles of green and gold kiwifruit powders were tested. Lyophilised (freeze-dried) green (Hayward) and gold (Gold3) kiwifruit powders were prepared in accordance with Example 1.

The powders were digested using an in vitro upper gastro-intestinal model as described in Monro et al. 2010. Briefly, 20 mL of water and 5 mL 20% saline solution were added to 5 g of samples at pH 2.5 before vortexing. Then 1 mL of 1% pepsin in 0.05 M hydrochloric acid was added, followed by 30 minute incubation at 37° C. with slow constant mixing (220 rpm), The samples were adjusted to pH 6.5, followed by the addition of 5 mL of 2.5% bile extract obtained from Sigma Aldrich®, and 1 mL of 5% pancreatin in 3% sodium chloride (NaCl).

The samples were then vortexed and incubated at 37° C. with slow constant mixing (220 rpm) for 2 hours. The digested samples were then transferred to dialysis bags (500 Da MWCO, obtained from Thermofisher Scientific) and dialysed in 10 mM NaCl at 4° C. overnight, followed by a change in dialysis fluid and a further 2 hours at 2° C., representing absorption in the small intestine. The samples were stored at −80° C. then freeze dried.

Pre and post-digested samples of the freeze dried green and gold powders (100 mg) were extracted with 5 mL ethanol/water/formic acid (80:20:1). The extraction mixture was sonicated for 30 minutes then stored overnight. Samples were centrifuged at full speed to remove particulates and diluted 2× prior to liquid chromatography—mass spectrometry (LC-MS) analysis. Details are provided in Table 2, below.

TABLE 2

| LC-MS analysts for pre- and post-digested kiwifruit powders | |
|---|---|
| LCMS | Dionex Ultimate ® 3000 Rapid Separation LC with micrOTOF QII mass spectrometer |
| Column | Zorbax ™ SB-C18 2.1 m × 100 mm, 1.8 µm |
| Mobile phase flow | 350 µL/min |
| Solvents | A = 100% acetonitrile |
| | B = 0.2% formic acid |
| Gradient | 10% A, 90% B, 0-0.5 min |
| | Linear to 50% A, 50% B, 0.5-18 min |
| | Linear to 100% A, 18-30 min |
| | Held at 100% A for 30-40 min |
| | Linear to 10% A, 90% B, 40-40.2 min |

TABLE 2-continued

LC-MS analysts for pre- and post-digested kiwifruit powders

| | |
|---|---|
| Injection volume | 2 µL |
| MS parameters | Drying $N_2$ temperature: 200° C. |
| | Drying $N_2$ flow: 8 L/min |
| | Nebulizer $N_2$: 1.5 bar |
| | Mass range: 100-1500 Da |
| | Acquisition rate: 2 scan/s |

Compound concentrations were calculated using calibration curves from authentic standards.

As shown in FIG. 1, digested Gold3 powder (simulated upper gastrointestinal digestion) has an altered polyphenol profile compared to pre-digestion (FIG. 1); however, the overall phenolic content is retained. In particular, 269 µg/g polyphenol content pre-digestion versus 264 µg/g phenol content post-digestion was observed for the Gold3 powder (FIG. 1; combined total for phenolic compounds tested). Green kiwifruit powder also shows an altered polyphenol profile post-digestion, but the overall content is reduced by digestion (FIG. 1). For the green kiwifruit powder, the overall polyphenol content was 258 µg/g pre-digestion versus 153 µg/g post-digestion (FIG. 1; combined total for phenolic compounds tested).

Example 3

Microbial High-throughput Assays for Kiwifruit Powders

Gold3 gold kiwifruit powder was obtained from a paste formula (prepared by Cedenco Foods, New Zealand), which was drum-dried with pea starch (14.28:1 wet weight in). A sample (5 g) of the powder was digested in vitro using an upper gastro-intestinal model as described in Example 2.

The digested material was then solubilised in either water or dimethyl sulfoxide (DMSO) to a uniform concentration of 100 mg/mL. The samples were then diluted 100-fold with sterile deionised water to reduce the DMSO to a manageable concentration to prevent bacterial lysis. The water and DMSO 'extracts' were added to microbial high-throughput assay wells to a final concentration of 1.0 mg/mL The organisms used in the study included probiotic *Escherichia coli* Nissle 1917, *Lactobacillus rhamnosus* HN001 (DR20), *Bifidobacterium lactis* HN019 (DR10), and pathogenic *Salmonella enterica* serovar *Typhimurium* ATCC 1772 and *Staphylococcus aureus* ATCC 25932.

A ninety-six-well microplate growth bioassay measuring optical density (OD) as described in Rosendale et al. 2008, was used for this work. The change in growth (Δgrowth) was calculated and used to represent the magnitude of effect. This was calculated by converting the OD to a percentage of the control OD, then subtracting 100, effectively normalizing the control growth to a baseline value of zero.

One strain of bacterium per microplate was used and each extract was analysed in quadruplicate per microplate at a range of concentrations (0, 0.0124, 0.037, 0.111, 0.333, 1 mg/mL). The microplates were inoculated with an equal volume (50 µL) of bacterial inoculum and the OD measured immediately at a wavelength of 595 nm with a plate reader (FLUOstar Optima®) to determine the blank/zero growth value. The microplates were incubated at 37° C. for 24 hours, then the OD determined to measure the growth of the cultures.

Figure 2:
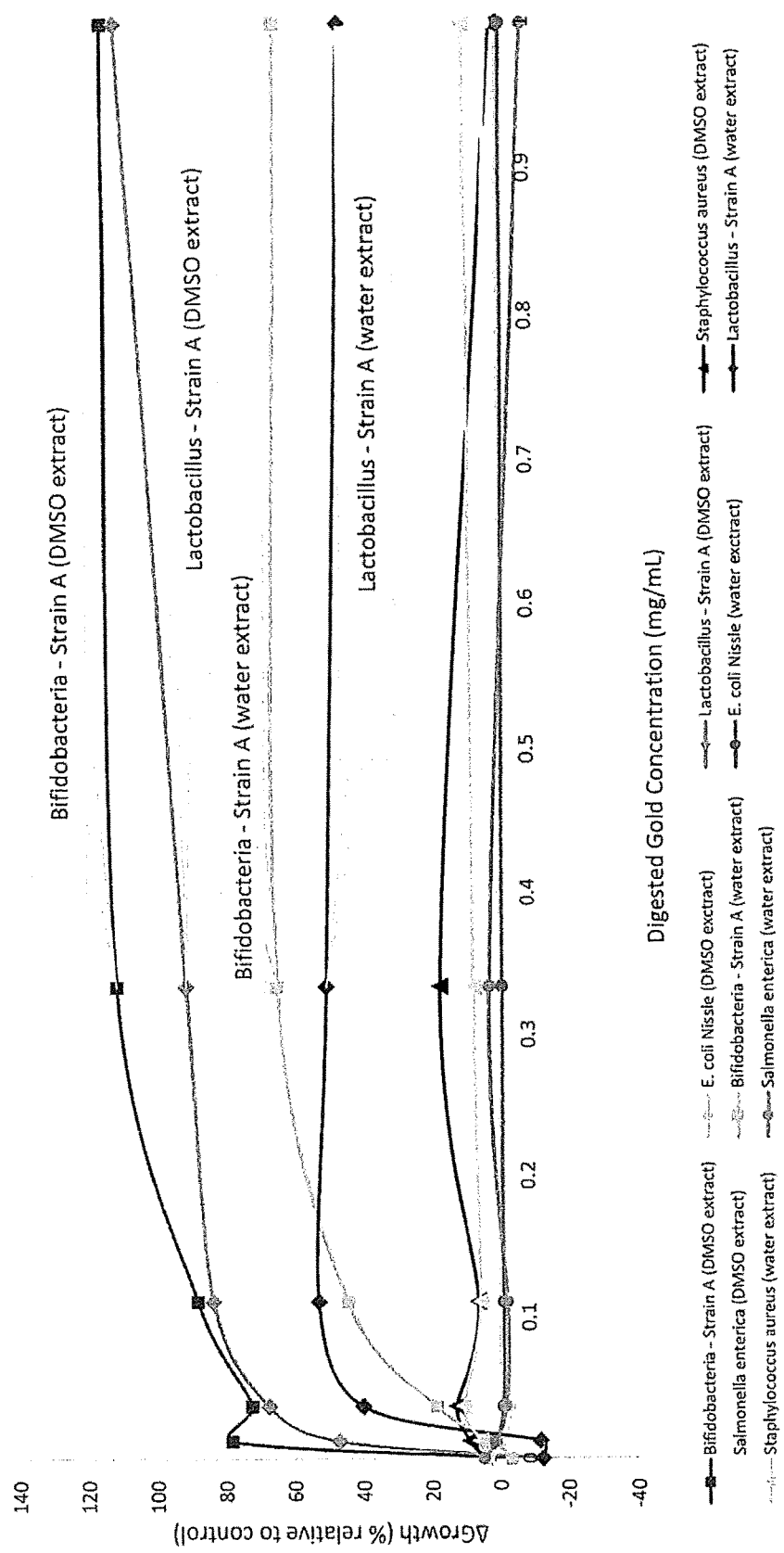
FIG. 2: Change in growth of bacteria strains when exposed to water and DMSO extracts of digested gold (Gold3) kiwifruit powder.

The results showed that the Gold3 gold powder supported the growth of *Bifidobacteria* and *Lactobacillus* strains, whilst not affecting a significant change in the numbers of pathogenic bacteria, versus the control (FIG. 2).

Example 4

Mixed Fermentation Model for Testing Kiwifruit Powders

Gold3 gold kiwifruit powder was obtained from a paste formula (prepared by Cedenco Foods, New Zealand), which was drum-dried with pea starch (14.28:1 wet weight in). A sample (5 g) of powder was digested in accordance with Example 2. The digested sample was solubilised in water to a final concentration of 10 mg/mL.

Freshly voided faecal samples were collected from three healthy human volunteers. The digested gold powder was incubated in a test tube inoculated with mixed microbiota from a single faecal donor, repeated for each of the three donors. Hungate tubes containing pre-reduced fermentation media (9 mL) under carbon dioxide were supplemented with 1 mL of the sample or control and inoculated with 1 mL of a 10% (w/v) faecal slurry. The tubes were incubated at 37° C. with gentle (150 rpm) orbital shaking. Subsamples were periodically (0, 5, 10, 24, 48 hrs) removed with a syringe and 22 gauge needle through the rubber septum to prevent exposure of the sample to the atmosphere.

The samples removed from the fermentation tubes were collected into 1.5 mL Eppendorf Tubes® and centrifuged immediately at 13,000×g for 5 minutes. The cell—and particle-free supernatants were collected into fresh Eppendorf Tubes® and frozen at −80° C. until required.

The supernatant was defrosted and diluted 1:4 in 0.01 M phosphate buffered saline with 2-ethylbutyrate (5 mM final concentration) as an internal standard. The sample was then centrifuged at 3,000×g for 5 minutes at 4° C. The supernatant (0.25 mL) was acidified with concentrated hydrochloric acid (0.125 mL), diethyl ether (0.5 mL) was added, then vortexed and centrifuged at 10,000×g for 5 minutes (4° C.), The upper diethyl ether phase was collected, dried with magnesium sulphate, and derivatised with N-tert-butyldimethylsilyl-N-methyltrifluroroacetamide with 1% tert-butyldimethylchlorosilane by heating to 80° C. for 20 minutes.

The concentrations of the microbial organic acid metabolites in the fermentation samples were quantified by gas chromatography (GC) as per Table 3 below.

TABLE 3

GC analysis of organic acid metabolites

| | |
|---|---|
| GC | Shimazdu GC-17A with flame ionisation detector (FID) |
| Column | 10 m × 0.53 mm ID × 2.65 µm |
| Carrier gas | Helium |
| Flow rate | 37 mL/min |
| Pressure | 7 kPa, increasing to 15 kPa at 0.8 kPa/hr Hold for 4 min |
| Temperature programme | 70° C. increasing to 80° C. at 10° C./min Increase to 255° C. at 20° C./min Hold for 5 min |
| Injector and detector temperature | 260° C. |
| Injection volume | 1 µL, splitless |

Organic acid standard mixtures of known concentration were analysed alongside the samples and used to create standard curves with relative peak areas standardised to the 2-ethylbutyrate response. Results were expressed as µmol organic acid/mL fermenta.

Figure 3:
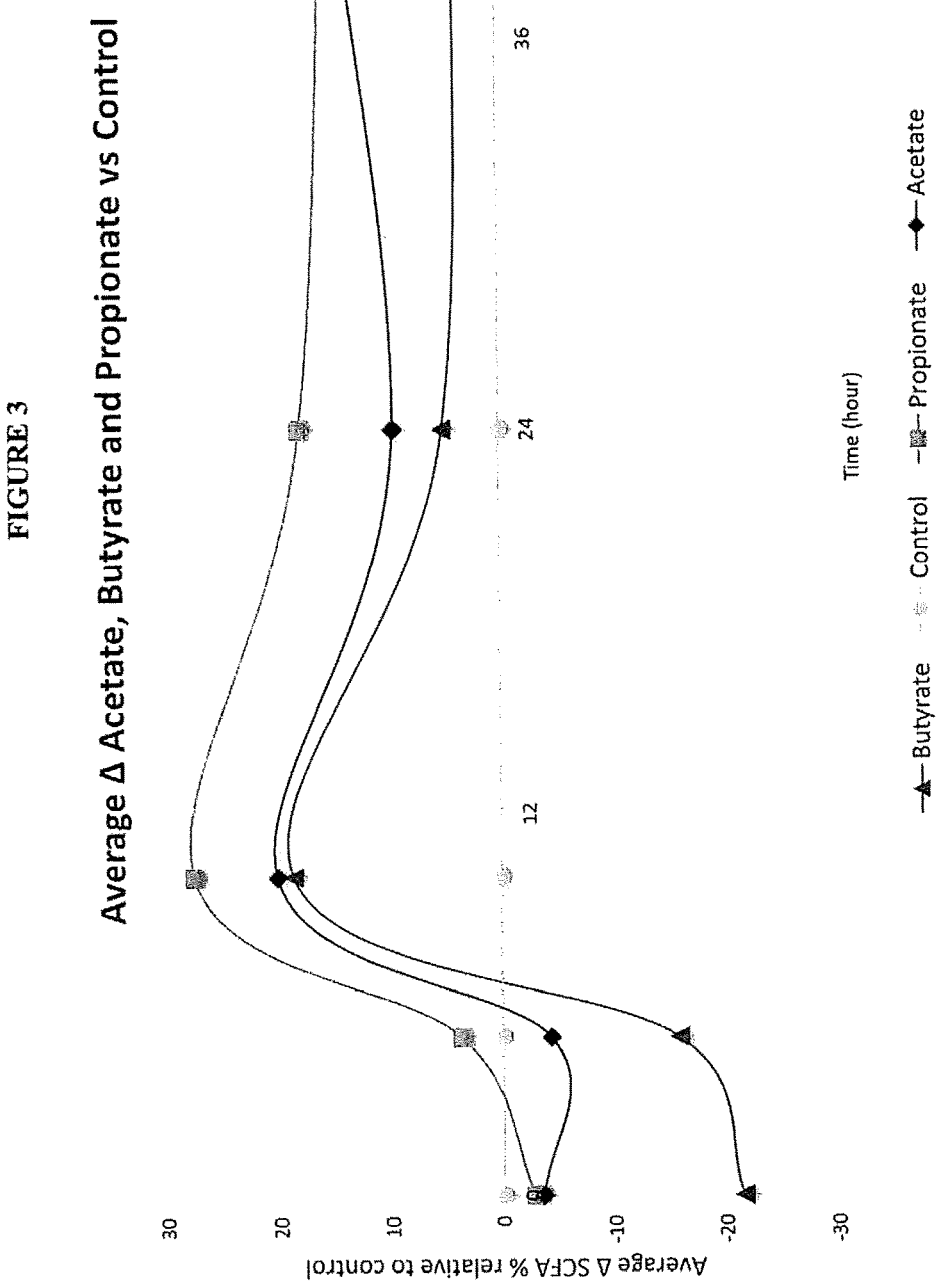
FIG. 3: Effect of gold (Gold3) kiwifruit powder on short chain fatty acid production in vitro using a mixed fermentation model.

As shown in FIG. 3, the presence of the Gold3 gold kiwifruit powder promoted an increase in organic acid production, particularly after the first 12 hours of exposure. Given the increase observed, this indicates that the non-digestible fermentable components (carbohydrates and polyphenols) in the gold powder were broken down and used as a growth and energy-generating substrate. This is consistent with action as a prebiotic.

Example 5

Clinical Trial to Test Gold3 Gold Kiwifruit Powder for Improving Regularity

Clinical Protocol Overview

Figure 4:
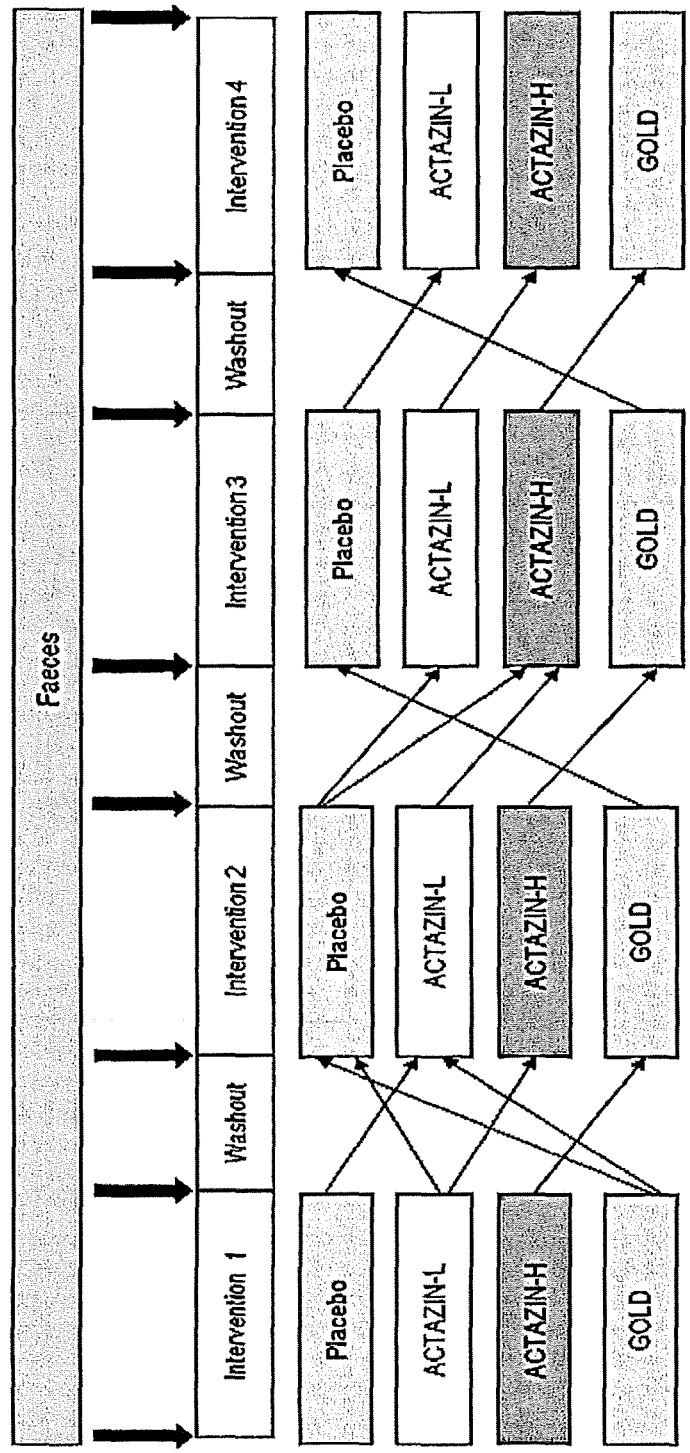
FIG. 4: Schematic of trial treatments, washouts, and sampling points.

The study was designed as a randomised double-blind placebo controlled cross-over trial with participants consuming four different interventions for 4 weeks each, with a 2 week washout between each intervention. A schematic view of the trial design is shown in FIG. 4.

Clinical Trial Participants

Two groups of participants were recruited through newspaper and radio advertisements, community, local district health board, Canterbury University (Christchurch, New Zealand), Lincoln University (Lincoln, New Zealand), newsletters, posters in doctors' general practice surgeries and through our existing database of prior participants.

Twenty-nine total participants were recruited from fifty-one total volunteers. The participants were split into two cohorts: cohort 1 ("healthy"): those participants without clinical symptoms of constipation; and cohort 2 ("functionally constipated"): those participants classified as having C3 functional constipation based on the Rome III criteria.

Rome III Criteria:
1) Must include two or more of the following: a) straining during at least 25% of defecations; b) lumpy or hard stools in at least 25% defecations; c) sensation of anorectal obstruction or blockage for at least 25% defecations; d) sensation of incomplete evacuation for at least 25% defecations; e) manual manoeuvres to facilitate at least 25% defecations; f) three or fewer defecations per week;
2) Loose stools are rarely present without the use of laxatives; and
3) Insufficient criteria for irritable bowel syndrome.

Inclusion criteria were: age 18-60; BMI limits between 19 and 30 k/m$^2$; fasting blood glucose under 5.6 mmol/L; subjects were required to be willing to maintain his or her habitual food and beverage intake (other than substitution of study food for similar products) and physical activity pattern throughout the study period; subjects were asked to exclude high fibre supplements such as Metamucil®, Benefibre® and Phloe™ as well as refraining from eating fresh kiwifruit for the study period; participants were asked to avoid overseas travel for the period of the study due to the impact this may have on diet.

Exclusion criteria were: presence of gastrointestinal alarm symptoms (including blood in stools, frequent diarrhoea, unremitting abdominal pain); dieters or people who are following vegan, raw food diets or very high fibre diets; gastroparesis or lactose intolerance; surgery for weight loss (lapband or gastric bypass); pregnant women; clinically significant renal, hepatic, endocrine, cardiac, pulmonary, pancreatic, neurological, hematologic or biliary disorders; and known allergy or sensitivity to kiwifruit.

The "healthy" group was comprised of participants that were without clinical symptoms of constipation. The "functionally constipated" (FC) group was selected based on Rome III criteria (Drossman 2006) as having C3 functional constipation. Twenty participants (2 male and 18 female) were recruited into the healthy group. The average age was 38 years (range 23-56 years) and the average body mass index was 23 kg/m$^2$ (range 19-29 kg/m$^2$). Nine participants (1 male and 8 female) were recruited into the FC group. The average age was 44 years (range 38-54 years) and the average body mass index was 25 kg/m$^2$ (range 21-29 kg/m$^2$). See also Table 6, further below.

Nineteen of the twenty participants in the healthy group completed the study. One female participant withdrew due to personal reasons. All nine participants in the FC group completed the study. The order in which participants were allocated their intervention was randomised by a biostatistician using a Williams Latin Square design and computer generated random numbers. Upon completion of the analyses, the study was unblinded to reveal the intervention order. Ethical approval was obtained from the New Zealand Human Disability and Ethics Committee under expedited review (Application number 12/STH/72/AM01), and was registered with the Australia New Zealand Clinical Trials Registry. Registration number ACTRN: 12612001270808.

Clinical Testing Methods

The interventions were delivered in 4×600 mg capsules supplied by Anagenix Limited (Wellington, New Zealand) prepared to look identical to preserve intervention blinding (Table 4).

TABLE 4

Description of intervention composition

| Intervention | Treatment | Dose | Delivery - capsules/day |
|---|---|---|---|
| ACTAZIN ™ L | Green Kiwifruit Powder | 600 mg | 1 × ACTAZIN ™ + 3 × Placebo |
| ACTAZIN ™ H | Green Kiwifruit Powder | 2400 mg | 4 × ACTAZIN ™ |
| GOLD | Gold (G3) Kiwifruit Powder | 2400 mg | 4 × GOLD |
| Placebo | Isomalt coloured green (E102, E142) | 2400 mg | 4 × Placebo |

TABLE 5

Nutritional information of the interventions used, ACTAZIN ™ and GOLD

| Nutrition information (per 100 g) | GOLD | ACTAZIN ™ |
|---|---|---|
| Energy, kJ | 1420 | 1435 |
| Protein, g | 3.9 | 3.4 |
| Fat, total, g | 1.8 | 3.0 |
| Saturated, g | 0.34 | 0.75 |
| Unsaturated, g | 1.4 | 2.4 |
| Monounsaturated, g | <0.10 | 0.53 |
| Polyunsaturated, g | 1.4 | 1.8 |
| Carbohydrate, g | 71 | 67 |
| Sugars, total, g | 58 | 46 |
| Sucrose, g | <0.05 | <0.05 |
| Glucose, g | 27 | 21 |
| Fructose, g | 31 | 25 |
| Lactose, g | <0.05 | <0.05 |
| Maltose, g | <0.05 | <0.05 |
| Dietary fibre, g | 12 | 16 |
| Sodium, mg | 18 | 13 |
| Total polyphenols, mg GAE | 1100 | 900 |
| Actinidin, AUs/g | 9100 | 40700 |

All participants consumed four different intervention combinations: Placebo (isomalt coloured green) (2400 mg/day), ACTAZIN™ L (600 mg/day), ACTAZIN™ H (2400 mg/day) and GOLD (2400 mg/day) for 28 d each intervention, with a 14 d washout period between each treatment phase.

ACTAZIN™ L (low dose, green kiwifruit) and ACTAZIN™ H (high dose, green kiwifruit) were formulated from cold-processed *Actinidia deliciosa* 'Hayward' green kiwifruit and GOLD was formulated from cold-processed *Actinidia chinensis* 'Zesy002' Gold3 gold-fleshed kiwifruit, See Example 1.

At the beginning and end of each 4 week intervention period, participants were asked to provide a faecal sample. The washout period of 2 weeks was chosen to allow sufficient time to return bowel habits to baseline for the parameters measured (microbial ecology, microbial metabolites).

At the beginning and end of each intervention period, participants were also asked to provide a faecal sample and to complete the Birmingham Irritable Bowel Syndrome (IBS) symptom questionnaire (Johnston et al. 2010) as well as an IBS specific quality of life questionnaire (Patrick et al. 1998) relating to wellness.

For each day from baseline until the end of the study, the participants recorded various parameters in the daily diaries provided. These parameters included: 1) number of bowel movements; 2) incomplete and assisted bowel movements; 3) straining; 4) stool form as determined by the Bristol stool scale; 5) bloating; 6) flatulence; 7) abdominal pain; 8) laxative use.

Data were analysed using analysis of variance (ANOVA) in GenStat (v.16, 2013, VSNi Ltd., Hemel Hempstead, UK). Data from the two cohorts were analysed separately. Results from each observation period were analysed as a complete block design, with participant and participant×phase as blocks, and phase (1, 2, 3, or 4) and intervention (including washout) as factors. Mean washout data were used as baseline for the purposes of the statistical analysis. Residuals were inspected to ensure the assumptions of ANOVA were met; where necessary data were log-transformed to stabilise variance.

Post hoc subgroup analysis was conducted on the healthy cohort using Cochran's Q test to compare those participants responding to each intervention (i.e., with a rise of at least one bowel movement per week over the preceding washout period). Participants were then classified as either responder (showed a response to at least one of the non-placebo interventions) or non-responder; data from the responders subgroup (14 of 19 participants (74%)) was analysed using ANOVA.

The primary study outcome was a significant increase in stool frequency.

Example 6

Results of Treatment on Improving Regularity

The demographics of the participants are shown in Table 6. Compliance within the healthy and functionally constipated cohorts was 98%±9 and 99%±8, respectively.

TABLE 6

Demographics of the study participants

| Baseline characteristics | Healthy | Functionally constipated |
|---|---|---|
| N | 20 | 9 |
| Male | 2 | 1 |
| Female | 18 | 8 |
| Age in years (Mean ± SD) | 38 ± 11 | 44 ± 6 |
| Age (Range) | 23-56 | 38-54 |
| Weight in kg (Mean ± SD) | 68 ± 13 | 67 ± 8 |
| Weight (Range) | 47-101 | 53-79 |
| BMI in kg/m² (Mean ± SD) | 23 ± 3 | 25 ± 2 |
| BMI (Range) | 19-29 | 21-29 |
| Compliance (%) | 98 ± 9 | 99 ± 8 |

BMI—Body Mass Index;
SD—Standard Deviation

The results of this study are summarized in Tables 7 and 8.

In the healthy cohort (n=19), significant differences between the interventions and washout were observed for the number of daily bowel movements (p=0.002), Bristol stool score (p=0.036), strain (p=0.044) and flatulence (p=0.007). The number of daily bowel movements for the ACTAZIN-H and GOLD interventions were significantly higher (p=0.014 and p=0.009, respectively) compared to washout, with an approximate increase of 0.8 bowel movements per week with each intervention. Table 7.

In the responder sub-group (n=14), consumption of ACTAZIN-L, ACTAZIN-H and GOLD resulted in a significant increase in daily bowel movements (p=0.005, p<0.001, and p=0.001, respectively) when compared to washout. Table 7.

Consumption of the interventions for 28 days was generally well tolerated with no serious adverse events reported, and no effects (p<0.05) on well-being parameters recorded in the daily questionnaires except for self-reported flatulence, which was higher in the healthy cohort ACTAZIN-H group (p=0.007). Table 7.

In the individuals with functional constipation (n=9), the dietary interventions did not significantly increase the frequency of bowel movements compared with the washout. Table 8. This was attributed to the small sample size of the study, which has limitations in its statistical power to detect significant differences in stool frequency. However, the functionally constipated group showed overall improvement in digestive parameters, and an abatement of other symptoms of constipation.

In the functionally constipated group, comprehensive improvement was seen in the Digestive Health Index. FIG. 5A. Eight out of nine of the functionally constipated participants showed improvement in gastrointestinal health parameters, as calculated from the sum of the average change from washout for: straining, incomplete evacuation, manual manoeuvres, bloating, wind, laxative use, and pain. FIG. 5A. Scoring for each parameter was obtained from the participants' daily diaries.

An increase of greater than one bowel movement per week in a symptomatic population is considered a clinically meaningful magnitude of effect (Food and Drug Administration 2012), and would potentially improve the symptoms of sufferers of mild or occasional constipation. ACTAZIN™ and GOLD, which are derived from green (Hayward) and gold (Gold3) kiwifruit, have demonstrated this degree of efficacy in a healthy population. In particular, an increase of approximately 1.5 bowel movements per week each was observed in the responder sub-group of healthy cohorts compared to washout.

In summary, this study showed that ACTAZIN™ and GOLD improved regularity and laxation without affecting the stool form for the healthy cohort. For the functionally constipated group, GOLD improved overall digestive parameters and relieved key symptoms of constipation, including straining, incomplete evacuation, manual manoeuvres, bloating, wind, laxative use, and pain.

TABLE 7

Analysis of variance results for daily diaries, Birmingham IBS symptoms, and IBS-quality of life questionnaires in the healthy cohort

| Healthy cohort (n = 19) | Means | | | | | Analysis of variance P-value Washout versus average of treatments (1 df) |
|---|---|---|---|---|---|---|
| | Placebo | ACTAZIN-L | ACTAZIN-H | GOLD | Washout | |
| *Daily diaries questionnaire* | | | | | | |
| Number of daily bowel movements | 1.12 | 1.16 | 1.19 | 1.20 | 1.08 | 0.002 |
| Bristol stool scale | 3.61 | 3.52 | 3.61 | 3.62 | 3.42 | 0.036 |
| Strain | 0.22 | 0.22 | 0.24 | 0.22 | 0.28 | 0.044 |
| Incomplete evacuation | 0.14 | 0.14 | 0.13 | 0.17 | 0.18 | 0.137 |
| Bloating | 0.17 | 0.15 | 0.13 | 0.16 | 0.14 | 0.497 |
| Flatulence | 0.60 | 0.64 | 0.67 | 0.64 | 0.58 | 0.007 |
| Manual manoeuvres | 0.00 | 0.02 | 0.01 | 0.02 | 0.01 | 0.860 |
| Laxatives | 0.01 | 0.00 | 0.00 | 0.00 | 0.00 | 0.786 |
| Abdominal pain | 0.12 | 0.11 | 0.05 | 0.08 | 0.08 | 0.339 |
| *Birmingham IBS symptom questionnaire* | | | | | | |
| Constipation | 1.73 | 1.94 | 1.45 | 2.06 | 2.23 | 0.093 |
| Diarrhoea | 1.22 | 1.32 | 1.43 | 1.28 | 1.11 | 0.222 |
| Pain | 1.57 | 1.11 | 0.69 | 0.82 | 1.10 | 0.707 |
| *IBS - Quality of life questionnaire* | | | | | | |
| Dysphoria | 8.61 | 8.38 | 8.33 | 8.27 | 8.38 | 0.891 |
| Interference with activity | 7.39 | 7.68 | 7.93 | 7.42 | 7.65 | 0.743 |
| Body Image | 4.41 | 4.67 | 4.45 | 4.35 | 4.69 | 0.114 |
| Health worry | 3.61 | 3.46 | 3.60 | 3.35 | 3.67 | 0.067 |
| Food avoidance | 3.87 | 4.25 | 4.42 | 4.25 | 4.22 | 0.855 |
| Social Reaction | 4.26 | 4.27 | 4.33 | 4.16 | 4.35 | 0.074 |
| Sexual | 2 | 2 | 2 | 2 | 2 | — |
| Relationships | 3.09 | 3.27 | 3.43 | 3.05 | 3.24 | 0.676 |
| *Responders (n = 14)* | | | | | | |
| Number of daily bowel movements | 1.27 | 1.35 | 1.39 | 1.38 | 1.18 | <0.001 |

| Healthy cohort (n = 19) | Analysis of variance P-value Treatment differences (3 df) | Post-hoc P-values Washout versus intervention | | | |
|---|---|---|---|---|---|
| | | Placebo | ACTAZIN-L | ACTAZIN-H | GOLD |
| *Daily diaries questionnaire* | | | | | |
| Number of daily bowel movements | 0.918 | 0.377 | 0.060 | 0.014 | 0.009 |
| Bristol stool scale | 0.806 | 0.134 | 0.421 | 0.138 | 0.113 |
| Strain | 0.349 | 0.157 | 0.150 | 0.363 | 0.166 |
| Incomplete evacuation | 0.432 | 0.310 | 0.306 | 0.174 | 0.699 |
| Bloating | 0.490 | 0.223 | 0.757 | 0.631 | 0.503 |
| Flatulence | 0.572 | 0.511 | 0.073 | 0.007 | 0.075 |
| Manual manoeuvres | 0.339 | 0.247 | 0.637 | 0.343 | 0.234 |
| Laxatives | 0.703 | 0.156 | 0.494 | 0.475 | 0.475 |
| Abdominal pain | 0.375 | 0.021 | 0.083 | 0.103 | 0.980 |
| *Birmingham IBS symptom questionnaire* | | | | | |
| Constipation | 0.243 | 0.218 | 0.471 | 0.058 | 0.672 |
| Diarrhoea | 0.881 | 0.691 | 0.428 | 0.209 | 0.514 |
| Pain | 0.100 | 0.037 | 0.957 | 0.069 | 0.202 |
| *IBS - Quality of life questionnaire* | | | | | |
| Dysphoria | 0.272 | 0.134 | 0.958 | 0.727 | 0.441 |
| Interference with activity | 0.604 | 0.186 | 0.858 | 0.133 | 0.235 |
| Body Image | 0.592 | 0.202 | 0.915 | 0.277 | 0.121 |
| Health worry | 0.907 | 0.646 | 0.138 | 0.607 | 0.030 |
| Food avoidance | 0.063 | 0.128 | 0.889 | 0.383 | 0.896 |

TABLE 7-continued

Analysis of variance results for daily diaries, Birmingham IBS symptoms, and IBS-quality of life questionnaires in the healthy cohort

| | | | | | |
|---|---|---|---|---|---|
| Social Reaction | 0.323 | 0.299 | 0.316 | 0.823 | 0.023 |
| Sexual Relationships | 0.058 | 0.149 | 0.788 | 0.064 | 0.068 |

Responders (n = 14)

| | | | | | |
|---|---|---|---|---|---|
| Number of daily bowel movements | 0.999 | 0.117 | 0.005 | <0.001 | 0.001 |

TABLE 8

Analysis of variance results for daily diaries, Birmingham IBS symptoms, and IBS-quality of life questionnaires in the FC cohort

| | | | | | | ANOVA p-values | |
|---|---|---|---|---|---|---|---|
| | Placebo | ACTAZIN-L | ACTAZIN-H | GOLD | Washout | Washout vs. average of interventions | Difference between interventions |
| Daily diaries questionnaire | | | | | | | |
| Number of daily bowel movements | 0.96 | 0.92 | 0.88 | 0.99 | 0.93 | 0.999 | 0.840 |
| Bristol stool scale | 3.00 | 2.93 | 2.82 | 2.92 | 2.78 | 0.210 | 0.215 |
| Strain | 0.55 | 0.43 | 0.38 | 0.41 | 0.49 | 0.321 | 0.527 |
| Incomplete evacuation | 0.52 | 0.40 | 0.41 | 0.39 | 0.41 | 0.720 | 0.671 |
| Bloating | 0.09 | 0.14 | 0.12 | 0.14 | 0.12 | 0.836 | 0.533 |
| Wind | 0.46 | 0.32 | 0.49 | 0.23 | 0.43 | 0.254 | 0.228 |
| Manual manoeuvres | 0.93 | 0.94 | 0.81 | 0.84 | 0.87 | 0.609 | 0.115 |
| Laxatives | 0.01 | 0.01 | 0.01 | 0.02 | 0.01 | 0.615 | 0.967 |
| Abdominal pain | 0.27 | 0.12 | 0.15 | 0.12 | 0.17 | 0.961 | 0.639 |
| Birmingham IBS symptom questionnaire | | | | | | | |
| Constipation | 6.06 | 5.63 | 6.21 | 4.10 | 6.19 | 0.189 | 0.251 |
| Diarrhoea | 1.58 | 1.95 | 2.20 | 2.10 | 2.01 | 0.873 | 0.761 |
| Pain | 3.08 | 1.97 | 2.17 | 1.42 | 2.86 | 0.022 | 0.571 |
| IBS - Quality of life questionnaire | | | | | | | |
| Dysphoria | 12.30 | 11.94 | 11.12 | 11.39 | 11.98 | 0.363 | 0.705 |
| Interference with activity | 11.53 | 11.29 | 10.68 | 10.51 | 11.03 | 0.924 | 0.981 |
| Body Image | 8.37 | 8.51 | 8.23 | 7.69 | 8.81 | 0.012 | 0.887 |
| Health worry | 5.74 | 6.45 | 6.24 | 6.24 | 6.61 | 0.039 | 0.325 |
| Food avoidance | 6.01 | 6.81 | 5.87 | 6.05 | 5.99 | 0.536 | 0.881 |
| Social Reaction | 6.80 | 7.03 | 6.72 | 6.91 | 6.78 | 0.583 | 0.352 |
| Sexual | 2.94 | 3.00 | 2.63 | 2.93 | 2.60 | 0.015 | 0.230 |
| Relationships | 4.68 | 4.97 | 4.25 | 4.59 | 4.76 | 0.449 | 0.930 |

| | LSD | | | | | |
|---|---|---|---|---|---|---|
| | Washout vs. intervention | Intervention vs. intervention | Difference from washout vs. interventions p-values | | | |
| | | | Placebo | ACTAZIN-L | ACTAZIN-H | GOLD |
| Daily diaries questionnaire | | | | | | |
| Number of daily bowel movements | 120% | 127% | 0.813 | 0.894 | 0.479 | 0.546 |
| Bristol stool scale | 0.36 | 0.46 | 0.223 | 0.396 | 0.799 | 0.437 |
| Strain | 0.15 | 0.20 | 0.433 | 0.462 | 0.147 | 0.305 |
| Incomplete evacuation | 0.14 | 0.18 | 0.155 | 0.852 | 0.957 | 0.749 |
| Bloating | 0.05 | 0.06 | 0.199 | 0.313 | 0.958 | 0.461 |
| Wind | 0.16 | 0.20 | 0.667 | 0.158 | 0.474 | 0.015 |

TABLE 8-continued

Analysis of variance results for daily diaries, Birmingham IBS symptoms, and IBS-quality of life questionnaires in the FC cohort

| | | | | | | |
|---|---|---|---|---|---|---|
| Manual manoeuvres | 0.08 | 0.10 | 0.132 | 0.072 | 0.140 | 0.535 |
| Laxatives | 0.01 | 0.02 | 0.795 | 0.354 | 0.673 | 0.706 |
| Abdominal pain | 0.09 | 0.12 | 0.023 | 0.316 | 0.813 | 0.323 |
| Birmingham IBS symptom questionnaire | | | | | | |
| Constipation | 1.72 | 2.22 | 0.872 | 0.510 | 0.982 | 0.018 |
| Diarrhoea | 1.15 | 1.48 | 0.441 | 0.908 | 0.738 | 0.872 |
| Pain | 0.96 | 1.24 | 0.642 | 0.070 | 0.156 | 0.004 |
| IBS - Quality of life questionnaire | | | | | | |
| Dysphoria | 1.05 | 1.36 | 0.533 | 0.931 | 0.106 | 0.262 |
| Interference with activity | 0.96 | 1.24 | 0.296 | 0.582 | 0.459 | 0.276 |
| Body Image | 0.77 | 0.99 | 0.250 | 0.431 | 0.132 | 0.005 |
| Health worry | 0.69 | 0.89 | 0.014 | 0.636 | 0.277 | 0.281 |
| Food avoidance | 1.03 | 1.33 | 0.975 | 0.116 | 0.817 | 0.905 |
| Social Reaction | 0.50 | 0.64 | 0.929 | 0.326 | 0.808 | 0.610 |
| Sexual | 0.36 | 0.46 | 0.060 | 0.028 | 0.830 | 0.070 |
| Relationships | 0.60 | 0.78 | 0.775 | 0.475 | 0.090 | 0.571 |

LSD—Least significant difference between two means at the 5% level.

Example 7

Clinical Trial to Assess Effects of Gold3 Gold Kiwifruit Powder on Colonic Microbial Populations Overview The human intervention study described in Example 5 was used to ascertain the effect of kiwifruit-derived supplements on colonic microbial composition and metabolism. As described, two kiwifruit-derived supplements, ACTAZIN™ green-fleshed (*Actinidia deliciosa* 'Hayward') and GOLD gold-fleshed (*Actinidia chinensis* 'Zesy002' Gold3) (Anagenix Ltd, Wellington, New Zealand), were used as dietary interventions in the trial. These capsules were cold-processed dietary supplements formulated to maintain the integrity of innate kiwifruit compounds. Preparation was carried out in accordance with Example 1, above.

Results for ACTAZIN™ (2400 mg and 600 mg) and GOLD (2400 mg) kiwifruit supplements were evaluated. The trialists were recruited into a healthy group of 19 participants and a functionally constipated group of 9 participants, each of whom consumed all the treatments and a placebo for 4 weeks in a random crossover manner interspersed with 2 week washout periods. Modification of colonic microbiota composition was determined by 16S rRNA gene sequencing and metabolic end products were measured using gas chromatography.

In the functionally constipated group, it was observed that *Faecalibacterium prausnitzii* relative abundance significantly increased (P=0.024) from 3.4% to 7.0% following GOLD supplementation. Lower proportions of *F. prausnitzii* are often associated with gastrointestinal disorders; especially those with an inflammatory pathology. The discovery that GOLD supplementation increased *F. prausnitzii* abundance offers a strategy for correcting colonic microbiota dysbiosis, as *F. prausnitzii* is a key butyrate producer and has also been shown to exert anti-inflammatory effects.

DNA Extraction, PCR and 16S rRNA Gene Sequencing

All faecal samples were sent on dry ice to Plant & Food Research, Palmerston North where they were received and stored at −20° C. Two hundred and fifty milligrams of each sample was weighed into a sterile microtube and DNA was extracted from each sample using the MO-BIO PowerSoil® DNA Isolation Kit (MO-BIO Laboratories, Carlsbad, Calif., US #12888).

PCR was run to amplify variable regions V3-V4 of the 16S rRNA gene (position 341-805 in the *Escherichia coli* rRNA gene) using forward primer Bakt_341F TCGTCG-GCAGCGTCAGATGTGTATAAGAGACAGC-CTACGGGNGGCWGCAG (SEQ ID NO: 1) and reverse primer Bakt_805R GTCTCGTGGGCTCGGAGATGTG-TATAAGAGACAGGACTACHVGGGTATCTAA TCC (SEQ ID NO: 2) Herlemann et al. 2000; W=A/T, H=A/C/T, V=G/C/A, N=G/A/T/C). The primer sequence shown in bold was used to bind to the amplicon region of interest and the remainder of the primer was used to bind the Illumina® index adaptors.

Each PCR was performed in a 50 µL total volume consisting of 25 µL of HotStarTaq® master mix (QIAGEN, Melbourne, Australia), 1 µL template DNA or negative control (sterile H$_2$O) and 12 µL of each of the forward and reverse primers at a final concentration of 0.1 µM. PCR conditions included an initial denaturation of 95° C. for 15 min, followed by thirty cycles of 30 s denaturation at 95° C., 30 s annealing at 55° C., 30 s extension at 72° C., and finishing with a 5 min extension step at 72° C.

The PCR products were column purified using the QIAquick PCR purification kit, (QIAGEN, Melbourne, Australia), quantified using the Qubit® 2.0 fluorometer (Life Technologies™), and sent to New Zealand Genomics Ltd (NZGL), Massey Genome Service (MGS), New Zealand (NZ). At NZGL, the second PCR step was performed, the amplicons were library QC checked, diluted and pooled. The libraries were then loaded onto the Illumina® MiSeq instrument over three 2×250 bp paired end (PE) runs.

Bioinformatics

The Illumina® MiSeq sequencing data was analysed by software (Quantitative Insights into Microbial Ecology (QIIME) software version 1.8.0; Caporaso et al. 2010). To assemble the paired-end reads into a single continuous sequence, PANDASeq was used with parameters of at least 40 bp overlap, a minimum of 350 bp length and maximum of 500 bp length (Masella et al. 2012). Putative chimeras were filtered from the sequences and the reads were clustered into operational taxonomic units (OTUs) based on a 97% identity threshold value using USEARCH and UCLUST (Edgar 2010). A subsample of the total reads was taken to allow faster processing of the samples and to normalise at approximately 15,000 reads per sample, which is sufficient for phylogenetic and taxonomic assignment (Caporaso et al. 2011; Schloss et al. 2012).

Alignment of the sequences was carried out using PyNAST (Caporaso et al. 2010) with reference to the Greengenes core reference database (version 13_8) (DeSantis et al. 2006). Taxonomic assignment was made using the RDP Naive Bayesian classifier (Wang et al. 2007). The healthy and FC groups were analysed separately and the effect of each of the four treatments on microbial community composition was determined by comparing the average abundance of each bacterial genus after each treatment (greater than 1% abundance in at least one of the eight samples) with the average value before treatment.

Organic Acid Quantification by GC

A 500-1000 mg portion of each faecal sample was weighed into a clean tube and diluted 1:10 in phosphate-buffered saline (PBS). The internal standard (ethyl butyrate) was included to give a final concentration of 5 mM. The organic acids were quantified by GC using a modified method as previously described (Richardson et al. 1989).

Analysis was performed on a Shimadzu gas chromatograph system (GC-17A, Kyoto, Japan) equipped with a flame ionisation detector and fitted with a HP-1 column (Agilent Technologies, Santa Clara, Calif., USA). The instrument was controlled and chromatograms acquired using GC Solution Chromatography Data System software (Shimadzu, Version 2.3). The standard curves were prepared following the analysis of standard solutions of formic, acetic, propionic, isobutyric, butyric, lactic, succinic, isovaleric, valeric, heptanoic, and hexanoic acids. Organic acid concentrations were expressed as µmol/g of faeces.

Statistical Analysis

Statistical calculations were conducted in R Studio using the stats package (R Studio 2012). The Wilcoxon Signed Rank test was performed to assess significant differences between taxonomy at the genus level and significant differences between organic acid concentrations before and after each treatment. A P value of less than 0.05 was deemed significant after correcting for multiple comparisons using the False Discovery Rate (FDR) method in the p.adjust function in R Studio (Benjamini and Hochberg 1995).

Example 8

Results of Treatment on Microbial Colonic Populations 16S rRNA Gene Sequencing

High throughput sequencing was carried out for variable regions of the 16S rRNA gene, amplified from faecal sample-derived bacterial DNA. This resulted in 26.3 million reads. After quality filtering, chimera removal and subsampling, a total of 3.72 million reads were obtained at an average of 14879 (14139 minimum-14999 maximum) sequences per sample.

Over all samples, 218 species-level phylotypes were observed at a 97% sequence identity threshold. In the healthy group, Clostridiales increased significantly after the GOLD supplementation from 5.0% to 7.6% (P=0.042) (Table 9). In the FC group, *Faecalibacterium prausnitzii* significantly increased after GOLD treatment from 3.4% to 7.0% (P=0.024), a two-fold increase, while *Dorea* spp. increased from 0.9% to 1.4% (P=0.008) after the ACTAZIN™ H treatment (Table 10). For the FC group, *Ruminococcus* spp. decreased from 9.9% to 5.6% (P=0.024) after the placebo treatment period (Table 10).

Figure 5B:
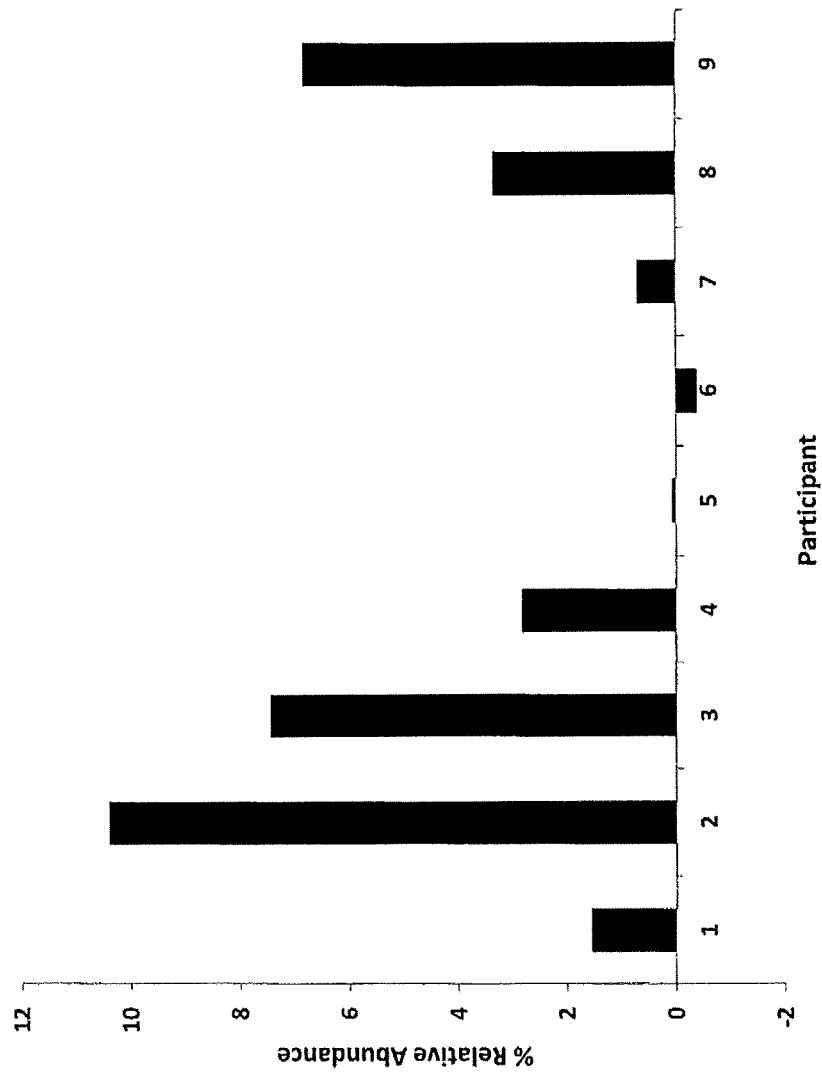
FIG. 5B: Net difference in abundance of *Faecalibacterium prausnitzii* in functionally constipated participants after GOLD (Gold3) treatment

Of the nine participants that consumed GOLD in the FC group, eight registered a net *F. prausnitzii* increase, with only one slightly minor reduction being observed (FIG. 5B). When comparing the healthy and FC groups, many of the observed genera were significantly different between groups, most notable being *Bacteroides* spp. and Ruminococcaceae which were significantly higher in the healthy group and *Akkermansia* spp. which was significantly elevated in the FC group.

Organic Acid Production

Lactate, formate, and isovalerate were not detected in faecal samples in this study. Hexanoate significantly decreased in concentration from 0.6 mol/g to 0.2 mol/g (P=0.030) after the GOLD treatment in the healthy group (Table 11). Succinate significantly decreased in concentration from 2.3 µmol/g to 1.7 µmol/g (P=0.040) after the placebo treatment in the FC group (Table 12). There were no other significant alterations to organic acid concentrations in any of the treatments. Quantitative differences between before and after each treatment were generally modest, except for acetate which increased or decreased by up to 13 µmol/g after some treatments.

TABLE 9

Relative abundance of prevalent bacterial groups in response to treatments in the healthy group

|  | Placebo | | GOLD | | ACTAZIN ™ L | | ACTAZIN ™ H | |
| --- | --- | --- | --- | --- | --- | --- | --- | --- |
|  | Pre | Post | Pre | Post | Pre | Post | Pre | Post |
| *Bacteroides* | 18.8 ± 4.0 | 18.0 ± 3.2 | 23.1 ± 4.6 | 22.0 ± 4.2 | 16.7 ± 3.1 | 18.4 ± 3.9 | 19.4 ± 3.2 | 18.1 ± 3.8 |
| Ruminococcaceae [1] | 16.3 ± 2.4 | 19.6 ± 3.0 | 17.4 ± 2.3 | 17.8 ± 2.5 | 19.9 ± 2.5 | 22.2 ± 3.8 | 18.4 ± 2.6 | 19.9 ± 3.3 |
| Lachnospiraceae [1] | 10.8 ± 1.3 | 11.0 ± 1.5 | 11.9 ± 1.9 | 9.5 ± 1.3 | 11.6 ± 1.6 | 9.3 ± 1.7 | 11.6 ± 1.6 | 11.0 ± 1.4 |
| *Faecalibacterium* | 7.0 ± 1.5 | 5.7 ± 1.0 | 7.2 ± 1.6 | 5.3 ± 0.9 | 6.3 ± 1.6 | 4.6 ± 0.8 | 6.7 ± 1.1 | 6.5 ± 1.6 |
| Clostridiales [1] | 5.9 ± 0.9 | 5.7 ± 1.0 | 5.0 ± 0.9 | 7.6 ± 1.1* | 5.9 ± 0.7 | 5.0 ± 1.1 | 6.6 ± 1.2 | 5.6 ± 0.9 |
| *Coprococcus* | 6.6 ± 1.0 | 5.5 ± 0.8 | 5.9 ± 1.1 | 5.1 ± 0.7 | 5.4 ± 0.8 | 5.2 ± 0.8 | 5.1 ± 0.8 | 4.9 ± 0.8 |
| *Blautia* | 5.8 ± 0.9 | 4.7 ± 1.0 | 4.3 ± 0.6 | 4.8 ± 1.0 | 4.7 ± 0.7 | 6.3 ± 1.7 | 4.8 ± 1.1 | 6.1 ± 1.8 |
| *Ruminococcus* | 4.9 ± 1.0 | 6.6 ± 1.6 | 4.2 ± 0.6 | 4.4 ± 1.0 | 6.4 ± 1.0 | 7.2 ± 1.3 | 4.1 ± 0.8 | 5.6 ± 1.2 |
| Rikenellaceae [1] | 2.8 ± 0.9 | 2.7 ± 0.7 | 2.7 ± 0.7 | 2.9 ± 1.0 | 2.8 ± 1.0 | 2.5 ± 0.9 | 3.0 ± 0.6 | 3.5 ± 0.8 |
| *Bifidobacterium* | 3.0 ± 1.0 | 2.3 ± 0.6 | 2.5 ± 1.2 | 2.1 ± 0.6 | 2.0 ± 0.4 | 3.5 ± 1.1 | 2.7 ± 0.9 | 2.6 ± 0.8 |
| Bacteroidales [1] | 2.2 ± 1.0 | 2.2 ± 0.8 | 2.0 ± 0.9 | 1.9 ± 0.8 | 1.3 ± 0.4 | 1.2 ± 0.3 | 2.6 ± 1.1 | 1.7 ± 0.6 |
| *Lachnospira* | 1.6 ± 0.5 | 1.1 ± 0.2 | 1.3 ± 0.3 | 1.5 ± 0.5 | 1.0 ± 0.2 | 1.1 ± 0.3 | 1.8 ± 0.5 | 1.3 ± 0.4 |
| *Parabacteroides* | 1.2 ± 0.3 | 1.6 ± 0.5 | 1.8 ± 0.6 | 1.1 ± 0.2 | 1.3 ± 0.3 | 1.0 ± 0.2 | 1.7 ± 0.3 | 1.5 ± 0.3 |

TABLE 9-continued

Relative abundance of prevalent bacterial groups in response to treatments in the healthy group

|  | Placebo | | GOLD | | ACTAZIN™ L | | ACTAZIN™ H | |
| --- | --- | --- | --- | --- | --- | --- | --- | --- |
|  | Pre | Post | Pre | Post | Pre | Post | Pre | Post |
| Collinsella | 1.8 ± 0.7 | 1.2 ± 0.4 | 0.9 ± 0.4 | 1.3 ± 0.4 | 1.6 ± 0.6 | 1.2 ± 0.3 | 1.5 ± 0.6 | 1.1 ± 0.3 |
| Akkermansia | 1.3 ± 0.5 | 1.4 ± 0.6 | 1.8 ± 0.7 | 1.6 ± 0.7 | 1.6 ± 0.6 | 1.8 ± 0.5 | 1.4 ± 0.4 | 1.0 ± 0.3 |
| Oscillospira | 1.1 ± 0.2 | 1.1 ± 0.2 | 1.1 ± 0.2 | 1.6 ± 0.3 | 1.4 ± 0.2 | 1.5 ± 0.5 | 1.2 ± 0.1 | 1.5 ± 0.2 |
| Prevotella | 1.5 ± 0.7 | 2.6 ± 1.8 | 0.8 ± 0.4 | 2.1 ± 1.5 | 2.5 ± 1.33 | 0.7 ± 0.3 | 0.9 ± 0.5 | 1.6 ± 0.9 |
| Dorea | 1.2 ± 0.4 | 1.2 ± 0.3 | 0.9 ± 0.2 | 1.4 ± 0.4 | 1.1 ± 0.2 | 0.9 ± 0.2 | 0.8 ± 0.2 | 1.0 ± 0.2 |
| Clostridiaceae [1] | 1.2 ± 0.4 | 0.9 ± 0.3 | 0.9 ± 0.2 | 0.9 ± 0.2 | 0.8 ± 0.2 | 1.2 ± 0.4 | 0.8 ± 0.2 | 0.9 ± 0.3 |
| Unassigned | 0.8 ± 0.1 | 1.0 ± 0.2 | 0.8 ± 0.1 | 1.0 ± 0.2 | 0.9 ± 0.1 | 0.9 ± 0.1 | 0.8 ± 0.1 | 0.8 ± 0.1 |

Illumina ® MiSeq sequencing data displaying genera that are present at greater than one percent abundance in at least one sample. Data are the calculated average values for all participants ± standard error of the mean (SEM) before and after each treatment period.
*$P \leq 0.05$ - Significantly different compared with pre-treatment based on the Wilcoxon Signed Rank test after false discovery rate correction for multiple comparisons.
[1] Some bacteria could only be classified as far as the order or family level.

TABLE 10

Relative abundance of prevalent bacterial groups in response to treatments in the functionally constipated group

|  | Placebo | | GOLD | | ACTAZIN™ L | | ACTAZIN™ H | |
| --- | --- | --- | --- | --- | --- | --- | --- | --- |
|  | Pre | Post | Pre | Post | Pre | Post | Pre | Post |
| Ruminococcaceae [1] | 17.2 ± 2.3 | 19.9 ± 2.9 | 17.1 ± 3.8 | 16.3 ± 2.1 | 17.9 ± 2.6 | 15.0 ± 2.3 | 16.5 ± 3.1 | 18.8 ± 2.1 |
| Bacteroides | 12.6 ± 3.1 | 14.4 ± 2.2 | 14.2 ± 2.6 | 15.5 ± 2.6 | 13.9 ± 2.2 | 12.2 ± 2.5 | 14.0 ± 2.9 | 16.3 ± 3.1 |
| Lachnospiraceae [1] | 11.4 ± 1.6 | 8.0 ± 2.3 | 10.0 ± 2.5 | 13.9 ± 3.3 | 10.8 ± 3.1 | 11.0 ± 2.3 | 11.7 ± 2.5 | 8.7 ± 2.2 |
| Faecalibacterium | 7.9 ± 2.8 | 5.8 ± 2.1 | 3.4 ± 1.0 | 7.0 ± 1.1* | 4.9 ± 1.7 | 5.0 ± 1.4 | 7.7 ± 2.1 | 3.1 ± 1.0 |
| Clostridiales [1] | 4.8 ± 0.6 | 6.8 ± 1.7 | 6.4 ± 1.3 | 5.5 ± 1.1 | 6.4 ± 1.2 | 6.7 ± 1.7 | 6.0 ± 1.4 | 7.5 ± 1.8 |
| Coprococcus | 6.5 ± 1.4 | 6.1 ± 1.1 | 6.7 ± 1.7 | 6.6 ± 1.4 | 6.9 ± 1.4 | 8.6 ± 1.2 | 6.0 ± 1.2 | 7.1 ± 1.9 |
| Blautia | 6.6 ± 1.8 | 3.5 ± 0.9 | 7.1 ± 2.0 | 6.0 ± 1.5 | 6.9 ± 1.5 | 7.5 ± 1.8 | 5.9 ± 2.1 | 5.4 ± 1.3 |
| Ruminococcus | 9.9 ± 2.6 | 5.6 ± 1.0* | 6.4 ± 1.4 | 5.5 ± 0.7 | 6.2 ± 2.0 | 7.4 ± 1.5 | 5.5 ± 1.1 | 7.2 ± 1.3 |
| Bifidobacterium | 2.6 ± 1.3 | 2.6 ± 1.0 | 3.5 ± 1.5 | 2.6 ± 1.0 | 2.7 ± 1.5 | 2.7 ± 0.9 | 4.0 ± 1.6 | 1.8 ± 0.8 |
| Akkermansia | 2.7 ± 1.7 | 4.8 ± 2.0 | 5.0 ± 1.8 | 2.6 ± 1.0 | 3.3 ± 1.1 | 3.3 ± 1.5 | 3.6 ± 1.0 | 5.6 ± 2.3 |
| Rikenellaceae [1] | 2.3 ± 0.6 | 3.1 ± 0.6 | 3.9 ± 1.2 | 2.4 ± 0.5 | 4.0 ± 1.1 | 3.9 ± 1.3 | 2.6 ± 0.7 | 3.2 ± 0.9 |
| Christensenellaceae [1] | 1.0 ± 0.6 | 1.5 ± 0.6 | 2.2 ± 1.4 | 1.1 ± 0.6 | 1.8 ± 0.8 | 1.4 ± 0.6 | 2.3 ± 1.6 | 2.2 ± 1.3 |
| Prevotella | 1.8 ± 1.1 | 0.6 ± 0.3 | 0.2 ± 0.1 | 0.5 ± 0.3 | 0.5 ± 0.3 | 0.9 ± 0.5 | 2.0 ± 1.1 | 0.2 ± 0.1 |
| Collinsella | 1.6 ± 0.6 | 1.2 ± 0.3 | 1.6 ± 0.4 | 1.3 ± 0.3 | 1.2 ± 0.4 | 1.8 ± 0.7 | 1.6 ± 0.6 | 1.4 ± 0.3 |
| Unassigned | 1.0 ± 0.1 | 1.1 ± 0.1 | 1.1 ± 0.2 | 1.0 ± 0.1 | 1.0 ± 0.1 | 1.0 ± 0.1 | 1.3 ± 0.4 | 1.0 ± 0.1 |
| Parabacteroides | 1.3 ± 0.4 | 1.3 ± 0.4 | 1.2 ± 0.3 | 1.3 ± 0.4 | 1.7 ± 0.4 | 1.2 ± 0.4 | 1.3 ± 0.4 | 1.5 ± 0.3 |
| Oscillospira | 1.3 ± 0.1 | 1.5 ± 0.3 | 1.6 ± 0.2 | 1.8 ± 0.3 | 1.6 ± 0.2 | 1.5 ± 0.3 | 1.3 ± 0.2 | 1.8 ± 0.3 |
| Lachnospira | 1.0 ± 0.5 | 1.0 ± 0.4 | 0.6 ± 0.2 | 1.6 ± 0.9 | 1.3 ± 0.5 | 1.2 ± 0.5 | 1.3 ± 0.6 | 0.5 ± 0.1 |
| Dorea | 1.5 ± 0.4 | 1.4 ± 0.3 | 1.3 ± 0.3 | 1.2 ± 0.3 | 1.2 ± 0.3 | 1.2 ± 0.4 | 0.9 ± 0.2 | 1.4 ± 0.3* |
| Coriobacteriaceae [1] | 0.9 ± 0.3 | 1.2 ± 0.5 | 1.5 ± 0.4 | 1.2 ± 0.5 | 1.1 ± 0.3 | 1.1 ± 0.3 | 0.8 ± 0.2 | 1.2 ± 0.4 |
| Barnesiellaceae [1] | 0.9 ± 0.3 | 4.0 ± 2.4 | 1.0 ± 0.4 | 1.0 ± 0.3 | 1.1 ± 0.3 | 1.4 ± 0.5 | 0.8 ± 0.3 | 0.8 ± 0.3 |
| Clostridiaceae [1] | 0.4 ± 0.1 | 1.1 ± 0.7 | 0.9 ± 0.5 | 1.0 ± 0.7 | 0.3 ± 0.1 | 0.4 ± 0.1 | 0.4 ± 0.1 | 0.3 ± 0.1 |

Illumina MiSeq sequencing data displaying genera that are present at greater than one percent abundance in at least one sample. Data are the calculated average values for all participants ± standard error of the mean (SEM) before and after each treatment period.
*$P \leq 0.05$ - Significantly different compared to pre-treatment based on the Wilcoxon Signed Rank test after false discovery rate correction for multiple comparisons.
[1] Some bacteria could only be classified as far as the order or family level.

TABLE 11

Organic acid concentrations in faecal samples in response to the four treatments in the healthy group

|  | Mean Pre | SEM Pre | Mean Post | SEM Post | P value | Difference |
| --- | --- | --- | --- | --- | --- | --- |
| Placebo | | | | | | |
| Acetate | 36.7 | 5.8 | 43.2 | 5.2 | 1.00 | 6.5 |
| Butyrate | 10.5 | 2.4 | 13.9 | 2.6 | 0.28 | 3.4 |
| Heptanoate | 0.0 | 0.0 | 0.0 | 0.0 | 0.84 | 0.0 |
| Hexanoate | 0.4 | 0.2 | 0.6 | 0.2 | 0.58 | 0.2 |
| Isobutyrate | 0.6 | 0.2 | 0.8 | 0.2 | 0.82 | 0.2 |
| Propionate | 7.8 | 1.7 | 10.6 | 2.3 | 0.74 | 2.8 |
| Succinate | 1.6 | 0.6 | 1.0 | 0.1 | 0.48 | −0.6 |
| Valerate | 1.5 | 0.2 | 2.0 | 0.3 | 0.34 | 0.5 |
| GOLD | | | | | | |
| Acetate | 43.7 | 5.5 | 31.4 | 4.8 | 0.05 | −12.3 |
| Butyrate | 14.2 | 3.0 | 9.5 | 2.7 | 0.18 | −4.7 |
| Heptanoate | 0.1 | 0.1 | 0.0 | 0.0 | 0.20 | −0.1 |
| Hexanoate | 0.6 | 0.2 | 0.2 | 0.1 | 0.03* | −0.4 |
| Isobutyrate | 0.6 | 0.2 | 0.4 | 0.1 | 0.92 | −0.2 |
| Propionate | 7.0 | 1.4 | 6.0 | 1.4 | 0.96 | −1.0 |
| Succinate | 1.5 | 0.6 | 0.9 | 0.1 | 1.00 | −0.6 |
| Valerate | 1.6 | 0.2 | 1.3 | 0.1 | 0.30 | −0.3 |
| ACTAZIN™ L | | | | | | |
| Acetate | 42.8 | 5.9 | 44.0 | 6.1 | 1.00 | 1.2 |
| Butyrate | 15.3 | 2.2 | 13.5 | 2.2 | 1.00 | −1.8 |
| Heptanoate | 0.1 | 0.1 | 0.0 | 0.0 | 1.00 | −0.1 |
| Hexanoate | 0.7 | 0.3 | 0.8 | 0.3 | 1.00 | 0.1 |
| Isobutyrate | 0.8 | 0.3 | 0.7 | 0.2 | 1.00 | −0.1 |
| Propionate | 8.9 | 1.3 | 9.9 | 1.5 | 1.00 | 1.0 |
| Succinate | 2.2 | 0.8 | 1.1 | 0.2 | 0.52 | −1.1 |
| Valerate | 1.7 | 0.3 | 1.8 | 0.2 | 1.00 | 0.1 |

TABLE 11-continued

Organic acid concentrations in faecal samples in response to the four treatments in the healthy group

|  | Mean Pre | SEM Pre | Mean Post | SEM Post | P value | Difference |
|---|---|---|---|---|---|---|
| ACTAZIN ™ H | | | | | | |
| Acetate | 45.2 | 6.7 | 32.8 | 5.0 | 0.32 | −12.4 |
| Butyrate | 11.9 | 2.5 | 10.0 | 2.4 | 0.70 | −1.9 |
| Heptanoate | 0.0 | 0.0 | 0.0 | 0.0 | 1.00 | 0.0 |
| Hexanoate | 0.3 | 0.1 | 0.4 | 0.2 | 1.00 | 0.1 |
| Isobutyrate | 0.7 | 0.2 | 0.5 | 0.1 | 0.76 | −0.2 |
| Propionate | 8.5 | 1.1 | 7.7 | 1.7 | 1.00 | −0.8 |
| Succinate | 2.7 | 1.6 | 1.1 | 0.2 | 1.00 | −1.6 |
| Valerate | 1.5 | 0.2 | 1.5 | 0.2 | 1.00 | 0.0 |

Levels measured by gas chromatography (GC), expressed in μmol/g faeces. The difference denotes whether a net increase (positive values) or a net decrease (negative values) was observed after treatments.
*$P \leq 0.05$ - Significantly different compared to pre-treatment based on the Wilcoxon Signed Rank test after false discovery rate correction for multiple comparisons.

TABLE 12

Organic acid concentrations in faecal samples in response to the four treatments in the functionally constipated group

|  | Mean Pre | SEM Pre | Mean Post | SEM Post | P value | Difference |
|---|---|---|---|---|---|---|
| Placebo | | | | | | |
| Acetate | 33.7 | 7.2 | 34.7 | 3.9 | 1.00 | 1.0 |
| Butyrate | 7.0 | 2.5 | 5.9 | 2.1 | 1.00 | −1.1 |
| Heptanoate | 0.0 | 0.0 | 0.2 | 0.2 | 1.00 | 0.2 |
| Hexanoate | 0.2 | 0.1 | 0.2 | 0.1 | 1.00 | 0.0 |
| Isobutyrate | 1.2 | 0.3 | 1.5 | 0.3 | 1.00 | 0.3 |
| Propionate | 8.5 | 1.5 | 9.0 | 1.4 | 1.00 | 0.5 |
| Succinate | 2.3 | 0.3 | 1.7 | 0.2 | 0.04* | −0.6 |
| Valerate | 1.4 | 0.3 | 1.5 | 0.3 | 1.00 | 0.1 |
| GOLD | | | | | | |
| Acetate | 40.5 | 8.7 | 39.1 | 7.4 | 1.00 | −1.4 |
| Butyrate | 8.3 | 3.8 | 8.5 | 2.3 | 1.00 | 0.2 |
| Heptanoate | 0.0 | 0.0 | 0.0 | 0.0 | 0.22 | 0.0 |
| Hexanoate | 0.1 | 0.1 | 0.4 | 0.2 | 0.56 | 0.3 |
| Isobutyrate | 1.0 | 0.3 | 1.5 | 0.2 | 0.72 | 0.5 |
| Propionate | 9.2 | 2.1 | 10.4 | 2.2 | 1.00 | 1.2 |
| Succinate | 1.7 | 0.2 | 1.8 | 0.2 | 1.00 | 0.1 |
| Valerate | 1.4 | 0.3 | 1.8 | 0.3 | 1.00 | 0.4 |
| ACTAZIN ™ L | | | | | | |
| Acetate | 35.2 | 5.4 | 44.7 | 10.2 | 1.00 | 9.5 |
| Butyrate | 9.4 | 2.4 | 10.3 | 3.1 | 1.00 | 0.9 |
| Heptanoate | 0.1 | 0.0 | 0.1 | 0.1 | 1.00 | 0.0 |
| Hexanoate | 0.3 | 0.2 | 0.7 | 0.5 | 1.00 | 0.4 |
| Isobutyrate | 1.6 | 0.3 | 1.6 | 0.3 | 1.00 | 0.0 |
| Propionate | 9.2 | 1.7 | 10.5 | 2.1 | 1.00 | 1.3 |
| Succinate | 1.8 | 0.1 | 1.7 | 0.1 | 0.60 | −0.1 |
| Valerate | 1.9 | 0.3 | 2.0 | 0.3 | 1.00 | 0.1 |
| ACTAZIN ™ H | | | | | | |
| Acetate | 46.0 | 10.0 | 32.3 | 4.2 | 0.72 | −13.7 |
| Butyrate | 9.5 | 3.7 | 4.0 | 1.2 | 1.00 | −5.5 |
| Heptanoate | 0.2 | 0.2 | 0.0 | 0.0 | 0.28 | −0.2 |
| Hexanoate | 0.3 | 0.2 | 0.1 | 0.0 | 0.40 | −0.2 |
| Isobutyrate | 1.2 | 0.4 | 1.4 | 0.3 | 0.72 | 0.2 |
| Propionate | 10.8 | 3.2 | 7.5 | 1.0 | 1.00 | −3.3 |
| Succinate | 2.0 | 0.2 | 1.9 | 0.2 | 1.00 | −0.1 |
| Valerate | 1.4 | 0.4 | 1.3 | 0.2 | 1.00 | −0.1 |

Levels measured by gas chromatography (GC), expressed in μmol/g faeces. The difference denotes whether a net increase (positive values) or a net decrease (negative values) was observed after treatments.
*$P \leq 0.05$ - Significantly different compared with pre-treatment based on the Wilcoxon Signed Rank test after false discovery rate correction for multiple comparisons.

Discussion

It was determined that several bacterial groups were significantly altered in abundance after consumption of kiwifruit-derived supplements. *Clostridiales* increased by 2.6% after GOLD (Gold3) supplementation in the healthy group, although the implications of this increase are still under investigation. *F. prausnitzii* relative abundance was significantly elevated (3.6%) in the FC group after a 4 week period of supplementation with the gold kiwifruit based GOLD.

Notably, *F. prausnitzii* is a known butyrate producer. Butyrate is the preferred energy source for colonic epithelial cells and plays a role in alleviating inflammation as well as mitigating carcinogenesis, pathogenic colonisation, and oxidative stress (Hamer et al. 2008; Macfarlane and Macfarlane 2011). In a recent study, it was demonstrated that administration of a butyrate producing bacterium, *Clostridium tyrobutyricum*, protected mice from dextran sodium sulphate-induced colitis (Hudcovic et al. 2012). Therefore, increasing the amount of *F. prausnitzii* in the colon may help mitigate the symptoms of gastrointestinal disorders, through elevated butyrate production.

As the human gastrointestinal tract consists of approximately $10^{14}$ microbial cells (Egert et al. 2006) and abundance of *F. prausnitzii* is about 5% (Miquel et al. 2013), this equates to a concentration of approximately five trillion *F. prausnitzii* cells, which may exert an appreciable effect on microbial activities and metabolism. The present study showed a total proportion of 5.6% abundance of *F. prausnitzii* from all samples in the FC group (the average taken across all samples in the FC group, including all treatments and washouts), while 6.1% was observed in the healthy group. The samples from participants in the FC group prior to administration of GOLD supplementation had a relatively low abundance of *F. prausnitzii* of 3.4% which increased two-fold to 7.0% after GOLD treatment. A decrease from 7.2% to 5.3% was observed in the healthy group which could be due to the already high levels at baseline. This has been observed in other studies, where the baseline concentration of a bacterial group has a substantial bearing on the magnitude of effect observed in response to a dietary intervention (Kolida et al. 2007; Tuohy et al. 2001).

There were minor differences between organic acids after treatments which could be attributed to using faecal samples as a proxy for in situ determination of organic acid composition and concentration. Organic acid concentrations decrease distally in the large bowel which is due to secondary fermentation, absorption into the bloodstream and/or utilisation of organic acids (particularly butyrate) by colonocytes (Bach et al. 2000). Therefore, measurement of organic acids in faecal samples may greatly underestimate the concentration of in situ organic acids (Millet et al. 2010).

Butyrate was slightly higher in faecal samples from participants in the FC group, which aligns with the increased *F. prausnitzii* abundance. Lactate, formate, and isovalerate were not detected in the faecal samples from either group in the study. Lactate is not normally detected in high concentrations in faecal samples from healthy individuals as it is an intermediate in many metabolic networks and is consumed by members of the microbiota as part of normal metabolism (Duncan et al. 2004; Belenguer et al. 2011). Formate also acts as an intermediate and can be converted to methane, carbon dioxide and water as well as only being produced in the initial phase of fermentation, normally in the proximal colon (Pryde et al. 2002; Huda-Faujan et al. 2010).

*F. prausnitzii* is well characterised in terms of its metabolic capabilities and fermentation profile, despite being an oxygen sensitive bacterium that is difficult to culture in the laboratory (Duncan et al. 2002). In spite of its numerical dominance in the gut and butyrate-producing nature, *F. prausnitzii* has yet to be utilised to improve digestive health.

Given that a depleted abundance of *F. prausnitzii* is observed in many gastrointestinal disorders, it has been proposed that *F. prausnitzii* could be formulated as a probiotic and administered to IBS or IBD sufferers (Sokol et al. 2008; Sartor 2011). However, this work is still ongoing. The oxygen sensitivity of *F. prausnitzii* makes it challenging to formulate as a component for probiotic compositions.

The gold kiwifruit derived supplement, GOLD, provides a means for selectively stimulating the proliferation of the commensal *F. prausnitzii*, and is therefore considered particularly useful for inflammation-related gastrointestinal disorders. In conclusion, GOLD, has ameliorated *F. prausnitzii* depleted dysbiosis in functionally constipated participants. As such, the Gold3 gold kiwifruit powder finds use for restoring the microbiota to a healthy state with anti-inflammatory benefits and higher in situ butyrate concentrations.

Example 9 qPCR Analysis of Microbiome for the Human Clinical Trial

Summary

This study investigated the impact of ACTAZIN™ (2400 mg) and GOLD (2400 mg) kiwifruit supplements on faecal microbial concentrations in a human intervention study as well as in vitro fermentation experiments. The objective was to determine the effect of kiwifruit-based interventions on the microbial composition of the samples. The modification of colonic microbiota composition was determined by real-time quantitative polymerase chain reaction (qPCR) which supplements existing 16S rRNA gene sequencing data obtained previously. See Examples 7 and 8, above.

Real-time qPCR is a common method used to investigate the microbial ecology of the gastrointestinal tract. It has been used in numerous studies and can give a quantitative indication of microbial numbers. Quantification was carried out on the Roche LightCycler® 480 instrument. In addition to total bacteria, individual bacterial groups quantified were *Clostridium coccoides* group, *Lachnospiraceae*, *Bacteroides-Prevotella-Porphyromonas* group, *Bifidobacteria*, *Lactobacilli* and *Faecalibacterium prausnitzii*. The above bacterial groups were also quantified for the in vitro fermentation work with the exception of *Lactobacilli* which was previously tested.

In the functionally constipated group, the concentration of *F. prausnitzii* increased following GOLD supplementation, just falling short of being statistically significant. Lower proportions of *F. prausnitzii* are often associated with gastrointestinal disorders; especially those with an inflammatory pathology. The discovery that GOLD supplementation increased *F. prausnitzii* concentrations concurs with the significant increase in abundance found in the sequencing data and provides support for the prebiotic effects of GOLD consumption.

Background

Green kiwifruit has been shown to improve aspects of gastrointestinal health, including altering the microbial ecology of the colonic environment (Blatchford et al. 2015a; Blatchford et al. 2015b; Parkar et al. 2012). These benefits are thought to derive from the inherent levels of digestion resistant carbohydrates (DRC), polyphenols, and vitamin C (Chan et al. 2007; Ferguson & Ferguson 2003). The benefits of gold kiwifruit have not been clearly established. This study details experiments conducted using samples from the existing human clinical trial (described in Example 5). The randomized, double-blind, placebo-controlled crossover trial, examined the role of two kiwifruit derived ingredients, ACTAZIN™ (green kiwifruit) and GOLD (Gold3 gold kiwifruit), on digestive health.

The primary endpoints measured in the original trial were stool frequency, stool form, and quality of life scores. See Examples 5 and 6. Secondary endpoints included measuring short-chain fatty acids (SCFAs), and also measuring changes in the relative abundances of faecal microbial populations using 16S rRNA gene sequencing. The 16S rRNA gene sequencing analysis gave an overall picture of the microbial ecology of the samples (in the form of relative abundance percentages), but not quantitative results. See Examples 7 and 8, above.

Therefore, the following DNA samples obtained from the original trial were used for the current trial: pre- and post-GOLD 2400 mg intervention samples (n=52), ACTAZIN™ 2400 mg intervention samples (n=52) and placebo samples (n=52). These samples were used to determine the concentration of select bacterial groups using qPCR, which yields a quantitative measure of bacterial concentrations within a sample.

Materials and Methods

As detailed in Example 5, the study design was a randomised double blind placebo controlled cross-over trial with participants consuming four different treatments for four weeks, with a two-week wash out between each treatment. The interventions were delivered in 4×600 mg capsules formulated to appear the same to maintain treatment blinding, as shown in Table 13, below. See also Example 5. As described, the powdered ingredients were prepared from New Zealand green and gold kiwifruit, respectively. See Examples 1 and 5.

TABLE 13

Description of intervention composition

| Intervention | Composition | Dose | Delivery (capsules)/day |
|---|---|---|---|
| ACTAZIN | Green Kiwifruit Powder | 2400 mg | 4 × ACTAZIN ™ |
| GOLD | Gold Kiwifruit Powder | 2400 mg | 4 × GOLD |
| PLACEBO | Isomalt coloured green (E102, E142) | 2400 mg | 4 × Placebo |

Select bacteria were used as representative genera for each of the seven bacterial groups assessed (Table 14). All isolates were grown anaerobically at 37° C. overnight using Hungate tubes sealed with butyl rubber stoppers unless otherwise stated. All media were obtained from Oxoid (Adelaide, Australia), unless otherwise stated.

*Lactobacillus reuteri* (DPC 16) was grown in de Man-Rogosa-Sharpe (MRS) broth; *Bifidobacterium bifidum* (DSM 20082) was grown in MRS broth supplemented with 0.05% (w/v) L-cysteine hydrochloride (Sigma-Aldrich); *Roseburia intestinalis* (DSM 14610) was grown in rumen bacteria media (DSMZ Medium 330); *Lachnospira multipara* (ATCC 19207) was grown in RM02 media supplemented with filtered rumen fluid (Leahy et al. 2010); *Bacteroides fragilis* (ATCC 25285) was grown in Wilkins-Chalgren anaerobe broth supplemented with 0.05% (w/v) L-cysteine hydrochloride (Sigma-Aldrich) for 2 days; *Faecalibacterium prausnitzii* (DSM 17677) was grown in brain heart infusion (BHI) broth supplemented with 0.5% (w/v) yeast extract, 0.0005% (w/v) haemin (Sigma-Aldrich), 0.0005% (w/v) vitamin K (Sigma-Aldrich) and 0.2% L-cysteine hydrochloride (Sigma-Aldrich); *Escherichia coli* (Nissle) was grown in tryptic soy broth (TSB) at 37° C. aerobically.

water to a concentration of 2.5 μM. This was then diluted 1:5 to obtain a 0.5 μM concentrated solution in the PCR reaction.

TABLE 14

Table of primers used - design based on 16S rDNA sequences

| Target bacteria | Bacterial standard | Primer sequence (5' → 3') | Annealing temp (° C.) | Annealing time (s) | Reference |
|---|---|---|---|---|---|
| Total bacteria | *Escherichia coli* Nissle | Fwd: SEQ ID NO: 3 TCCTACGGGAGGCAGCAGT Rev: SEQ ID NO: 4 GGACTACCAGGGTATCTAATCCTGTT | 60 | 60 | (Nadkarni et al. 2002) |
| Bifidobacteria | *Bifidobacteriton bifidum* DSM 20082 | Fwd: SEQ ID NO: 5 GGGTGGTAATGCCGGATG Rev: SEQ ID NO: 6 CCACCGTTACACCGGGAA | 66 | 45 | (Kok et al. 1996) |
| Lactobacilli | *Lactobacillus reuteri* DPC16 | Fwd: SEQ ID NO: 7 CGATGAGTGCTAGGTGTTGGA Rev: SEQ ID NO: 8 CAAGATGTCAAGACCTGGTAAG | 60 | 30 | (Fu et al. 2006) |
| Bacteroides-Prevotella-Porphyromonas | *Bacteroides fragilis* ATCC 25285 | Fwd: SEQ ID NO: 9 GGTGTCGGCTTAAGTGCCAT Rev: SEQ ID NO: 10 CGGATGTAAGGGCCGTGC | 63 | 20 | (Rinttila et al. 2004) |
| *Faecalibacterium prausnitzii* | *Faecalibacterium prausnitzli* DSM 17677 | Fwd: SEQ ID NO: 11 GGAGGAAGAAGGTCTTCGG Rev: SEQ ID NO: 12 AATTCCGCCTACCTCTGCACT | 60 | 20 | (Ramirez-Farias et al. 2009) |
| C coccoides group | *Roseburia intestinalis* DSM 14610 | Fwd: SEQ ID NO: 13 AAATGACGGTACCTGACTAA Rev: SEQ ID NO: 14 CtttGAGTTTCATTCTTGCGAA | 50 | 30 | (Matsuki et al. 2002) |
| Lachnospiraceae | *Lachnospira multipara* ATCC 19207 | Fwd: SEQ ID NO: 15 GACGGTACCTGACTAAGAAGC Rev: SEQ ID NO: 16 AGTTTCATTCTTGCGAACGT | 63 | 30 | (Paturi et al. 2014) |

Specificity of each standard strain to primers was assessed using in silico analysis on SnapGene® software (www.snapgene.com). Cell density was determined using a Neubauer haemocytometer and cultures were diluted or concentrated as required to $1.0 \times 10^8$ or $1.0 \times 10^9$ cells/mL. DNA was then extracted using the MO-BIO PowerSoil® DNA Isolation Kit (MO-BIO Laboratories, Carlsbad, Calif., US #12888). Standard curves were constructed using dilution series of the bacterial strains representative of each group. Samples and standards were run in triplicate by absolute quantification on the Roche LightCycler® 480 real-time PCR instrument. Roche SYBR Green I Master Mix (04707516001) detection chemistry was used to detect double stranded DNA amplification. Total reaction volume was 20 μL, consisting of 10 μL SyBr Green I Master mix, 4 μL forward primer (5× concentrated at 2.5 μM), 4 μL reverse primer (5× concentrated at 2.5 μM) and 2 μL DNA template or sterile water (no template control).

Each qPCR run included one activation cycle (95° C.) for 5 min, 32-40 run cycles (including the denaturation step at 95° C. (30 s), annealing step as in Table 14 and extension step at 72° C. for 1 min), and one melt curve cycle (60 to 95° C. at 0.1° C. per second with continuous fluorescence acquisition) followed by a cooling cycle at 40° C. The melt curve Tm calling cycle enabled the differentiation between target product and non-specific double stranded product such as primer-dimers. Primers were diluted in PCR grade Statistical calculations were conducted in R using the stats package (R Development Core Team 2008). The Wilcoxon Signed Rank test was performed to assess significant differences before and after each treatment. For the in vitro fermentations, significant differences were determined by comparing time 0 with the other time points. A P value of less than 0.05 was deemed significant after correcting for multiple comparisons using the False Discovery Rate (FDR) method in the p.adjust function in R Studio (Benjamini & Hochberg 1995).

Example 10

Results of qPCR Analysis of Microbiome in the Human Clinical Trial

The results of the qPCR data portray a relatively stable microbial profile over time for each bacterial group assessed. Moderate increases or decreases were observed after each treatment. Table 15 depicts LightCycler® 480 qPCR data displaying bacterial groups as the calculated average 16S rRNA gene copy number/gram faecal sample (LOG transformed) and standard error of the mean (SEM) before and after each treatment period in the healthy group. Table 16 depicts LightCycler® 480 qPCR data displaying bacterial groups as the calculated average 16S rRNA gene copy number/gram faecal sample (LOG transformed) and standard error of the mean (SEM) before and after each treatment period in the functionally constipated group.

Figure 6:
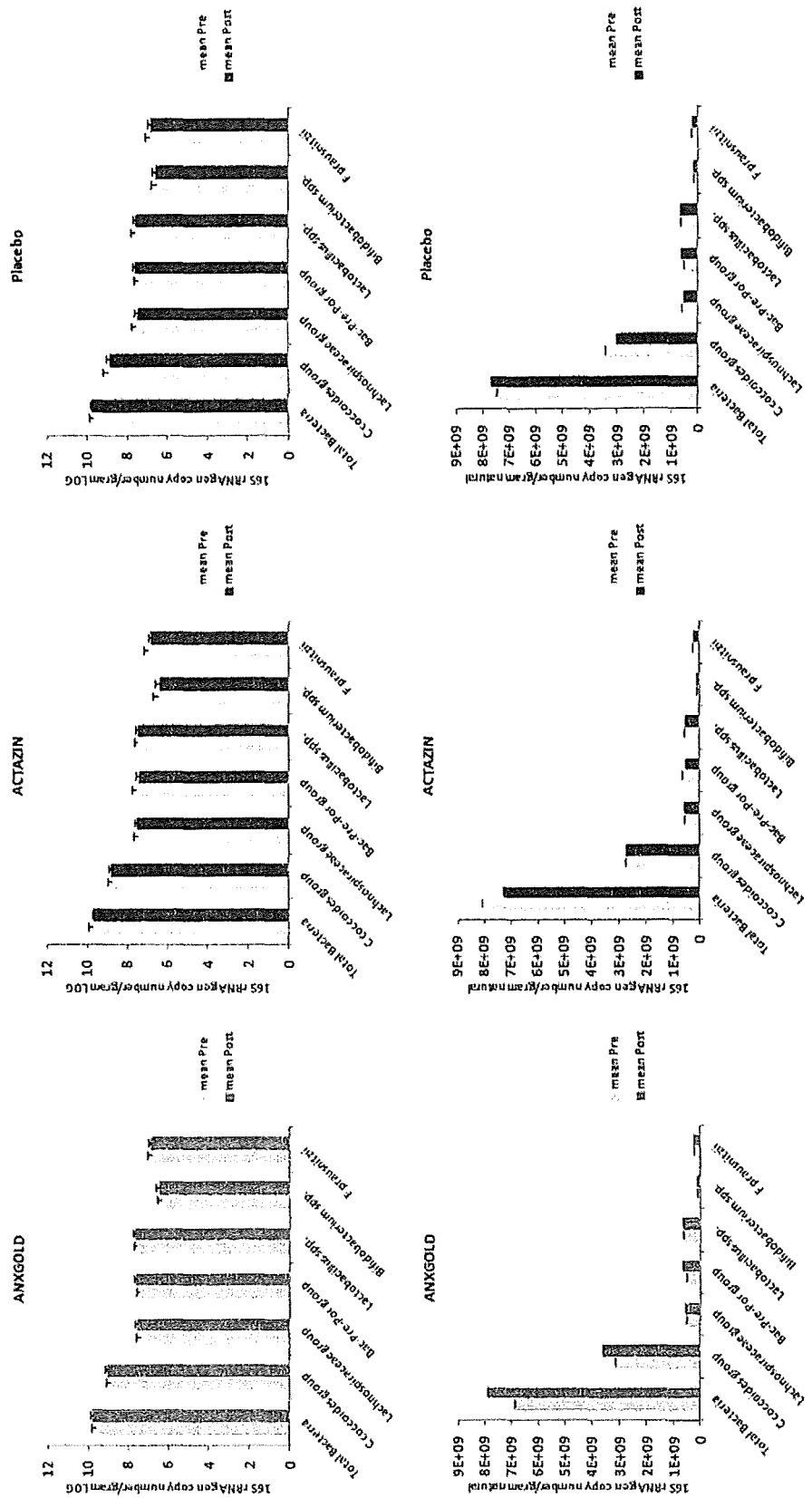
FIG. 6: LightCycler® 480 qPCR data displaying bacterial groups as the calculated average 16S rRNA gene copy number/gram faecal sample (top row LOG transformed, bottom row natural data) and standard error of the mean (SEM) as error bars before and after each treatment period in the healthy group.

As shown in Table 15 and FIG. 6, in the healthy group after GOLD treatment, moderate increases were observed in the total bacteria, C. coccoides, Lachnospiraceae, Lactobacilli, Bifidobacteria and Bacteroides-Prevotella-Porphyromonas groups, whereas the concentration of F. prausnitzii remained constant. With ACTAZIN™ supplementation, slight decreases were seen in the total bacteria, Bacteroides-Prevotella-Porphyromonas, Lactobacilli, Bifidobacteria, and F. prausnitzii groups, whereas the C. coccoides group remained constant and the Lachnospiraceae group increased slightly. The placebo treatment saw elevated concentrations of total bacteria and Bacteroides-Prevotella-Porphyromonas and small decreases in concentrations of the C. coccoides, Lachnospiraceae, Lactobacilli, Bifidobacteria, and F. prausnitzii groups.

Figure 5C:
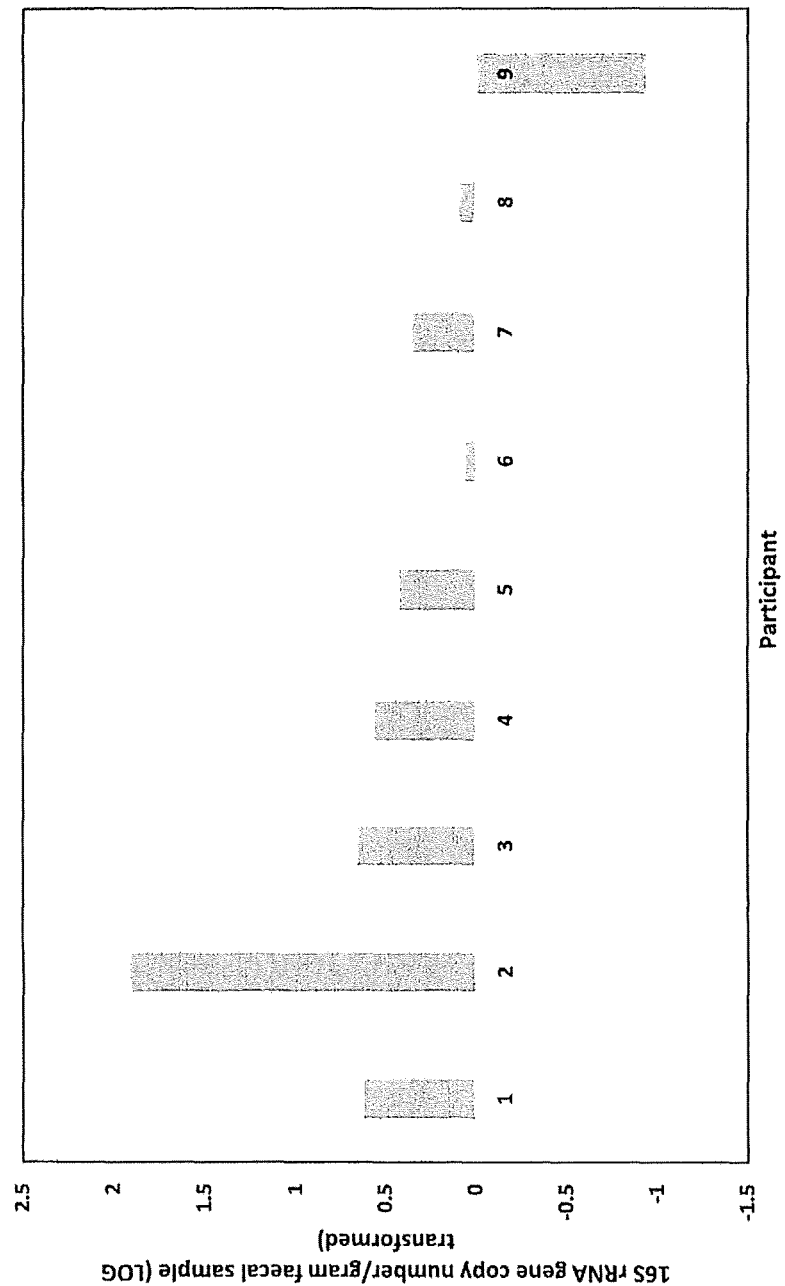
FIG. 5C: Quantitative PCR data (LOG transformed) showing net difference in *Faecalibacterium prausnitzii* levels in functionally constipated participants after GOLD (Gold3) treatment.
Figure 7:
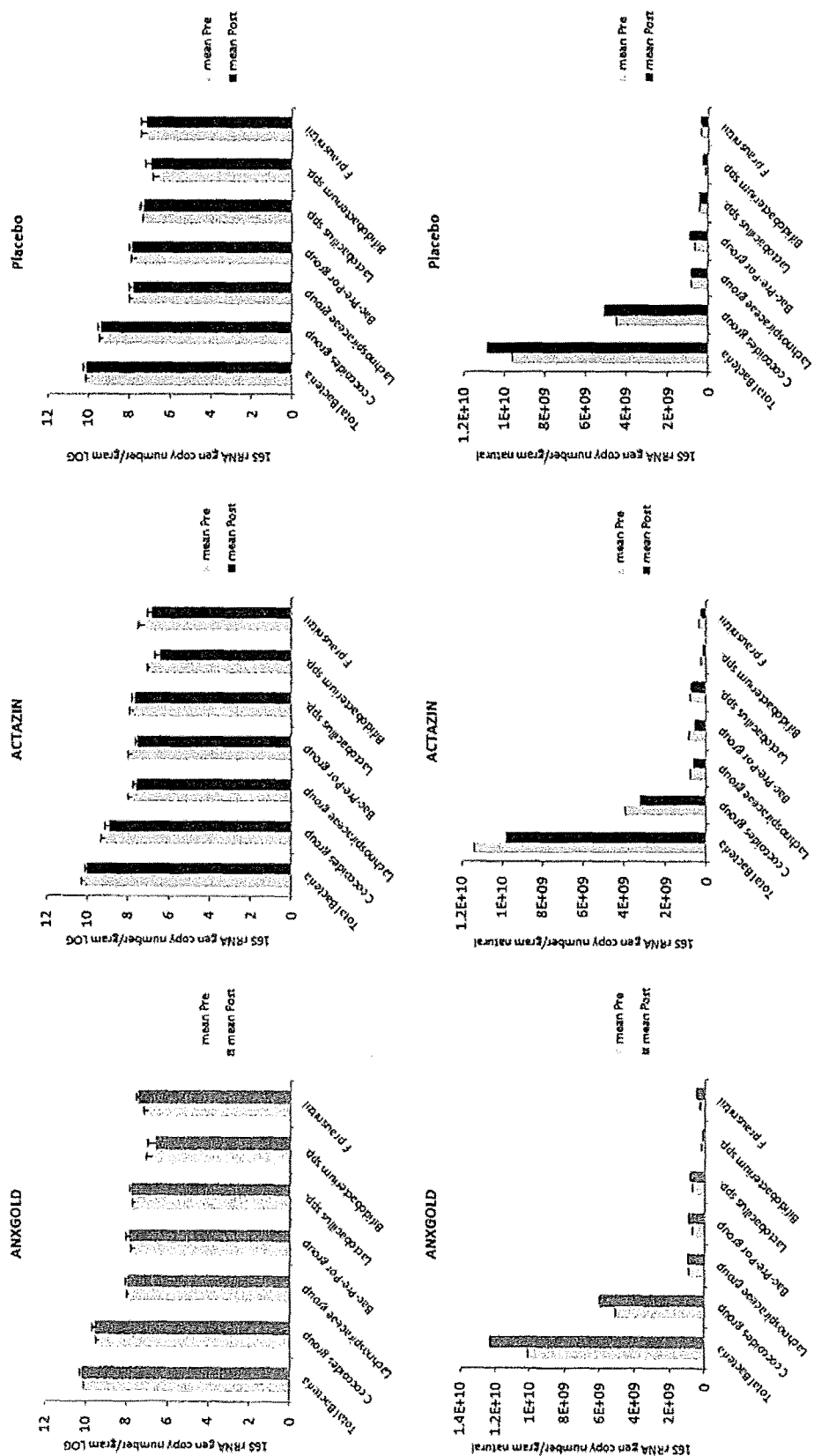
FIG. 7: LightCycler® 480 qPCR data displaying bacterial groups as the calculated average 16S rRNA gene copy number/gram faecal sample (top row LOG transformed, bottom row natural data) and standard error of the mean (SEM) before and after each treatment period in the functionally constipated group.

As shown in Table 16 and FIG. 7, in the functionally constipated group after GOLD treatment, moderate increases were observed in the total bacteria, Clostridium coccoides, Lachnospiraceae, Bacteroides-Prevotella-Porphyromonas, and Lactobacilli groups, and a minor decrease in Bifidobacterium spp. The concentration of F. prausnitzii increased the most from log 7.03 to 7.45 which almost reached significance (P=0.0503) and concurs with a similar rise reported in the 16S rRNA gene sequencing data. The increase in actual numbers is 231.9 million 16S rRNA gene copy numbers, which is a 179% increase after GOLD treatment. After ACTAZIN™ treatment, decreases were observed in the all bacterial groups. Eight out of nine of the functionally constipated participants showed an increase in F. prausnitzii levels following GOLD treatment. See FIG. 5C, The placebo treatment saw elevated concentrations in all bacterial groups except for Lachnospiraceae which remained constant.

TABLE 15

LightCycler® 480 qPCR data for the healthy group

|  | mean Pre | SEM Pre | mean Post | SEM Post | p value | fdr p value |
|---|---|---|---|---|---|---|
| GOLD | | | | | | |
| Total Bacteria | 9.63 | 0.17 | 9.77 | 0.09 | 0.99 | 1.00 |
| Clostridium coccoides group | 8.91 | 0.21 | 9.03 | 0.15 | 0.84 | 1.00 |
| Lachnospiraceae group | 7.42 | 0.18 | 7.53 | 0.12 | 0.81 | 1.00 |
| Bacteroides-Prevotella-Porphyromonas group | 7.44 | 0.17 | 7.59 | 0.13 | 0.44 | 0.88 |
| Lactobacillus spp. | 7.59 | 0.14 | 7.63 | 0.13 | 0.95 | 1.00 |
| Bifidobacterium spp. | 6.36 | 0.23 | 6.42 | 0.19 | 0.99 | 1.00 |
| Faecalibacterium prausnitzii | 6.87 | 0.18 | 6.87 | 0.13 | 0.72 | 1.00 |
| ACTAZIN™ | | | | | | |
| Total Bacteria | 9.79 | 0.09 | 9.69 | 0.17 | 0.98 | 1.00 |
| Clostridium coccoides group | 8.79 | 0.11 | 8.79 | 0.22 | 0.56 | 1.00 |
| Lachnospiraceae group | 7.51 | 0.08 | 7.52 | 0.12 | 0.91 | 1.00 |
| Bacteroides-Prevotella-Porphyromonas group | 7.6 | 0.1 | 7.43 | 0.16 | 0.60 | 1.00 |
| Lactobacillus spp. | 7.53 | 0.07 | 7.44 | 0.14 | 0.91 | 1.00 |
| Bifidobacterium spp. | 6.49 | 0.18 | 6.41 | 0.24 | 0.90 | 1.00 |
| Faecalibacterium prausnitzii | 6.97 | 0.12 | 6.78 | 0.21 | 0.31 | 0.62 |
| Placebo | | | | | | |
| Total Bacteria | 9.71 | 0.17 | 9.74 | 0.1 | 0.82 | 1.00 |
| Clostridium coccoides group | 8.98 | 0.22 | 8.87 | 0.19 | 0.35 | 0.70 |
| Lachnospiraceae group | 7.56 | 0.2 | 7.47 | 0.15 | 0.51 | 1.00 |
| Bacteroides-Prevotella-Porphyromonas group | 7.47 | 0.18 | 7.56 | 0.14 | 0.87 | 1.00 |
| Lactobacillus spp. | 7.62 | 0.19 | 7.6 | 0.13 | 0.66 | 1.00 |
| Bifidobacterium spp. | 6.59 | 0.22 | 6.55 | 0.18 | 0.56 | 1.00 |
| Faecalibacterium prausnitzii | 6.91 | 0.21 | 6.83 | 0.17 | 0.60 | 1.00 |

TABLE 16

LightCycler® 480 qPCR data for the functionally constipated group

|  | mean Pre | SEM Pre | mean Post | SEM Post | p value | fdr p value |
|---|---|---|---|---|---|---|
| GOLD | | | | | | |
| Total Bacteria | 10.01 | 0.09 | 10.21 | 0.07 | 0.16 | 0.32 |
| Clostridium coccoides group | 9.35 | 0.17 | 9.5 | 0.16 | 0.86 | 1.00 |
| Lachnospiraceae group | 7.85 | 0.11 | 7.96 | 0.11 | 1.00 | 1.00 |
| Bacteroides-Prevotella-Porphyromonas group | 7.65 | 0.15 | 7.88 | 0.15 | 0.22 | 0.44 |
| Lactobacillus spp. | 7.64 | 0.11 | 7.79 | 0.07 | 0.49 | 0.98 |
| Bifidobacterium spp. | 6.76 | 0.3 | 6.64 | 0.35 | 0.80 | 1.00 |
| Faecalibacterium prausnitzii | 7.03 | 0.16 | 7.45 | 0.13 | 0.05 | 0.10 |
| ACTAZIN™ | | | | | | |
| Total Bacteria | 10.13 | 0.15 | 9.98 | 0.11 | 0.34 | 0.68 |
| Clostridium coccoides group | 9.11 | 0.2 | 8.93 | 0.19 | 0.60 | 1.00 |
| Lachnospiraceae group | 7.78 | 0.19 | 7.56 | 0.17 | 0.55 | 1.00 |
| Bacteroides-Prevotella-Porphyromonas group | 7.82 | 0.17 | 7.5 | 0.13 | 0.16 | 0.32 |

TABLE 16-continued

LightCycler ® 480 qPCR data for the functionally constipated group

|  | mean Pre | SEM Pre | mean Post | SEM Post | p value | fdr p value |
|---|---|---|---|---|---|---|
| Lactobacillus spp. | 7.75 | 0.15 | 7.67 | 0.12 | 0.73 | 1.00 |
| Bifidobacterium spp. | 6.95 | 0.15 | 6.43 | 0.27 | 0.22 | 0.44 |
| Faecalibacterium prausnitzii | 7.19 | 0.29 | 6.86 | 0.2 | 0.33 | 0.66 |
| Placebo | | | | | | |
| Total Bacteria | 9.96 | 0.16 | 10.08 | 0.12 | 0.49 | 0.98 |
| Clostridium coccoides group | 9.23 | 0.2 | 9.35 | 0.17 | 0.60 | 1.00 |
| Lachnospiraceae group | 7.8 | 0.17 | 7.8 | 0.17 | 1.00 | 1.00 |
| Bacteroides-Prevotella-Porphyromonas group | 7.65 | 0.24 | 7.84 | 0.15 | 0.49 | 0.98 |
| Lactobacillus spp. | 7.24 | 0.1 | 7.29 | 0.12 | 0.93 | 1.00 |
| Bifidobacterium spp. | 6.53 | 0.32 | 6.93 | 0.26 | 0.26 | 0.52 |
| Faecalibacterium prausnitzii | 7.12 | 0.29 | 7.16 | 0.26 | 0.73 | 1.00 |

FIGS. 6 and 7 display the bacterial concentration data graphically in both the log transformed and natural data forms for the healthy and functionally constipated groups, respectively. Viewing the data in this form highlights how stable the composition of the faecal microbiota is over time.

It is noted that bacteria in the *Bacteroides-Prevotella-Porphyromonas* group constitute a considerable collection of primary degraders in the human colonic community. They play an important role in accessing unabsorbed carbohydrate using specialised scavenging mechanisms. Principal among these are cellulose, starch, inulin and xylan degraders such as *Bacteroides* thetaiotaomicron, *Bacteroides ovatus*, and *Bacteroides cellulosilyticus* (Flint et al. 2008; Walker et al. 2008). *Roseburia intestinalis, Roseburia inulinovorans, Ruminococcus bromii*, and *Ruminococcus flavefaciens* are also key primary degraders that are members of the *C. coccoides* group (Kurakawa et al. 2015).

The *C. coccoides* group constitutes the largest bacterial subgroup in the colon, typically making up 25-60% of total bacterial abundance (Hold et al. 2002) and are composed of a large proportion of butyrate producers (Louis & Flint 2009). Two principal microorganisms with proven probiotic status are *Bifidobacteria* and *Lactobacilli*. *Bifidobacteria* have often been associated with healthy microbiota and are acetate producers, which can have beneficial effects on host health. *Lactobacilli* consist of a group of lactic acid commensal bacteria that have been exploited for centuries in dairy product production and have been studied in hundreds of trials with respect to their probiotic efficacy (Reid 1999).

The increase in *F. prausnitzii* concentration was just short of being significant (P=0.0503) after the 4 week period of supplementation with the Gold3 gold-kiwifruit-based GOLD. *F. prausnitzii* is one of the most populous species in the human gastrointestinal tract, being typically observed at over 5% of the total proportion of the colonic microbiota of healthy adults (Miquel et al. 2013). Members of the *Firmicutes phylum, F. prausnitzii* are commensal inhabitants of the human large bowel, with demonstrated anti-inflammatory properties in vivo (Furet et al. 2010; Sokol et al. 2009). *F. prausnitzii* generate butyrate as a result of carbohydrate fermentation, as well as lactate and formate (Duncan et al. 2002; Duncan et al. 2004). Butyrate is the preferred energy source for colonic epithelial cells and plays a role in alleviating inflammation as well as mitigating carcinogenesis, pathogenic colonisation, and oxidative stress (Hamer et al. 2008; Macfarlane & Macfarlane 2011). GOLD selectively stimulates the proliferation of the commensal *F. prausnitzii* and therefore may be considered as helpful for inflammation-related gastrointestinal disorders.

In summary, qPCR data confirms the microbial relative abundance data and shows that the Gold3 gold-kiwifruit-derived supplement has increased the concentration of *F. prausnitzii* in functionally constipated participants. This demonstrates a beneficial outcome as *F. prausnitzii* is known to grow in the large bowel and generate butyrate which has protective functions/health benefits in the gut.

These results are considered as significant, given that *F. prausnitzii* is highly sensitive to oxygen (Rigottier-Gois 2013), and therefore challenging for formulation and storage as a probiotic agent. Therefore, the gold kiwifruit compositions of the invention provide an efficient and effective means for increasing *F. prausnitzii* levels, which would be otherwise difficult to modulate.

Persons of ordinary skill can utilise the disclosures and teachings herein to produce other embodiments and variations without undue experimentation. All such embodiments and variations are considered to be part of this invention.

Accordingly, one of ordinary skill in the art will readily appreciate from the disclosure that later modifications, substitutions, and/or variations performing substantially the same function or achieving substantially the same result as embodiments described herein may be utilised according to such related embodiments of the present invention. Thus, the invention is intended to encompass, within its scope, the modifications, substitutions, and variations to processes, manufactures, compositions of matter, compounds, means, methods, and/or steps disclosed herein.

REFERENCES

Abdollahi-Roodsaz S, Joosten L A, Koenders M I, Devesa I, Roelofs M F, Radstake T R, Heuvelmans-Jacobs M, Akira S, Nicklin M J, Ribeiro-Dias F, van den Berg W B 2008. Stimulation of TLR2 and TLR4 differentially skews the balance of T cells in a mouse model of arthritis. Journal of Clinical Investigation 118(1): 205-16.

Abrahamsson T R, Jakobsson H E, Andersson A F, Bjorksten B, Engstrand L, Jenmalm M C 2012. Low diversity of the gut microbiota in infants with atopic eczema. J Allergy Clin Immunol 129(2): 434-40, 440 e1-2.

Adaim A. 2010. Investigating the effect of gold kiwifruit consumption on the incidence and symptoms of upper respiratory tract infections in preschool children: a thesis presented in partial fulfillment of the requirements for the degree of Masters of Sciences in Human Nutrition and Human Health, Massey University, Auckland, New Zealand.

Attaluri A, Donahoe R, Valestin J, Brown K, Rao S S C 2011. Randomised clinical trial: dried plums (prunes) vs. psyllium for constipation. Alimentary Pharmacology & Therapeutics 33(7): 822-828.

Bach Knudsen K E, Jorgensen H, Canibe N. Quantification of the absorption of nutrients derived from carbohydrate assimilation: model experiment with catheterized pigs fed on wheat- or oat-based rolls. The British Journal of Nutrition. 2000; 84: 449-58.

Backhed F, Ley R E, Sonnenburg J L, Peterson D A, Gordon J I. Host-bacterial mutualism in the human intestine. Science. 2005; 307: 1915-20.

Benjamini Y, Hochberg Y. Controlling the false discovery rate—a practical and powerful approach to multiple testing. Journal of the Royal Statistical Society Series B-Methodological. 1995; 57: 289-300.

Belenguer A, Holtrop G, Duncan S H, Anderson S E, Calder A G, Flint H J, et al. Rates of production and utilization of lactate by microbial communities from the human colon. FEMS Microbiol. Ecol. 2011; 77: 107-19.

Bentley-Hewitt K L, Blatchford P A, Parkar S G, Ansell J, Pernthaner A. Digested and fermented green kiwifruit increases human beta-defensin 1 and 2 production in vitro. Plant Foods for Human Nutrition. 2012; 67: 208-14.

Blatchford P, Bentley-Hewitt K L, Stoklosinski H, McGhie T, Gearry R, Gibson G, Ansell J 2015a. In vitro characterisation of the fermentation profile and prebiotic capacity of gold-fleshed kiwifruit. Benef Microbes pages 1-12. Published online at DOI: http://dx.doi.org/10.3920/BM2015.0006.

Blatchford P, Stoklosinski H, Walton G, Swann J, Gibson G, Gearry R, Ansell J 2015b. Kiwifruit fermentation drives positive gut microbial and metabolic changes irrespective of initial microbiota composition. Bioactive Carbohydrates and Dietary Fibre 6(1): 37-45.

Boland, M. J., Hardman, M. J. 1972, Kinetic studies on the thiol protease from *Actinidia chinensis*. FEBS Letters, 27(2): 282-284.

Bravo J A, Forsythe P, Chew M V, Escaravage E, Savignac H M, Dinan T G, et al. Ingestion of *Lactobacillus* strain regulates emotional behavior and central GABA receptor expression in a mouse via the vagus nerve. Proceedings of the National Academy of Sciences of the United States of America. 2011; 108: 16050-5.

Buffie C G, Pamer E G. Microbiota-mediated colonization resistance against intestinal pathogens. Nature Reviews Immunology. 2013; 13: 790-801.

Candela M, Rampelli S, Turroni S, Severgnini M, Consolandi C, De Bellis G, et al. Unbalance of intestinal microbiota in atopic children. BMC Microbiology. 2012; 12: 95.

Caporaso J G, Bittinger K, Bushman F D, DeSantis T Z, Andersen G L, Knight R. PyNAST: a flexible tool for aligning sequences to a template alignment. Bioinformatics. 2010; 26: 266-7.

Caporaso J G, Kuczynski J, Stombaugh J, Bittinger K, Bushman F D, Costello E K, et al. QIIME allows analysis of high-throughput community sequencing data. Nature Methods. 2010; 7: 335-6.

Caporaso J G, Lauber C L, Walters W A, Berg-Lyons D, Lozupone C A, Turnbaugh P J, et al. Global patterns of 16S rRNA diversity at a depth of millions of sequences per sample. Proceedings of the National Academy of Sciences of the United States of America. 2011; 108 Suppl 1: 4516-22.

Cardona F, Andres-Lacueva C, Tulipani S, Tinahones F J, Queipo-Ortuno M I. 2013. Benefits of polyphenols on gut microbiota and implications in human health. Journal of Nutritional Biochemistry, 24: 1415-1422, Chan A O, Leung G, Tong T, Wong N Y. Increasing dietary fiber intake in terms of kiwifruit improves constipation in Chinese patients. World Journal of Gastroenterology: WJG. 2007; 13: 4771-5.

Chang C, Lin T, Lu Y, Liu T, Liu J. 2010. Kiwifruit improves bowel function in patients with irritable bowel syndrome with constipation. Asia Pacific Journal of Clinical Nutrition 19(4): 451-457.

Chassard, C, Dapoigny, M, Scott, K P, Crouzet, L, Del'homme, C, Marquet, P, Martin, J C, Pickering, G, Ardid, D, Eschalier, A, Dubray, C, Flint, H J and Bernalier-Donadille, A. 2012. Functional dysbiosis within the gut microbiota of patients with constipated-irritable bowel syndrome. Alimentary Pharmacology & Therapeutics 35: 828-838.

Chen W, Liu F, Ling Z, Tong X, Xiang C 2012. Human intestinal lumen and mucosa-associated microbiota in patients with colorectal cancer. PloS One 7(6): e39743.

DeSantis T Z, Hugenholtz P, Larsen N, Rojas M, Brodie E L, Keller K, et al. Greengenes, a chimera-checked 16S rRNA gene database and workbench compatible with ARB. Appl. Environ. Microbiol. 2006; 72: 5069-72.

de Sousa Moraes L F, Grzeskowiak L M, de Sales Teixeira T F, Gouveia Peluzio Mdo C 2014. Intestinal microbiota and probiotics in celiac disease. Clinical Microbiology Reviews 27(3): 482-9.

de Vos W M, de Vos E A 2012. Role of the intestinal microbiome in health and disease: from correlation to causation. Nutrition Reviews 70 Suppl 1: S45-56.

de Weerth C, Fuentes S, Puylaert P, de Vos W M 2013. Intestinal microbiota of infants with colic: development and specific signatures. Pediatrics 131(2): e550-8.

Desbonnet L, Garrett L, Clarke G, Bienenstock J, Dinan T G 2008. The probiotic *Bifidobacteria infantis*: An assessment of potential antidepressant properties in the rat. Journal of Psychiatric Research 43(2): 164-74.

Drossman D A. The functional gastrointestinal disorders and the Rome III process. Gastroenterology. 2006; 130: 1377-90.

Drummond L. 2013. The composition and nutritional value of kiwifruit. Advances in Food and Nutrition Research 68: 33-57, Drummond L, Gearry R B. 2013. Kiwifruit modulation of gastrointestinal motility. Advances in Food and Nutrition Research 68: 219-232.

Duncan S H, Hold G L, Harmsen H-J, Stewart C S, Flint H J. Growth requirements and fermentation products of *Fusobacterium prausnitzii*, and a proposal to reclassify it as *Faecalibacterium prausnitzii* gen. nov., comb. nov. International Journal of Systematic and Evolutionary Microbiology. 2002; 52: 2141-6.

Duncan S H, Louis P, Flint H J. Lactate-utilizing bacteria, isolated from human feces, that produce butyrate as a major fermentation product. Appl. Environ. Microbiol. 2004; 70: 5810-7.

Edgar R C. Search and clustering orders of magnitude faster than BLAST. Bioinformatics. 2010; 26: 2460-1.

Egert M, de Graaf A A, Smidt H, de Vos W M, Venema K. Beyond diversity: functional microbiomics of the human colon. Trends in Microbiology. 2006; 14: 86-91.

Eidenberger T, Selg M, Fuerst S, Krennhuber K. 2014. In-vitro inhibition of human lipase PS by polyphenols from kiwi fruit. Journal of Food Research. 3(4): 71-77.

Ferguson A R, Ferguson L R. Are kiwifruit really good for you? In: Huang H W, editor. Proceedings of the Fifth International Symposium on Kiwifruit. 2003. 131-8.

Flint H J, Bayer E A, Rincon M T, Lamed R, White B A 2008. Polysaccharide utilization by gut bacteria: potential for new insights from genomic analysis. Nat Rev Microbiol 6(2): 121-31.

Fu C J, Carter J N, Li Y, Porter J H, Kerley M S 2006. Comparison of agar plate and real-time PCR on enumeration of *Lactobacillus, Clostridium perfringens* and total anaerobic bacteria in dog faeces. Letters in Applied Microbiology 42(5): 490-494.

Fujimoto T, Imaeda H, Takahashi K, Kasumi E, Bamba S, Fujiyama Y, Andoh A 2013. Decreased abundance of *Faecalibacterium prausnitzii* in the gut microbiota of Crohn's disease. J Gastroenterol Hepatol 28(4): 613-9.

Furet J P, Kong L C, Tap J, Poitou C, Basdevant A, Bouillot J L, et al. Differential adaptation of human gut microbiota to bariatric surgery-induced weight loss: links with metabolic and low-grade inflammation markers, Diabetes. 2010; 59: 3049-57.

Gibson G R, Scott K P, Rastall R A, Tuohy K M, Hotchkiss A, Dubert-Ferrandon A, Gareau M, Murphy E F, Sulnier D, Loh G, MacFarlane S, Delzenne N, Ringel Y, Kozianowski G, Dickmann R, Lenoir-Wijnkoop I, Walker C, Buddington R. 2010. Dietary prebiotics: current status and new definition. Food Science and Technology Bulletin: Functional Foods, 7: 1-19.

Geurts L, Neyrinck A M, Delzenne N M, Knauf C, Cani P D. Gut microbiota controls adipose tissue expansion, gut barrier and glucose metabolism: novel insights into molecular targets and interventions using prebiotics, Beneficial Microbes. 2014; 5: 3-17.

Gostner A, Blaut M, Schiffer V, Kozianowski G, Theis S, Klingeberg M, et al. Effect of isomalt consumption on faecal microflora and colonic metabolism in healthy volunteers. Br. J. Nutr. 2006; 95: 40-50.

Guidance for industry: irritable bowel syndrome—clinical evaluation of drugs for treatment. U.S. Department of Health and Human Services. Food and Drug Administration. Center for Drug Evaluation and Research. http://www.fda.gov/downloads/Drugs/Guidances/UCM205269.pdf Hamer H M, Jonkers D, Venema K, Vanhoutvin S, Troost F J, Brummer R J. Review article: The role of butyrate on colonic function. Aliment. Pharmacol. Ther. 2008; 27: 104-19.

Hazenberg M P, van de Merwe J P, Pena A S, Pennock-Schroder A M, van Lieshout L M. Antibodies to *Coprococcus comes* in sera of patients with Crohn's disease. Isolation and purification of the agglutinating antigen tested with an ELISA technique. Journal of Clinical & Laboratory Immunology. 1987; 23: 143-8.

Herlemann D P R, Labrenz M, Juergens K, Bertilsson S, Waniek J J, Andersson A F. Transitions in bacterial communities along the 2000 km salinity gradient of the Baltic Sea. ISME Journal. 2011; 5: 1571-9.

Hold G L, Pryde S E, Russell V J, Furrie E, Flint H J 2002. Assessment of microbial diversity in human colonic samples by 16S rDNA sequence analysis. FEMS Microbiol Ecol 39(1): 33-9.

Huda-Faujan N, Abdulamir A S, Fatimah A B, Anas O M, Shuhaimi M, Yazid A M, et al. The impact of the level of the intestinal short chain fatty acids in inflammatory bowel disease patients versus healthy subjects. The Open Biochemistry Journal. 2010; 4: 53-8.

Hudcovic T, Kolinska J, Klepetar J, Stepankova R, Rezanka T, Srutkova D, et al. Protective effect of *Clostridium tyrobutyricum* in acute dextran sodium sulphate-induced colitis: differential regulation of tumour necrosis factor-alpha and interleukin-18 in BALB/c and severe combined immunodeficiency mice. Clinical and Experimental Immunology. 2012; 167: 356-65.

Husebye E, Hellström P M, Sundler F, Chen J, and Midtvedt T. 2001. Influence of microbial species on small intestinal myoelectric activity and transit in germ-free rats. American Journal of Physiology, Gastrointestinal and Liver Physiology 280: G368-G380.

Hunter D C, Skinner M A, Wolber F M, Booth C L, Loh J M S, Wohlers M, Stevenson L M, Kruger M C. 2012. Consumption of gold kiwifruit reduces severity and duration of selected upper respiratory tract infection symptoms and increases plasma vitamin C concentration in healthy older adults. British Journal of Nutrition 108: 1235-1245.

Jeffery I B, O'Toole P W, Ohman L, Claesson M J, Deane J, Quigley E M, Simren M 2012. An irritable bowel syndrome subtype defined by species-specific alterations in faecal microbiota. Gut 61(7): 997-1006.

Kalliomaki M, Satokari R, Lahteenoja H, Vahamiko S, Gronlund J, Routi T, Salminen S 2012. Expression of microbiota, Toll-like receptors, and their regulators in the small intestinal mucosa in celiac disease. Journal of Pediatric Gastroenterology and Nutrition 54(6): 727-32.

L Kaur, S M Rutherfurd, P J Moughan, L Drummond, and M J Boland. 2010. Actinidin enhances protein digestion in the small intestine as assessed using an in vitro digestion model, J. Agric. Food Chem. 58 (8): 5074-5080.

Khalif I L, Quigley E M M, Konovitch E A and Maximova I D. 2005. Alterations in the colonic flora and intestinal permeability and evidence of immune activation in chronic constipation. Digestive and Liver Disease 37: 838-849.

Koeth R A, Wang Z, Levison B S, Buffa J A, Org E, Sheehy B T, Britt E B, Fu X, Wu Y, Li L, Smith J D, DiDonato J A, Chen J, Li H, Wu G D, Lewis J D, Warrier M, Brown J M, Krauss R M, Tang W H, Bushman F D, Lusis A J, Hazen S L 2013. Intestinal microbiota metabolism of L-carnitine, a nutrient in red meat, promotes atherosclerosis. Nature Medicine 19(5): 576-85.

Kok R G, DeWaal A, Schut F, Welling G W, Weenk G, Hellingwerf K J 1996. Specific detection and analysis of a probiotic *Bifidobacterium* strain in infant feces. Applied and Environmental Microbiology 62(10): 3668-3672.

Kolida S, Gibson G R. 2007. Prebiotic capacity of inulin-type fructans. The Journal of Nutrition, 137(11): 2503S-2506S.

Kolida S, Meyer D, Gibson G R. A double-blind placebo-controlled study to establish the bifidogenic dose of inulin in healthy humans. Eur. J. Clin. Nutr. 2007; 61: 1189-95.

Koren O, Spor A, Felin J, Fak F, Stombaugh J, Tremaroli V, Behre C J, Knight R, Fagerberg B, Ley R E, Backhed F 2011. Human oral, gut, and plaque microbiota in patients with atherosclerosis. Proceedings of the National Academy of Sciences of the United States of America 108 Suppl 1: 4592-8.

Kurakawa T, Ogata K, Matsuda K, Tsuji H, Kubota H, Takada T, Kado Y, Asahara T, Takahashi T, Nomoto K 2015. Diversity of Intestinal *Clostridium coccoides* group in the Japanese population, as demonstrated by reverse transcription-quantitative PCR. PLoS One 10(5): e0126226.

Leahy S C, Kelly W J, Altermann E, Ronimus R S, Yeoman C J, Pacheco D M, Li D, Kong Z, McTavish S, Sang C, Lambie S C, Janssen P H, Dey D, Attwood G T 2010. The genome sequence of the rumen methanogen *Methanobrevibacter ruminantium* reveals new possibilities for controlling ruminant methane emissions. PLoS One 5(1).

Lee Y K, Menezes J S, Umesaki Y, Mazmanian S K 2011. Proinflammatory T-cell responses to gut microbiota promote experimental autoimmune encephalomyelitis. Proceedings of the National Academy of Sciences of the United States of America 108 Suppl 1: 4615-22.

Lepage P, Hasler R, Spehlmann M E, Rehman A, Zvirbliene A, Begun A, Ott S, Kupcinskas L, Dore J, Raedler A, Schreiber S 2011. Twin study indicates loss of interaction between microbiota and mucosa of patients with ulcerative colitis. Gastroenterology 141(1): 227-36.

Leung L, Riutta T, Kotecha J, Rosser W. 2011. Chronic constipation: An evidence-based review. The Journal of the American Board of Family Medicine 24(4): 436-451.

Ley R E, Tumbaugh P J, Klein S, Gordon J I 2006. Microbial ecology—Human gut microbes associated with obesity. Nature 444(7122): 1022-1023.

Liu L W C. 2011. Chronic constipation: current treatment options. Canadian Journal of Gastroenterology 25(Suppl B): 22B-28B.

Louis P, Flint H J 2009. Diversity, metabolism and microbial ecology of butyrate-producing bacteria from the human large intestine. FEMS Microbiol Lett 294(1): 1-8.

Maccaferri S, Candela M, Turroni S, Centanni M, Severgnini M, Consolandi C, Cavina P, Brigidi P 2012. IBS-associated phylogenetic unbalances of the intestinal microbiota are not reverted by probiotic supplementation. Gut Microbes 3(5): 406-13.

Macfarlane G T, Macfarlane S. Fermentation in the human large intestine: its physiologic consequences and the potential contribution of prebiotics. J. Clin. Gastroenterol. 2011; 45 Suppl: S120-7.

R Maddumage, N J Nieuwenhuizen, S M Bulley, J M Cooney, S A Green, R G Atkinson. 2013. Diversity and relative levels of actinidin, kiwellin, and thaumatin-like allergens in 15 varieties of kiwifruit (*Actinidia*). J. Agric. Food Chem. 61: 728-739.

Masella A P, Bartram A K, Truszkowski J M, Brown D G, Neufeld J D. PANDAseq: PAired-eND Assembler for Illumina sequences. BMC Bioinformatics. 2012; 13:31.

Matsuki T, Watanabe K, Fujimoto J, Miyamoto Y, Takada T, Matsumoto K, Oyaizu H, Tanaka R 2002. Development of 16S rRNA-gene-targeted group-specific primers for the detection and identification of predominant bacteria in human feces. Appl Environ Microbiol 68(11): 5445-51.

Metcalf A M, Phillips S F, Zinsmeister A R, MacCarty R L, Beart R W, Wolff B G. Simplified assessment of segmental colonic transit. Gastroenterology. 1987; 92: 40-7.

Millet S, Van Oeckel M J, Aluwe M, Delezie E, De Brabander D L. Prediction of in vivo short-chain fatty acid production in hindgut fermenting mammals: problems and pitfalls. Crit. Rev. Food Sci. Nutr. 2010; 50:605-19.

Miquel S, Martin R, Rossi O, Bermudez-Humaran L G, Chatel J M, Sokol H, et al. *Faecalibacterium prausnitzii* and human intestinal health. Current Opinion in Microbiology. 2013; 16: 255-61.

Monro J A, Mishra S, Venn B. 2010. Baselines representing blood glucose clearance improve in vitro prediction of the glycemic impact of customarily consumed food quantities. British Journal of Nutrition, 103(2): 295-305.

Murata Y, Ohmori H, Ichikawa M, Harada A, Agari M, Fukuba H, Yamasaki M, Yasuzawa M, Takemoto M, Ikeda M, Matsumoto N, Tamura T, Sumimoto R, Namba K 2013. Fecal microbiota and fecal characteristics of patients with Parkinson's disease. Journal of Intestinal Microbiology 27(4): 211-215.

Nadkarni M A, Martin F E, Jacques N A, Hunter N 2002. Determination of bacterial load by real-time PCR using a broad-range (universal) probe and primers set. Microbiology-Sgm 148: 257-266.

Neufeld K M, Kang N, Bienenstock J, Foster J A 2011. Reduced anxiety-like behavior and central neurochemical change in germ-free mice. Neurogastroenterology and Motility 23(3): 255-64, e119.

N J Nieuwenhuizen, R Maddumage, G K Tsang, L G Fraser, J M Cooney, H N De Silva, S Green, K A Richardson, R G Atkinson. 2012. Mapping, complementation, and targets of the cysteine protease actinidin in kiwifruit. Plant Physiology 158(1): 376-388.

Parkar S G, Rosendale D, Paturi G, Herath T D, Stoklosinski H, Phipps J E, et al. In vitro utilization of gold and green kiwifruit oligosaccharides by human gut microbial populations. Plant Foods for Human Nutrition. 2012; 67: 200-7.

Parnell J A, Reimer R A. Prebiotic fibres dose-dependently increase satiety hormones and alter Bacteroidetes and Firmicutes in lean and obese JCR:LA-cp rats. The British Journal of Nutrition. 2012; 107: 601-13.

Paturi G, Butts C A, Bentley-Hewitt K L, Ansell J 2014. Influence of green and gold kiwifruit on indices of large bowel function in healthy rats. J Food Sci 79(8): H1611-20.

Pryde S E, Duncan S H, Hold G L, Stewart C S, Flint H J. The microbiology of butyrate formation in the human colon. FEMS Microbiology Letters. 2002; 217: 133-9.

Qin J J, Li R Q, Raes J, Arumugam M, Burgdorf K S, Manichanh C, et al. A human gut microbial gene catalogue established by metagenomic sequencing. Nature. 2010; 464: 59-U70.

R Development Core Team 2008. R: A language and environment for statistical computing. R Foundation for Statistical Computing, Vienna, Austria.

RStudio. RStudio: Integrated development environment for R (Version 0.97.551) Computer software. Boston, Mass. http://www.rstudio.org/. 2012.

Rajilic-Stojanovic M, Biagi E, Heilig H G, Kajander K, Kekkonen R A, Tims S, et al. Global and deep molecular analysis of microbiota signatures in fecal samples from patients with irritable bowel syndrome. Gastroenterology. 2011; 141: 1792-801.

Rajilic-Stojanovic M, de Vos W M. The first 1000 cultured species of the human gastrointestinal microbiota. FEMS Microbiology Reviews. 2014; 38: 996-1047.

Ramirez-Farias C, Slezak K, Fuller Z, Duncan A, Holtrop G, Louis P 2009. Effect of inulin on the human gut microbiota: stimulation of *Bifidobacterium adolescentis* and *Faecalibacterium prausnitzii*. British Journal of Nutrition 101 (4): 541-550.

Rawls J F, Mahowald M A, Ley R E, Gordon J I. Reciprocal gut microbiota transplants from zebrafish and mice to germ-free recipients reveal host habitat selection, Cell. 2006; 127: 423-33.

Reid G 1999. The scientific basis for probiotic strains of *Lactobacillus*. Appl Environ Microbiol 65(9): 3763-6.

Rhee S H, Pothoulakis C, and Mayer E A, 2009. Principles and clinical implications of the brain-gut-enteric microbiota axis. Nature Reviews Gastroenterology & Hepatology 6: 306-314.

Richardson A J, Calder A G, Stewart C S, Smith A. 1989. Simultaneous determination of volatile and non-volatile acidic fermentation products of anaerobes by capillary gas-chromatography. Lett. Appl. Microbiol. 9: 5-8.

Rigottier-Gois L. 2013. Dysbiosis in inflammatory bowel diseases: the oxygen hypothesis. The ISME Journal 7: 1256-1261.

Rinttila T, Kassinen A, Malinen E, Krogius L, Palva A 2004. Development of an extensive set of 16S rDNA-targeted primers for quantification of pathogenic and indigenous bacteria in faecal samples by real-time PCR, Journal of Applied Microbiology 97(6): 1166-1177.

Rosendale D I, Maddox I S, Miles M C, Rodier M, Skinner M, Sutherland J. 2008. High-throughput microbial bioassays to screen potential New Zealand functional food ingredients intended to manage the growth of probiotic and pathogenic gut bacteria. International Journal of Food Science and Technology, 43(12): 2257-2267.

Rumah K R, Linden J, Fischetti V A, Vartanian T 2013. Isolation of *Clostridium perfringens* type B in an individual at first clinical presentation of multiple sclerosis provides clues for environmental triggers of the disease. PloS One 8(10): e76359.

Rush E C, Patel M, Plank L D, Ferguson L R. 2002. Kiwifruit promotes laxation in the elderly. Asia Pacific Journal of Clinical Nutrition 11(2): 164-168.

Sanchez B, Champomier-Verges M C, Collado Mdel C, Anglade P, Baraige F, Sanz Y, et al. Low-pH adaptation and the acid tolerance response of *Bifidobacterium longum* biotype *longum*. Appl, Environ. Microbiol. 2007; 73: 6450-9.

Sartor R B. Efficacy of probiotics for the management of inflammatory bowel disease. Gastroenterology & Hepatology. 2011; 7: 606-8.

Saulnier D M, Spinier J K, Gibson G R, Versalovic J. Mechanisms of probiosis and prebiosis: considerations for enhanced functional foods. Curr. Opin. Biotechnol. 2009; 20: 135-41.

Savino F, Pelle E, Palumeri E, Oggero R, Miniero R 2007. *Lactobacillus reuteri* (American Type Culture Collection Strain 55730) versus simethicone in the treatment of infantile colic: a prospective randomized study. Pediatrics 119(1): e124-30.

Scheperjans F, Aho V, Pereira P A, Koskinen K, Paulin L, Pekkonen E, Haapaniemi E, Kaakkola S, Eerola-Rautio J, Pohja M, Kinnunen E, Murros K, Auvinen P 2014. Gut microbiota are related to Parkinson's disease and clinical phenotype. Movement Disorders.

Schloss P D, Schubert A M, Zackular J P, Iverson K D, Young V B, Petrosino J F. Stabilization of the murine gut microbiome following weaning. Gut Microbes. 2012; 3: 383-93.

Seeram N. Associate Professor of Bioactive Botanical Research Laboratory, University of Rhode Island. Digestive Health Forum, NutraIngredients-USA, 25 Sep. 2014.

Singleton, Vernon L, Orthofer, Rudolf, Lamuela-Raventós, Rosa M. 1999. Analysis of total phenols and other oxidation substrates and antioxidants by means of folin-ciocalteu reagent 299: 152.

Skinner M A. 2012. Wellness foods based on the health benefits of fruit: gold kiwifruit for immune support and reducing symptoms of colds and influenza, Journal of Food and Drug Analysis 20(1): 261-264.

Sokol H, Pigneur B, Watterlot L, Lakhdari O, Bermudez-Humaran L G, Gratadoux J J, et al. *Faecalibacterium prausnitzii* is an anti-inflammatory commensal bacterium identified by gut microbiota analysis of Crohn disease patients. Proc. Natl. Acad. Sci. USA. 2008; 105: 16731-6.

Sokol H, Seksik P, Furet J P, Firmesse O, Nion-Larmurier I, Beaugerie L, et al. Low counts of *Faecalibacterium prausnitzii* in colitis microbiota. Inflammatory Bowel Diseases. 2009; 15: 1183-9.

Stonehouse W, Gammon C S, Beck K L, Conlon C A, Von Hurst P R, Kruger R. 2012. Kiwifruit: our daily prescription for health. Canadian Journal of Physiology and Pharmacology 91(6): 442-447.

D Sun-Waterhouse, I Wen, R Wibisono, L D Melton, S Wadhwa. 2009. Evaluation of the extraction efficiency for polyphenol extracts from by-products of green kiwifruit juicing. International Journal of Food Science & Technology. 44(12): 2644-2652.

Taras D, Simmering R, Collins M D, Lawson P A, Blaut M. Reclassification of *Eubacterium formicigenerans* Holdeman and Moore 1974 as *Dorea formicigenerans* gen. nov., comb. nov., and description of *Dorea longicatena* sp. nov., isolated from human faeces. International Journal of Systematic and Evolutionary Microbiology. 2002; 52: 423-8.

Timm D, Willis H, Thomas W, Sanders L, Boileau T, Slavin J. The use of a wireless motility device (SmartPill®) for the measurement of gastrointestinal transit time after a dietary fibre intervention. The British Journal of Nutrition. 2011; 105: 1337-42.

Tuohy K M, Kolida S, Lustenberger A M, Gibson G R. The prebiotic effects of biscuits containing partially hydrolysed guar gum and fructo-oligosaccharides—a human volunteer study. The British Journal of Nutrition. 2001; 86: 341-8.

Turnbaugh P J, Baeckhed F, Fulton L, Gordon J I 2008. Diet-induced obesity is linked to marked but reversible alterations in the mouse distal gut microbiome. Cell Host & Microbe 3(4): 213-223.

Udani J, Bloom D. 2013. Effects of kivia powder on Gut health in patients with occasional constipation: a randomized, double-blind, placebo-controlled study. Nutrition Journal 12(1): 78.

Vaahtovuo J, Munukka E, Korkeamaki M, Luukkainen R, Toivanen P 2008. Fecal microbiota in early rheumatoid arthritis. Journal of Rheumatology 35(8): 1500-5.

Vogt J A, Pencharz P B, Wolever T M S. L-Rhamnose increases serum propionate in humans. American Journal of Clinical Nutrition. 2004; 80: 89-94.

Walker A W, Duncan S H, McWilliam Leitch E C, Child M W, Flint H J. pH and peptide supply can radically alter bacterial populations and short-chain fatty acid ratios within microbial communities from the human colon. Appl. Environ. Microbiol, 2005; 71: 3692-700.

Walker A W, Duncan S H, Harmsen H J, Holtrop G, Welling G W, Flint H J 2008. The species composition of the human intestinal microbiota differs between particle-associated and liquid phase communities. Environ Microbiol 10(12): 3275-83.

Walker A W, Ince J, Duncan S H, Webster L M, Holtrop G, Ze X, et al. Dominant and diet-responsive groups of bacteria within the human colonic microbiota. ISME Journal. 2011; 5: 220-30.

Wang L, Christophersen C T, Sorich M J, Gerber J P, Angley M T, Conlon M A 2011. Low relative abundances of the mucolytic bacterium *Akkermansia muciniphila* and *Bifidobacterium* spp. in feces of children with autism. Applied and Environmental Microbiology 77(18): 6718-21.

Wang T, Cai G, Qiu Y, Fei N, Zhang M, Pang X, Jia W, Cai S, Zhao L 2012. Structural segregation of gut microbiota between colorectal cancer patients and healthy volunteers. ISME Journal 6(2): 320-9.

Wang Q, Garrity G M, Tiedje J M, Cole J R. Naive Bayesian classifier for rapid assignment of rRNA sequences into the new bacterial taxonomy. Appl. Environ. Microbiol. 2007; 73: 5261-7.

Williams B L, Hornig M, Parekh T, Lipkin W I 2012. Application of novel PCR-based methods for detection, quantitation, and phylogenetic characterization of Sutterella species in intestinal biopsy samples from children with autism and gastrointestinal disturbances. mBio 3(1).

Willing B P, Dicksved J, Halfvarson J, Andersson A F, Lucio M, Zheng Z, et al. A pyrosequencing study in twins shows that gastrointestinal microbial profiles vary with inflammatory bowel disease phenotypes. Gastroenterology. 2010; 139: 1844-54 e1.

Wong J M W, de Souza R, Kendall C W C, Emam A, Jenkins D J A. Colonic health: Fermentation and short chain fatty acids. Journal of Clinical Gastroenterology. 2006; 40: 235-43.

Wu G D, Chen J, Hoffmann C, Bittinger K, Chen Y Y, Keilbaugh S A, et a. Linking long-term dietary patterns with gut microbial enterotypes. Science. 2011; 334: 105-8.

Wu X, Ma C, Han L, Nawaz M, Gao F, Zhang X, Yu P, Zhao C, Li L, Zhou A, Wang J, Moore J E, Millar B C, Xu J 2010. Molecular characterisation of the faecal microbiota in patients with type II diabetes. Current Microbiology 61(1): 69-78.

Ze X, Duncan S H, Louis P, Flint H J. *Ruminococcus bromii* is a keystone species for the degradation of resistant starch in the human colon. ISME Journal. 2012; 6: 1535-43.

Zoppi G, Cinquetti M, Luciano A, Benini A, Miner A, and Bertazzoni M E. 1998. The intestinal ecosystem in chronic functional constipation. Acta Paediatrica 87: 836-841.

What is claimed is:

1. A method of:
    (i) maintaining or increasing beneficial bacteria in the digestive tract of a subject, wherein the beneficial bacteria comprise *Faecalibacterium prausnitzii*;
    (ii) maintaining or increasing *Faecalibacterium prausnitzii* in the digestive tract of a subject; or
    (iii) treating or preventing microbiota imbalance in the digestive tract of a subject, which imbalance includes inappropriate levels of *Faecalibacterium prausnitzii*;
    the method comprising administering a composition prepared from dried gold kiwifruit to a subject, wherein the dried gold kiwifruit is a Gold3 kiwifruit or a genetic derivative thereof,
    thereby maintaining or increasing the beneficial bacteria, maintaining or increasing the *Faecalibacterium prausnitzii*, or treating or preventing the microbiota imbalance in the subject.

2. The method according to claim 1, wherein the composition is administered by enteral, oral, or rectal administration.

3. The method according to claim 1, wherein the composition is administered as one or more of a tablet, capsule, liquid, jelly, or sachet.

4. The method according to claim 3, wherein the capsule is a gel capsule.

5. The method according to claim 1, wherein the composition is administered at a dosage of:
    (i) 2000 to 4000 mg of powder per day, or a liquid equivalent thereof;
    (ii) 250 to 2500 mg of powder per day, or a liquid equivalent thereof;
    (iii) approximately 2400 mg of powder per day, or a liquid equivalent thereof; or
    (iv) approximately 600 mg of powder per day, or a liquid equivalent thereof.

6. The method according to claim 1, wherein the composition is co-administered with one or more of:
    (i) a further digestive aid;
    (ii) probiotic, prebiotic, or synbiotic compositions; or
    (iii) fibre and/or a digestive enzyme.

7. The method according to claim 1, wherein the composition is further supplemented with polyphenols.

8. The method according to claim 1, wherein the beneficial bacteria are selected from: the group of *Bacteroides-Prevotella-Porphyromonas*, *Bifidobacterium* spp., *Lactobacillus* spp., and the *Lachnospiraceae* group.

9. The method according to claim 1, wherein the beneficial bacteria are selected from: *Clostridium coccoides*, *Bacteroides fragilis*, *Bacteroides thetaiotaomicron*, *Bacteroides ovatus*, *Bacteroides cellulosilyticus*, *Roseburia intestinalis*, *Roseburia inulinovorans*, *Ruminococcus bromii*, and *Ruminococcus flavefaciens*.

10. The method according to claim 1, wherein the subject has one or more symptoms of inflammation.

11. The method according to claim 1, wherein the subject has one or more symptoms of: bowel irregularity, Crohn's disease, ulcerative colitis, irritable bowel syndrome, inflammatory bowel disease, gastrointestinal cancer, allergy, atopy, or diabetes.

12. A method of increasing or ameliorating a decrease in *Faecalibacterium prausnitzii* levels in the digestive tract of a subject, and thereby:
    (i) treating or preventing constipation in the subject;
    (ii) maintaining or improving bowel regularity in the subject; or
    (iii) treating or preventing irritable bowel syndrome or inflammatory bowel disease in the subject;
    the method comprising administering a composition prepared from dried gold kiwifruit to a subject, wherein the dried gold kiwifruit is a Gold3 kiwifruit or a genetic derivative thereof,
    thereby treating or preventing the constipation, maintaining or improving the bowel regularity, or treating or preventing the irritable bowel syndrome or inflammatory bowel syndrome in the subject.

13. The method according to claim 12, wherein the composition is administered by enteral, oral, or rectal administration.

14. The method according to claim 12, wherein the composition is administered as one or more of a tablet, capsule, liquid, jelly, or sachet.

15. The method according to claim 12, wherein the capsule is a gel capsule.

16. The method according to claim 12, wherein the composition is administered at a dosage of:
    (i) 2000 to 4000 mg of powder per day, or a liquid equivalent thereof;
    (ii) 250 to 2500 mg of powder per day, or a liquid equivalent thereof;
    (iii) approximately 2400 mg of powder per day, or a liquid equivalent thereof; or
    (iv) approximately 600 mg of powder per day, or a liquid equivalent thereof.

17. The method according to claim 12, wherein the composition is co-administered with one or more of:
    (i) a further digestive aid;
    (ii) probiotic, prebiotic, or synbiotic compositions; or
    (iii) fibre and/or a digestive enzyme.

18. The method according to claim 12, wherein the composition is further supplemented with polyphenols.

* * * * *